US009777072B2

(12) United States Patent
Lee et al.

(10) Patent No.: US 9,777,072 B2
(45) **Date of Patent: *Oct. 3, 2017**

(54) PROTEIN COMPLEX AND METHOD OF PREPARING SAME

(71) Applicant: Samsung Electronics Co., Ltd., Suwon-si, Geyonggi-do (KR)

(72) Inventors: Jae-il Lee, Yongin-si (KR); Hye-young Suh, Hwaseong-si (KR); Yoon-aa Choi, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 180 days.

This patent is subject to a terminal disclaimer.

(21) Appl. No.: 13/727,135

(22) Filed: Dec. 26, 2012

(65) Prior Publication Data

US 2013/0196377 A1 Aug. 1, 2013

(30) Foreign Application Priority Data

Dec. 26, 2011 (KR) ........................ 10-2011-0142384

(51) Int. Cl.
*C07K 16/46* (2006.01)
*C07K 16/22* (2006.01)
*C07K 16/28* (2006.01)

(52) U.S. Cl.
CPC ............ *C07K 16/468* (2013.01); *C07K 16/22* (2013.01); *C07K 16/2863* (2013.01); *C07K 2319/50* (2013.01); *C07K 2319/95* (2013.01)

(58) Field of Classification Search
CPC .. C07K 16/2863; C07K 16/22; C07K 16/468; C07K 2317/622; C07K 2319/50; C07K 2317/95; C07K 2319/95; A61K 47/48
See application file for complete search history.

(56) References Cited

U.S. PATENT DOCUMENTS

| | | | | |
|---|---|---|---|---|
| 5,837,242 | A | 11/1998 | Holliger et al. | |
| 5,932,448 | A | 8/1999 | Tso et al. | |
| 6,121,424 | A | 9/2000 | Whitlow et al. | |
| 6,294,353 | B1 * | 9/2001 | Pack et al. | 435/69.1 |
| 7,498,024 | B2 | 3/2009 | Fang et al. | |
| 7,696,320 | B2 | 4/2010 | Ignatovich et al. | |
| 2004/0071696 | A1 | 4/2004 | Adams et al. | |
| 2005/0136050 | A1 | 6/2005 | Kufer et al. | |
| 2006/0088529 | A1 | 4/2006 | Leung et al. | |
| 2006/0099205 | A1 | 5/2006 | Adams et al. | |
| 2006/0147959 | A1 | 7/2006 | Bell et al. | |
| 2007/0020267 | A1 | 1/2007 | Fuh et al. | |
| 2007/0166788 | A1 * | 7/2007 | Jin | C07K 14/705 435/69.1 |
| 2008/0138339 | A1 | 6/2008 | Huang et al. | |
| 2009/0010840 | A1 | 1/2009 | Adams et al. | |
| 2009/0182127 | A1 | 7/2009 | Kjaergaard et al. | |
| 2009/0202532 | A1 | 8/2009 | Kumagai et al. | |
| 2009/0304696 | A1 * | 12/2009 | Lawson | C07K 16/00 424/135.1 |
| 2010/0092495 | A1 | 4/2010 | Chari | |
| 2010/0189727 | A1 * | 7/2010 | Rodeck et al. | 424/178.1 |
| 2010/0254989 | A1 | 10/2010 | Bossenmaier et al. | |
| 2012/0230995 | A1 | 9/2012 | Weidanz et al. | |
| 2013/0202596 | A1 * | 8/2013 | Salas | C07K 14/745 424/134.1 |

FOREIGN PATENT DOCUMENTS

| | | | |
|---|---|---|---|
| EP | 1136556 | A1 | 9/2001 |
| EP | 0894135 | B1 | 8/2004 |
| KR | 2008-0074231 | A | 8/2008 |
| WO | WO 02-08293 | A2 | 1/2002 |
| WO | WO 2004-094613 | A2 | 11/2004 |
| WO | WO 2005/075514 | * | 8/2005 |
| WO | WO2012006635 | * | 1/2012 |

OTHER PUBLICATIONS

Rudikoff et al., Proc. Natl. Acad. Sci. USA vol. 79: 1979-1983, 1982.*
Stancoviski et al., Proc. Nat. Acad. Sci. 88: 8691-8695, 1991.*
Jiang et al., J. Biol. Chem. 280 (6): 4656-4662, Feb. 11, 2005.*
Yu et al., Investigative Ophthalmology & Visual Science 49(2): 522-527, Feb. 2008.*
Cochran et al., J. Immunol. Meth. 287: 147-158, 2004.*
Paul, Fundamental Immunology, (textbook), 1993, pp. 292-295, 1993.*
Mabry et al., Protein Engineering, Design, and Selection, 23: 115-127, 2010.*
Stols et al., Protein Expression and Purification 25: 8-15, 2002.*
Merchant et al, Nature Biotechnology 16: 677-681, Jul. 1998.*
Korean Intellectual Property Office, International Search Report for International Patent Application No. PCT/KR2012/011416 (Apr. 22, 2013).
Arathoon et al., "A method for making multispecific antibodies having heteromultimeric and common components", *Expert Opinion on Therapeutic Patents*, 9 (6): 785-790 (1999).
Extended European Search Report for 13190818.8 mailed Feb. 18, 2014.
Cochran et al., *J. Immunol. Meth.*, 287:147-158 (2004).
Jiang et al., *J. Biol. Chem.*, 280(6): 4656-4662 (2005).
Paul, *Fundamental Immunology* (textbook), 1993: 292-295 (1993).
Rudikoff et al., *Proc. Nat. Acad. Sci. USA*, 79: 1979-1983 (1982).
Stancoviski et al., *Proc. Nat. Acad. Sci.*, 88:8691-8695 (1991).
Yu et al., *Investigative Opthalmology & Visual Science*, 49(2): 522-527 (2008).
Horak et al., "Isolation of scFvs to In Vitro Produced Extracellular Domains of EGFR Family Memembers," *Cancer Biotherapy & Radiopharmaceuticals*, vol. 20, No. 6 (2005).
Mabry et al., Protein Engineering, *Design, and Selection 23*: 115-127 (2010).
Stols et al., Protein Expression and Purification, 25: 8-15 (2002).

* cited by examiner

*Primary Examiner* — Phuong Huynh
(74) *Attorney, Agent, or Firm* — Leydig, Voit & Mayer, Ltd.

(57) ABSTRACT

A protein complex including at least two monoclonal antibodies is provided. By using the protein complex, a system for simultaneously targeting at least two antigens is effectively constructed.

3 Claims, 5 Drawing Sheets

PROTEIN COMPLEX AND METHOD OF PREPARING SAME

CROSS-REFERENCE TO RELATED APPLICATIONS

This application claims the benefit of Korean Patent Application No. 10-2011-0142384, filed on Dec. 26, 2011, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 429,994-Byte ASCII (Text) file named "711759_ST25.TXT-Substitute," created on Apr. 23, 2015.

BACKGROUND

1. Field

The present disclosure relates to protein complexes and methods of preparing same.

2. Description of the Related Art

Monoclonal antibodies have been leading a new drug market and developed as a therapeutic agent for a variety of targets. In many cases, however, monoclonal antibodies do not have a satisfactory efficacy and development thereof as a new drug has limitations due to their high manufacturing costs. To address these problems, research into bi-specific antibodies has been continuously conducted since the middle 1980s. In spite of so much effort, a leading technology for producing bi-specific antibodies has not yet been reported.

A preexisting method of producing bi-specific antibodies has disadvantages: difficulties in mass producing bi-specific antibodies and difficulties in commercialization thereof due to low efficacy and side effects. Recently, thanks to advanced antibody engineering, competitive new antibody platforms have emerged, but the antibody platforms are still in a verification stage.

Therefore, there is still a need to develop a new protein complex and method of preparing antibodies or antibody-like constructions, particularly those that enable the production of antibody or antibody-like molecules specific to at least two heteroantigens.

SUMMARY

Provided are protein complexes for the production of antibodies. In particular, there is provided a protein complex comprising at least two polypeptides each comprising an antigen binding site; and a linker that links the at least two polypeptides to each other, wherein the linker comprises a linking group and a tag attached to at least one terminus thereof, wherein the tag also is linked to a terminus of one of the at least two polypeptides and includes a cleavable amino acid sequence. A method for producing the protein complex, and related methods and compositions, also are provided.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
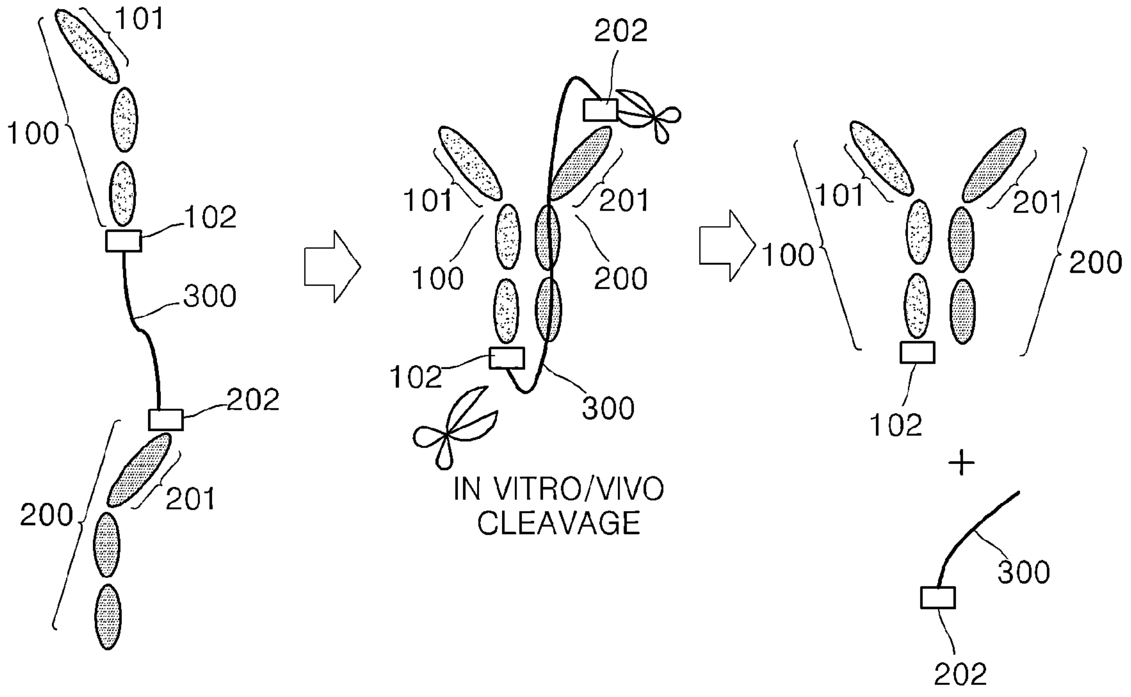
FIG. 1 is a schematic diagram illustrating a protein complex including at least two polypeptides, according to embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

According to an embodiment of the present invention, a protein complex includes at least two polypeptides each including an antigen binding site (also referred to herein as an "antigen-binding polypeptide"); and a linker that links the at least two polypeptides to each other, in which the linker includes a linking group and a tag attached to at least one terminus of the linking group. The tag is, in turn, linked to one of the termini of the polypeptides and includes a cleavable amino acid sequence. Thus, the protein complex has the general structure:

(antigen-binding polypeptide)-(linker)-(antigen-binding polypeptide)

which can more particularly be represented showing the linking group and one or two tag sequences as follows:

(antigen-binding polypeptide)-(tag)-(linking group)-(antigen-binding polypeptide) or (antigen-binding polypeptide)-(tag)-(linking group)-(antigen-binding polypeptide).

Figure 2:
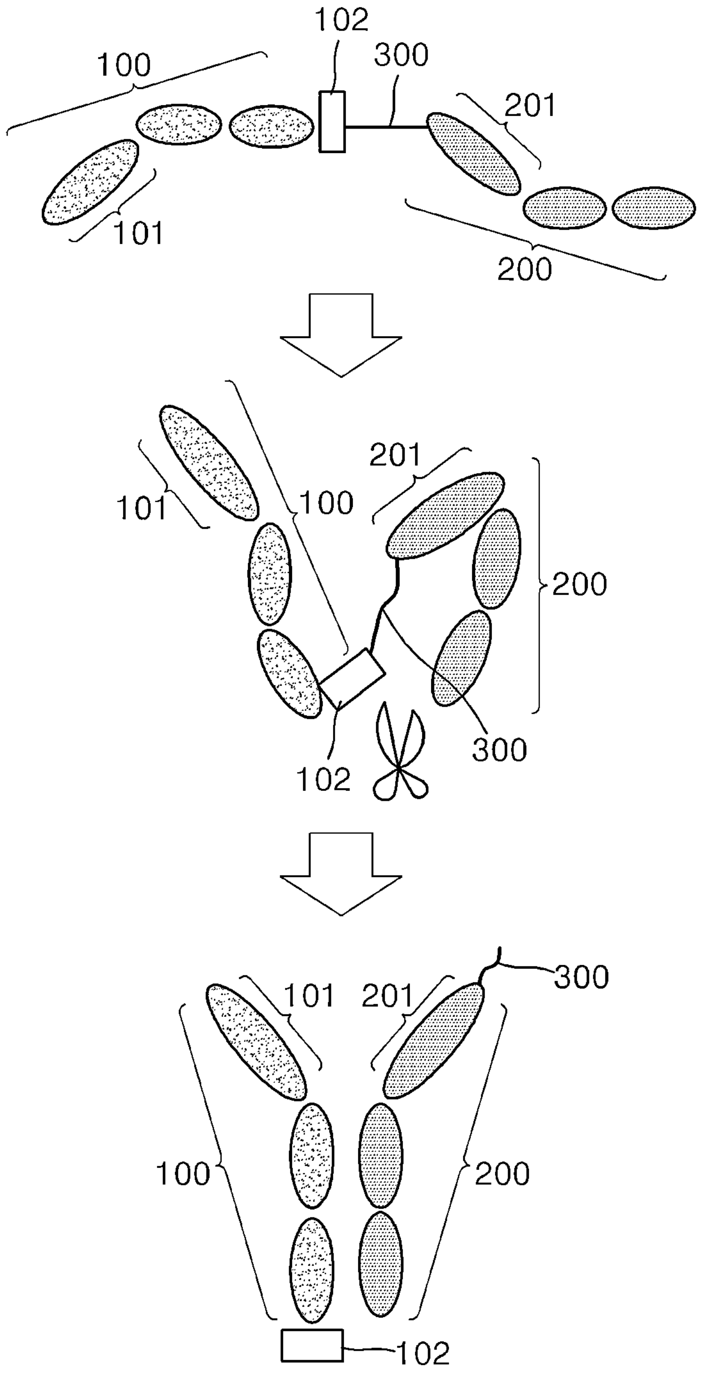
FIG. 2 is a schematic diagram illustrating a protein complex including at least two polypeptides, according to embodiments.

Without wishing to be bound by any particular theory as to the mechanism of the invention, the protein complex configured as described herein allows the antigen-binding polypeptides to self-assemble into an antigen-binding construct before or after cleavage of the tag region of the linker, as illustrated, for example, in FIGS. 1 and 2. The term "protein complex" is intended to encompass the above-described construct, whether in a folded (e.g., assembled) or unfolded state. Thus, the protein complex includes a fusion protein.

The protein complex may include at least two polypeptides each including an antigen binding site. In some embodiments, the protein complex may include more than two polypeptides having antigen binding sites, for example, three or more such polypeptides, or even four or more such polypeptides. In these embodiments, each antigen-binding polypeptide is bound to at least one other antigen-binding polypeptide by a linker. All aspects of the linker are as otherwise described herein.

The term “antigen binding site” used herein refers to a site to which an antigen binds. The antigen binding site may be an epitope binds to which an immunoglobulin molecule binds, or the antigen binding site may comprise the binding moiety of an immunoglobulin (e.g., antibody) in whole or in part. Thus, for instance, the antigen binding site may include one or more complementarity determining regions (CDRs) of an antibody. A CDR is an amino acid sequence found in the variable region of a heavy chain or a light chain of an immunoglobulin, of which there are typically three, that provides a major contact residue in antigen or epitope-antibody binding and, thus, principally determines the binding affinity and/or specificity of an antibody. The three CDRs of the heavy chain and the light chain of an antibody are typically referred to as CDRH1, CDRH2, CDRH3 (wherein “H” refers to the heavy chain) and CDRL1, CDRL2, CDRL3 (wherein “L” refers to the light chain), respectively. The term “heavy chain” used herein is understood to include a full-length heavy chain including a variable region ($V_H$) having amino acid sequences that determine specificity for antigens and a constant region having three constant domains ($C_{H1}$, $C_{H2}$, and $C_{H3}$), and fragments thereof. In addition, the term “light chain” used herein is understood to include a full-length light chain including a variable region ($V_L$) having amino acid sequences that determine specificity for antigens and a constant region ($C_L$), and fragments thereof. Thus, the antigen-binding polypeptide may comprise as the antigen binding site one, two, or all three CDR regions of an antibody, and may be provided by a contiguous portion of the variable light or variable heavy regions of an antibody.

In an embodiment, one or both of the antigen-binding polypeptides may be an antibody or an antigen binding fragment thereof. The antibody or the antigen binding fragment thereof may be a heavy or light chain of an antibody or antigen-binding antibody fragment selected from the group consisting of a Fab fragment, a Fab' fragment, an Fv fragment, and an scFv fragment, or a single-domain antibody, but not limited thereto. An intact antibody includes four polypeptides: two full-length light chains and two full-length heavy chains, in which each light chain is linked to a heavy chain by disulfide bonds (SS-bond). The antibody has a constant region: a heavy chain constant region and a light chain constant region. There are five heavy chain classes (isotypes): gamma (γ), mu (μ), alpha (α), delta (δ), or epsilon (ϵ), and additionally several subclasses: gamma 1 (γ1), gamma 2(γ2), gamma 3(γ3), gamma 4(γ4), alpha 1(α1), or alpha 2(α2). The light chain constant region is either kappa (κ) or lambda (λ) type.

The term “antigen binding fragment(s)” used herein refers to fragments of an intact immunoglobulin, and any part of a polypeptide including antigen binding regions. For example, the antigen binding fragment may be a $F(ab')_2$ fragment, a Fab' fragment, a Fab fragment, an Fv fragment, an scFv fragment, or a single-domain antibody, but is not limited thereto. A Fab fragment has one antigen binding site and contains the variable regions of a light chain and a heavy chain, the constant region of the light chain, and the first constant region $C_{H1}$ of the heavy chain. A Fab' fragment is different from the Fab fragment in that the Fab' fragment additionally includes the hinge region of the heavy chain, including at least one cysteine residue at the C-terminus of the heavy chain $C_{H1}$ region. A $F(ab')_2$ fragment is produced whereby cysteine residues of the Fab' fragment are joined by a disulfide bond at the hinge region. An Fv fragment is a minimal antibody fragment having only heavy chain variable regions and light chain variable regions, and a recombinant technique for producing the Fv fragment is well known in the art. Two-chain Fv fragments may have a structure in which heavy chain variable regions are linked to light chain variable regions by a non-covalent bond. Single-chain Fv fragments generally may have a dimer structure as in the two-chain Fv fragments in which heavy chain variable regions are covalently bound to light chain variable regions via a peptide linker or heavy and light chain variable regions are directly linked to each other at the C-terminus thereof. The antigen binding fragment may be obtained using a protease (for example, a whole antibody is digested with papain to obtain Fab fragments, or is digested with pepsin to obtain $F(ab')_2$ fragments), and may be prepared by a genetic recombinant technique. A single-domain antibody (sdAb) is an antibody fragment consisting of a single, monomeric, variable antibody domain, such as the variable heavy domain ($V_H$). Single-domain antibodies typically have a very low molecular weight (generally about 12-15 kDa, but not limited thereto).

The antigen binding site may be located at the N-terminus of the polypeptides.

The protein complex may have antigen binding sites that are identical or different. When the antigen binding sites are different form one another, the antigen binding sites may have different sequences that target the same antigen, or the antigen binding sites may target different antigens. If the antigen binding sites target the same antigens, the antigen binding sites of the at least two antigen-binding polypeptides may bind to different epitopes of the same antigen. Examples of the antigens to which the antigen binding sites may bind include, but are not limited to, DLL4, VEGFR2, Notch1, Notch2, Notch3, Notch4, Notch(pan), JAG1, JAG2, DLL(pan), JAG(pan), ERBB(pan), c-Met, IGF-1 R, PDGFR, Patched, Hedgehog family polypeptides, Hedgehog(pan), WNT family polypeptides, WNT(pan), FZD1, FZD2, FZD3, FZD4, FZD5, FZD6, FZD7, FZD8, FZD9, FZD10, FZD(pan), LRP5, LRP6, CD20, IL-17, CD86, Muc16, PSCA, CD44, c-Kit, DDR1, DDR2, RSPO1, RSPO2, RSPO3, RSPO4, RSPO(pan), BMP family polypeptides, BMP(pan), BMPR1a, BMPR1b, and combinations thereof. Also, examples of the antigens capable of binding to the antigen binding sites include, but are not limited to, EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, fluorescein, lysozyme, toll-like receptor 9, erythropoietin, CD2, CD3, CD3E, CD4, CD11, CD11a, CD14, CD18, CD19, CD20, CD22, CD23, CD25, CD28, CD29, CD30, CD33 (p67 protein), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNF-beta2, TNF-alpha, TNF-alphabeta, TNF-R1, TNF-R11, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF-R, EPO; LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLADR, CTLA-4, T cell receptor, B7-1, B7-2, VNRintegrin, TGFbeta1, TGFbeta2, eotaxin1, BLyS (B-lymphocyte Stimulator), complement C5, IgE, factor VII, CD64, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, carbohydrate such as blood group antigen and carbohydrate associated therewith, Galili-Glycosylation, Gastrin, Gastrin receptors, tumor associated carbohydrate, Hapten NP-cap or NIP-cap, T cell receptor alpha/beta, E-selectin, digoxin, placental alkaline phosphatase (PLAP) and testicular PLAP-like alkaline phosphatase, transferrin receptor, Heparanase I, human cardiac myosin, Glycoprotein IIb/IIIa (GPIIb/IIIa), human cytomegalovirus (HCMV) gH envelope glycoprotein, HIV gp120, HCMV, respiratory syncital virus RSV F, RSVF Fgp, VNRintegrin, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, Clostridium perfringens toxin, and fragments thereof.

Each antigen-binding polypeptide may further include a region that facilitates assembly with another antigen-binding polypeptide, such as a disulfide-bridging region. The disulfide bridging region can be provided, for instance, by a hinge region of an antibody (e.g., the hinge-CH2-CH3 domain of an IgG antibody, particularly human IgG, or suitable fragment thereof). In embodiments where the antigen-binding polypeptide is an antibody or antibody fragment, the region that facilitates assembly with another antigen-binding polypeptide may be provided by the antibody or antibody fragment itself, or a suitable region may be additionally included in the polypeptide, particularly if the antibody or antibody fragment excludes such a region.

In an embodiment, the protein complex may include a linker that links at least two antigen-binding polypeptides to each other. The linker includes a linking group (also referred to as a linking sequence) and a tag attached to at least one terminus of the linking group. The linking group may be any moiety having a length and flexibility that allows the antigen-binding polypeptides to associate without one another and self-assemble into an antigen-binding protein complex, before or after cleavage of the tag region of the linker. For instance, the linking group may include a peptide, such as a polypeptide. The peptide linking group may be any of various linking groups known in the art. For example, the linking group may be a polypeptide comprising or consisting of 1 to 100 amino acids, for example, 2 to 50 amino acids.

The peptide linker allows the at least two polypeptides to be sufficiently spaced apart from each other so that each polypeptide can be folded in a secondary or tertiary structure which is suitable for appropriate function of the polypeptides. For example, the peptide linker may include small and/or charged residues, such as Gly, Asn and Ser residues, and may also include neutral amino acids such as Thr and Ala. Appropriate amino acid sequences for the peptide linker are well known in the art. Exemplary linkers include $(Gly-Gly)_n$ (SEQ ID NO: 82), $(Gly-Ser)_n$ (SEQ ID NO: 83), and $(Gly-Gly-Gly-Gly-Ser)_n$ (SEQ ID NO: 84), wherein n is an integer from 1-10. The length of the linker may be appropriately adjusted as long as it does not affect the function of the polypeptides.

The tag region of the linker mediates a linkage between the linker (e.g. the linking group of the linker) and at least one of the antigen-binding polypeptides. The tag region includes a cleavable amino acid sequence, such that the antigen-binding protein attached to the linker via the tag region can be separated from the linker when desired. In an embodiment, the linker may include a tag attached to at least one terminus of thereof, such that terminus of at least one of the antigen-binding polypeptides is attached to the linker by way of the tag region. In other words, the tag is linked to a terminus of the linking group and to one of the termini of an antigen-binding polypeptide. In another embodiment, the linker includes a tag at both termini of the linker, such that both of the at least two antigen-binding polypeptides are attached to the linker by way of a tag region. The antigen-binding polypeptides may be linked to the linker (e.g., to a tag region or the linking group, as appropriate) via the N-terminus or C-terminus of the antigen-binding polypeptide. In one embodiment, one of the at least two antigen-binding polypeptides is attached to the linker via the N-terminus, and the other antigen-binding polypeptide is attached to the linker via the C-terminus.

The tag may include an in vitro or in vivo cleavable amino acid sequence. The in vitro or in vivo cleavage may be performed by protease. For example, the tag may be selected from the group consisting of ubiquitin, ubiquitin-like protein, a TEV cleavage peptide (e.g., a peptide comprising the TEV protease cleavage site Glu-Asn-Leu-Tyr-Phe-Gln-(Gly/Ser)) (SEQ ID NOs: 85 and 86), and a furin cleavage peptide (e.g., a peptide comprising the furin cleavage site Arg-X-(Arg/Lys)-Arg) (SEQ ID NOs: 87 and 88), but is not limited thereto.

Ubiquitin (Ub) (Gene Accession No.: NP_001170884, NM_001177413) is the most conserved protein found in nature that consists of 76 amino acids and is a water-soluble protein exhibiting perfect homology among evolutionally various species, such as insects, trout, and humans. In addition, ubiquitin is known to be protein that is stable against pH changes, is not easily denatured at high temperatures, and is stable with respect to protease. Therefore, ubiquitin may improve an insolubility of the protein complex and may be easily cleaved in vitro or in vivo.

The ubiquitin or the ubiquitin-like protein may be selected from the group consisting of wild-type ubiquitin, a wild-type ubiquitin-like protein, mutant ubiquitin, and a mutant ubiquitin-like protein. The mutant ubiquitin is obtained by changing the amino acid sequence of wild-type ubiquitin into another amino acid sequence. For example, a mutant ubiquitin may be prepared by substituting Lys of wild-type ubiquitin with Arg. In mutant ubiquitins prepared by substituting Lys of wild-type ubiquitin with Arg, Lys residues that exist at the $6^{th}$, $11^{th}$, $27^{th}$, $29^{th}$, $33^{rd}$, $48^{th}$, and $63^{rd}$ amino acid positions may be substituted with Arg independently or in any combination. The ubiquitin-like protein is a protein having properties that are similar to those of ubiquitin. Examples of the ubiquitin-like protein include, but are not limited to, Nedd8 (NP_006147.1, NM_006156.1), SUMO-1(NP_001005781.1, NM_001005781), SUMO-2(NP_008868.3, NM_006937.3), NUB1(NP_001230280.1, NM_001243351.1), PIC1(AAB40388), UBL3(NP_009037.1, NM_007106.3), UBL5(NP_001041706.1, NM_001048241.2), ISG15(NP_005092.1, NM_005101.3).

The ubiquitin or ubiquitin-like protein has an amino acid sequence at the C-terminus which can be cleaved in vitro or in vivo by a protease. Amino acid sequences that the can be cleaved by a protease are known in the art and may be identified by routine methods, such as by searching commercial and non-commercial databases (e.g., the ExPASy™ database maintained by the Swiss Institute of Biotechnology (SIB), Quartier Sorge—Bâtiment Génopode, 1015 Lausanne, Switzerland). When the protein complex includes the cleavable amino acid sequence, the tag included in the protein complex is cleaved in vitro or in vivo, whereby at least two fusion proteins may function as a protein complex having a bi-specific or multi-specific antigen binding site.

In an embodiment, the protein complex may include a first polypeptide including a first antigen binding site at the N-terminus thereof; a second polypeptide including a second antigen binding site at the N-terminus thereof; and a linker that links the first and second polypeptides to each other. Preferably, the protein complex includes a first tag and a second tag at both termini of the linker, wherein the first tag is linked to the C-terminus of the first polypeptide, the second tag is linked to the N-terminus of the second polypeptide, and the first tag and the second tag each include a cleavable amino acid sequence.

In another embodiment, the protein complex may include a first polypeptide including a first antigen binding site at the N-terminus thereof; a second polypeptide including a second antigen binding site at the N-terminus thereof; and a linker that links the first and second polypeptides to each other, in which the linker includes a tag at one terminus thereof and the tag is linked to the C-terminus of the first polypeptide or the N-terminus of the second polypeptide and includes a cleavable amino acid sequence.

Specific examples of protein complexes are those comprising, consisting essentially of, or consisting of an amino acid sequence of SEQ ID NO: 8 to SEQ ID NO:

According to another embodiment of the present invention, there is provided a polynucleotide encoding a protein complex as described herein. The term "polynucleotide" used herein refers to a polymer of deoxyribonucleotide or ribonucleotide that exists as a single-stranded or double-stranded form. The polynucleotide includes RNA genome sequences, DNA (gDNA and cDNA), and RNA sequences transcribed therefrom, and includes analogues of natural polynucleotides, unless specifically mentioned. The polynucleotide includes nucleotide sequences encoding the amino acid sequences of the various elements of the protein complex.

Also provided is a polynucleotide comprising a nucleotide sequence complimentary to the polynucleotide encoding the protein complex as described herein, or fragment thereof. The complementary sequences include completely complementary sequences and substantially complementary sequences. For example, substantially complementary sequences are sequences that may be hybridized with nucleotide sequences encoding the amino acid sequences of the protein complex. Such polynucleotides may useful as probes, and may include a detectable label.

In addition, the nucleotide sequences encoding the amino acid sequence of the protein complex may be mutated. The mutations include addition, deletion or non-conservative or conservative substitution of nucleotides. A polynucleotide encoding the amino acid sequence of the protein complex is understood to include nucleotide sequences substantially identical to the nucleotide sequences described above. The substantially identical sequences may be sequences with at least 80% homology, at least 90% homology, or at least 95% homology to the nucleotide sequences, when the nucleotide sequences are aligned to correspond to each other as much as possible. The aligned nucleotide sequences are analyzed using an algorithm known in the art.

Specific examples of a polynucleotide encoding a protein complex as described herein include those comprising, consisting essentially of, or consisting of a nucleotide sequence selected from the group consisting of SEQ ID NO: 45 to SEQ ID NO: 81.

The polynucleotide may be in a vector, particularly a recombinant vector. The term "vector" used herein refers to a polynucleotide as a means of cloning the target gene, or expressing a target gene in a host cell. For example, the vector may be a plasmid vector, a cosmid vector, or a viral vector, such as a bacteriophage vector, an adenovirus vector, a retrovirus vector, and an adeno-associated virus vector. The recombinant vector may be prepared by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4AB, λ-Charon, λΔz1, and M13), or a virus (for example, SV40) known in the art.

In the recombinant vector, the polynucleotides encoding the protein complex may be operatively linked to a promoter. The term "operatively linked" used herein means a functional linkage between a nucleotide expression regulating sequence (for example, a promoter sequence) and other nucleotide sequences. Thus, the nucleotide expression regulating sequence may regulate the transcription and/or translation of the other nucleotide sequences.

The recombinant vector may be constructed for cloning or expression. For example, a vector for expression may be a vector known in the art for expressing a foreign protein in a plant, animal, or microorganism. The recombinant vector may be constructed using various methods known in the art.

The recombinant vector may be constructed for use in prokaryotic or eukaryotic host cells. For example, when a prokaryotic cell is used as the host cell, the expression vector used generally includes a strong promoter capable of initiating transcription (for example, $p_L^{\lambda}$ promoter, a CMV promoter, trp promoter, lac promoter, tac promoter, T7 promoter), a ribosome binding site for initiating translation, and a transcription/translation termination sequence. When a eukaryotic cell is used as the host cell, the vector may include an origin of replication acting in the eukaryotic cell, for example, f1 origin of replication, SV40 origin of replication, pMB1 origin of replication, adeno origin of replication, AAV origin of replication, CMV origin of replication or BBV origin of replication, but is not limited thereto. A promoter in an expression vector for a eukaryotic host cell may be a promoter derived from a mammalian genome (for example, a metallothionein promoter) or a promoter derived from a mammalian virus (for example, an adenovirus late promoter, a vaccinia virus 7.5K promoter, an SV40 promoter, a cytomegalovirus (CMV) promoter, and a tk promoter of HSV). A transcription termination sequence in an expression vector for a eukaryotic host cell may be, in general, a polyadenylation sequence.

According to another embodiment of the present invention, a host cell is provided which includes a polynucleotide encoding a protein complex as described herein, optionally in a vector. The host cell, which is capable of stably and consecutively cloning or expressing the recombinant vector, may be any host cell known in the art. A prokaryotic host cell may be, for example, a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*, or an intestinal bacterium, such as *Salmonella typhimurium, Serratia marcescens*, and various *Pseudomonas* species. A eukaryotic host cell may be, for example, a yeast (e.g., *Saccharomyce cerevisiae*), an insect cell, a plant cell, or an animal cell, for example, Sp2/0, Chinese hamster ovary (CHO) K1, CHO DG44, PER.C6, W138, BHK, COS-7, 293, HepG2, Huh7, 3T3, RIN, or an MDCK cell line.

The polynucleotide or the recombinant vector including the same may be transferred into the host cell using a method known in the art. For example, when a prokaryotic cell is used as a host cell, the transfer may be performed using a $CaCl_2$ method or an electroporation method, and when a eukaryotic cell is used as a host cell, the transfer may be performed by microinjection, calcium phosphate precipitation, electroporation, liposome-mediated transfection, or gene bombardment, but is not limited thereto.

The transformed host cell may be selected using a phenotype expressed by a selectable marker by a method known in the art. For example, when the selectable marker is a specific antibiotic resistance gene, a transformant is cultured in a medium including the antibiotic, and thus, a transformant may easily be selected.

According to another embodiment of the present invention, a method of producing a multi-specific antibody is provided, which includes expressing a polynucleotide encoding a protein complex as described herein, optionally in a vector, in a host cell. When in a vector, the vector may have a promoter that is operatively linked to the polynucleotide to produce the protein complex.

The host cell may be in vivo or in vitro, thereby allowing production of the multi-specific antibody in vivo or in vitro.

In the case of in vivo production of the multi-specific antibody, a protein complex produced by expressing the polynucleotide, optionally in a recombinant vector, in a cell may be released to the outside of the cell (e.g., secreted from the cell) in the form of a complete multi-specific antibody. In other words, the protein complex may be produced as a multi-specific antibody such that translation occurs in the endoplasmic reticulum, and then the at least two polypeptides join together to spontaneously form polymers (e.g., associate into a dimer, trimer, etc.). Subsequently, the cleavable amino acid sequence of the tag included in the protein complex is cleaved by a protease present in the cell, and, as a result, a multi-specific antibody in a complete form is produced. The produced multi-specific antibody may be used in a purified form, and the purification method is known in the art. When two of the polypeptides are used, a bi-specific antibody may be produced using the aforementioned method.

In the case of in vitro production of the multi-specific antibody, the method may further include cleaving the tag after the expressing of the recombinant vector in a cell to produce the protein complex.

The protein complex in vitro is present such that the at least two polypeptides are linked to each other via a linker, and the at least two polypeptides join together to spontaneously form polymers (e.g., associate into a dimer, trimer, etc.). When two of the polypeptides are used, a bi-specific antibody may be produced using the aforementioned method.

In an embodiment, the cleaving process may be performed by contacting the protein complex with a protease that recognizes the cleavable amino acid sequence of the tag region of the protein complex. Examples of tag regions include, for instance, ubiquitin, ubiquitin-like protein, a TEV cleavage peptide, and a furin cleavage peptide. Thus, a protease capable of cleaving the TEV cleavage peptide or the furin cleavage peptide may be added to the protein complex, and, since the TEV cleavage peptide or the furin cleavage peptide is cleaved by the protease, a multi-specific antibody or a bi-specific antibody may be produced from the protein complex.

One or more embodiments of the present invention will now be described more fully with reference to the following examples. However, these examples are provided only for illustrative purposes and are not intended to limit the scope of the present invention.

FIGS. 1 and 2 are schematic diagrams illustrating a protein complex including at least two polypeptides. Referring to FIG. 1, a first polypeptide 100 including a first antigen binding site 101 includes a first tag 102 linked to the terminus thereof, and a second polypeptide 200 including a second antigen binding site 201 includes a second tag 202 linked to the terminus thereof. The first tag 102 and the second tag 202 are respectively linked to the termini of a polypeptide linker 300 composed of amino acid residues. The first tag 102 and the second tag 202 each consist of a protein such as ubiquitin or ubiquitin-like protein, and may be subjected to in vitro or in vivo cleavage. The first polypeptide 100 including a first antigen binding site 101 and the second polypeptide 200 including a second antigen binding site 201 may associate with each other so as to be combined in vitro or in vivo via complete, spontaneous binding, thereby forming a multi-specific protein complex having different antigen binding sites.

FIG. 2 illustrates a protein complex including the at least two polypeptides including antigen binding sites illustrated in FIG. 1, in which the second tag 202 is not included. As described above, a multi-specific protein complex having different antigen binding sites is formed through in vitro or in vivo cleavage of the protein complex. In this embodiment, however, the protein complex of FIG. 2 does not include the second tag 202, and thus the protein complex is present in the form such that the linker 300 is linked to the second polypeptide 200 including a second antigen binding site 201. In this regard, the linker 300 includes short amino acid sequences of 2 to 50, and thus does not affect a function of the second polypeptide 200 including a second antigen binding site 201.

Example 1

Construction of Expression Vector for Protein Complex Including Two Antigen Binding Sites To produce a protein complex of a bi-specific antibody which includes binding sites that are respectively specific to a vascular endothelial growth factor (VEGF) and an epidermal growth factor receptor (EGFR), an expression vector of the protein complex manufactured by GeneArt by request was used, and pCDNA 3.1 myc/his A (Invitrogen) was used as a vector for protein overexpression.

Figure 3:
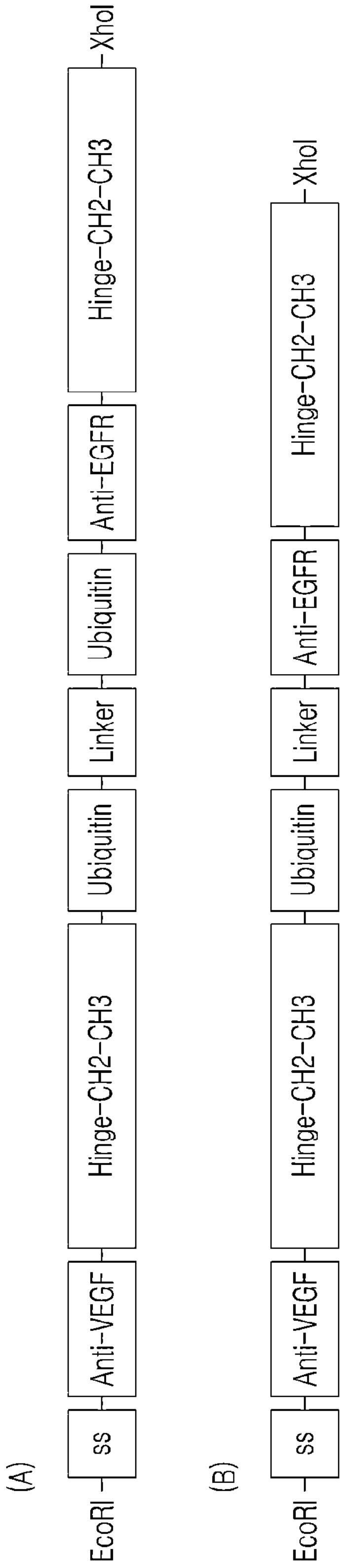
FIGS. 3A and B illustrate an amino acid sequence structure of a protein complex according to an embodiment.

In particular, as illustrated in FIGS. 3A and 3B, a single-sequence DNA (total 37 types according to V1/V2 and E1/E2, the length of the linker, and the number of ubiquitins corresponding to SEQ ID NOs: 45-81, which encode amino acid sequences of SEQ ID NOs: 8-41) corresponding to amino acid sequences of a protein complex that consists of a single-domain antibody consisting of a signal sequence (ss) (SEQ ID NO: 1), a VEGF-binding site, i.e., V1 or V2 (SEQ ID NO: 2 or 3), and an Fc domain including a hinge (SEQ ID NO: 4), a single-domain antibody consisting of an EGFR-binding site, i.e., E1 or E2 (SEQ ID NO: 5 or 6) and an Fc domain including a hinge (SEQ ID NO: 4), at least one ubiquitin tag (SEQ ID NO: 7), and a linker $(Gly\text{-}Gly)_n$ (SEQ ID NO: 82) or $(Gly\text{-}Gly\text{-}Gly\text{-}Gly\text{-}Ser)_n$ (SEQ ID NO: 84) peptide) was synthesized. To express the protein complex, nucleotide sequences of a DNA fragment inserted into a plasmid were represented by SEQ ID NOs: 45 to 81. The inserted DNA fragment includes a nucleotide sequence which is digested with EcoRI at the 5' terminus thereof and a nucleotide sequence which is digested with XhoI at the 3' terminus thereof, and thus may be inserted into the EcoRI-XhoI restriction site of the vector pcDNA3.1 myc/his A.—

Example 2

Expression of Protein Complex and Purification Of Bi-Specific Antibody

Figure 4:
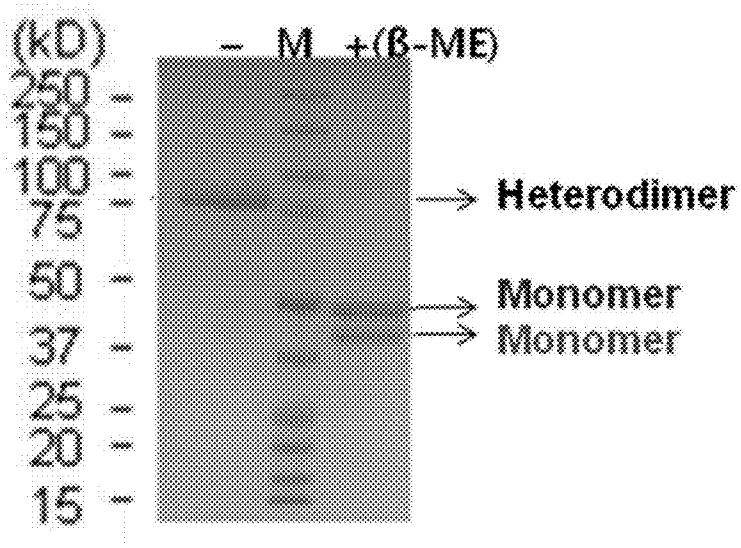
FIG. 4 illustrates sodium dodecyl sulfate polyacrylamide gel electrophoresis (SDS-PAGE) results of a protein complex according to an embodiment that is treated (+) or is not treated (−) with β-mercaptoethanol.

To overexpress a protein complex by using the vector constructed according to Example 1, Human embryonic kidney cells (HEK293-F, available from Korean Cell Line Bank) that were transformed with the vector were used. HEK293-F cells were maintained in an orbital shaker at 37° C. and 130 rpm under 8% $CO_2$ conditions. To transform the HEK293-F cells, first, the HEK293-F cells were separated from a medium by centrifugation, $1\times10^6$ of the HEK293-F cells were suspended in Freestyle 293 Expression media (Invitrogen), and then transformed with 100 μg of the vector by using a FreeStyle™ MAX reagent (Invitrogen). 7 to 8 days after the transformation, the resultant cells were centrifuged (4000×g, 10 min, 4° C.), and a supernatant was collected therefrom and filtered using a filter having a pore size of 0.22 micron. The obtained supernatant was used to purify a bi-specific antibody. The bi-specific antibody was isolated using a Protein A affinity column (GE Healthcare). First, the Protein A affinity column was equilibrated with 1× PBS (Invitrogen), the supernatant was applied to the equilibrated Protein A affinity column, the resultant column was washed using a washing buffer (1× PBS) having a volume that is five times that of the column, and then the bi-specific antibody was eluted using an IgG elution buffer (Thermo Scientific) containing 10% glycerol. The eluted solution was immediately neutralized with 1 M Tris-HCl (pH 9.0). The eluted solution obtained through the Protein A affinity column was applied to a desalting column (GE Healthcare) that had been equilibrated with 25 mM MES (pH 6.0), and then, while flowing the equilibrium solution to the desalting column, proteins eluted using a change in absorbance at UV 280 nm were collected, which was made as a sample. The protein sample was further applied to a Mono S column (GE Healthcare) that had been equilibrated with the equilibrium solution. Proteins that were not combined to the column were removed using the equilibrium solution, and proteins combined to the column were eluted using a washing solution consisting of 25 mM MES and a salt (NaCl) by slowly increasing the concentration of the salt from 0 mM to 250 mM. Fractions including the bi-specific antibody were confirmed by absorbance at 280 nm and SDS-PAGE, and the fractions were collected and concentrated using an Amicon Ultra-15 Centrifugal Filter (Milipore). The concentration of the purified protein was measured using BSA as a reference material. Thereafter, the concentrated bi-specific antibody was finally confirmed by SDS-PAGE. Before being loaded on a gel, the bi-specific antibody was divided into two groups, one of which was treated with 1 mM of β-mercaptoethanol and the other of which was not treated with β-mercaptoethanol, and they were then loaded on the gel. As a result, as illustrated in FIG. 4, in the case of bi-specific antibody treated with β-mercaptoethanol, it was confirmed that a single-domain antibody including a VEGF-binding site and a single-domain antibody including an EGFR-binding site were present in the form of monomers.

Example 3

Figure 5:
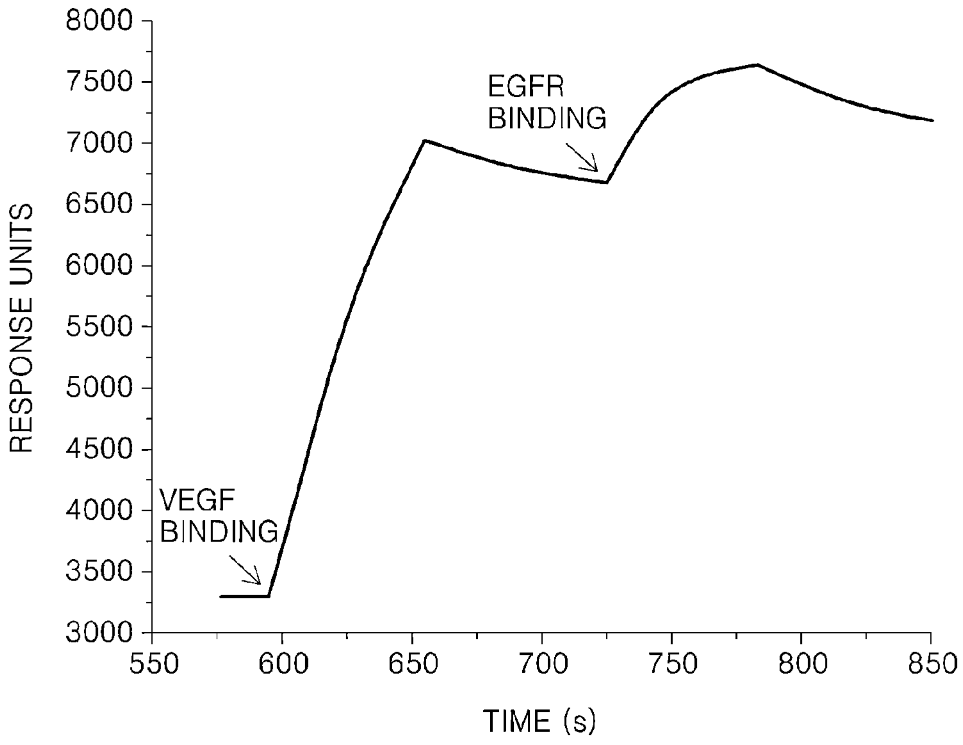
FIG. 5 is a sensorgram illustrating multi-specific antigen-antibody reaction effects of a protein complex according to an embodiment. Response units are on the y-axis and time (seconds) is on the x-axis.

Confirmation of Multi-Specific Antigen-Antibody Reaction of Bi-Specific Antibody Produced From Protein Complex To measure a binding affinity of a multi-specific antigen-antibody reaction of the bi-specific antibody produced according to Example 2, a surface Plasmon resonance test was performed using a BiacoreT100 instrument (GE healthcare). 1× HBS-EP (GE healthcare) was used as a running buffer and a dilution buffer. About 5,000 RU (response unit) of an Anti-human IgG antibody (Jackson Immuno Research) were immobilized on a surface of a CM5 chip (GE healthcare) by standard amine-coupling. About 500 RU of the bi-specific antibody was flown onto the CM5 chip so as to bind thereto, and then several concentrations (6.25 to 100 nM) of human EGFR extracellular domain (Prospec) or human VEGF (pangen) were flown onto the CM5 chip at a flow rate of 50 μL/min. A contact time (association phase) was 180 seconds, and a separation time (washing with running buffer) was 600 seconds. After each binding cycle was terminated, Glycine-HCl pH 2.0 (GE healthcare) as a regeneration solution was flown onto the chip at a flow rate of 50 μL/min for 1 minute to remove the combined antigen and antibody from the chip. A sensorgram was obtained therefrom such that a fitting process was performed in BIA evaluation software by using a 1:1 Langmuir binding model for the EGFR case and by using a bivalent analyte model for the VEGF case. The results are illustrated in FIG. 5.

To confirm that VEGF and EGFR simultaneously bind to the protein complex, about 2,500 RU of VEGF were immobilized on a CM5 chip by using the method described above. Subsequently, 500 nM of a bi-specific antibody was flown onto the chip at a flow rate of 10 μL/min for 1 minute, followed by the flowing of 500 nM of EGFR thereonto at the same flow rate for the same period of time. A surface of the chip was regenerated by flowing Glycine-HCl pH 2.0 (GE healthcare) thereonto at a flow rate of 10 μL/min for 1 minute.

A binding affinity ($K_D$ value, dissociation constant) of the bi-specific antibody to the VEGF or the EGFR obtained as a result of the experiment is shown in Table 1 below. In Table 1, $(V2Ub)_2$ denotes a monospecific antibody recognizing the VEGF, V2Ub-E2 denotes the bi-specific antibody of Example 2, and $(E2)_2$ denotes a monospecific antibody recognizing the EGFR.

TABLE 1

| | $(V2Ub)_2$ | V2Ub-E2 | $(E2)_2$ |
|---|---|---|---|
| $K_D$ value for VEGF (nM) | 3.40 | 2.85 | — |
| $K_D$ value for EGFR (nM) | — | 6.37 | 4.91 |

As described above, according to the one or more of the above embodiments of the present invention, by using a protein complex, a system that simultaneously targets at least two antigens may be effectively constructed.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A protein complex comprising any of SEQ ID NO: 8 to SEQ ID NO: 44.

2. A method of producing a multi-specific antibody from the protein complex of claim 1, wherein the protein complex comprises a tag comprising a protease cleavage site, the method comprising: cleaving the tag of the protein complex of claim 1.

3. The method of claim 2, wherein the tag is cleaved by contacting the protein complex with a protease that cleaves the tag.

* * * * *

SEQUENCE LISTING

```
<160> NUMBER OF SEQ ID NOS: 88

<210> SEQ ID NO 1
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: signal sequence

<400> SEQUENCE: 1

Met Gly Trp Ser Cys Ile Ile Leu Phe Leu Val Ala Thr Ala Thr Gly
1               5                   10                  15

Val His Ser


<210> SEQ ID NO 2
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: V1(binding site of VEGF)

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Pro Glu
            20                  25                  30

Leu Ser Trp Tyr Gln Gln Lys Pro Gly Lys Ala Pro Lys Leu Leu Ile
        35                  40                  45

Tyr His Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Met Phe Gln Pro Arg
                85                  90                  95

Thr Phe Gly Gln Gly Thr Lys Val Glu Ile Arg Arg
            100                 105


<210> SEQ ID NO 3
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: V2(binding site of VEGF)

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Phe Asn Gly
            20                  25                  30

Leu Ser Trp Tyr Gln Gln Lys Pro Gly Lys Ala Pro Lys Leu Leu Ile
        35                  40                  45

Tyr His Ser Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Leu Leu Tyr Pro Tyr
                85                  90                  95

Thr Phe Gly Gln Gly Thr Lys Val Glu Ile Lys Arg
            100                 105


<210> SEQ ID NO 4
<211> LENGTH: 232
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fc domain containing Hinge region

<400> SEQUENCE: 4

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140
```

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 5
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: E1(binding site of EGFR)

<400> SEQUENCE: 5

Asp Ile Gln Met Thr Gln Ser Pro Ser Ser Leu Ser Ala Ser Val Gly
1 5 10 15

Asp Arg Val Thr Ile Thr Cys Arg Ala Ser Gln Trp Ile Gly Ile Leu
20 25 30

Val Asp Trp Tyr Gln Gln Lys Pro Gly Glu Ala Pro Lys Leu Leu Ile
35 40 45

Tyr Tyr Ala Ser Phe Leu Gln Ser Gly Val Pro Ser Arg Phe Ser Gly
50 55 60

Ser Gly Phe Gly Thr Asp Phe Thr Leu Thr Ile Ser Ser Leu His Pro
65 70 75 80

Glu Asp Phe Ala Thr Tyr Tyr Cys Gln Gln Ala Asn Pro Ala Pro Leu
85 90 95

Thr Phe Gly Gln Gly Thr Lys Val Glu Ile Lys Arg
100 105

<210> SEQ ID NO 6
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: E2(binding site of EGFR)

<400> SEQUENCE: 6

Asp Ile Gln Met Thr Gln Ser Pro Thr Ser Leu Ser Ala Ser Val Gly
1 5 10 15

Asp Arg Val Thr Ile Thr Cys Arg Ala Ser Gln Trp Ile Gly Asn Leu
20 25 30

Leu Asp Trp Tyr Gln Gln Lys Pro Gly Glu Ala Pro Lys Leu Leu Ile
35 40 45

Tyr Tyr Ala Ser Phe Leu Gln Ser Gly Val Pro Ser Arg Phe Ser Gly
50 55 60

Gly Gly Phe Gly Thr Asp Phe Thr Leu Thr Ile Ser Ser Leu Gln Pro

-continued

```
65                  70                  75                  80

Glu Asp Phe Ala Thr Tyr Tyr Cys Gln Gln Ala Asn Pro Ala Pro Leu
                85                  90                  95

Thr Phe Gly Gln Gly Thr Lys Val Glu Ile Lys Arg
            100                 105


<210> SEQ ID NO 7
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: ubiquitin tag

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75


<210> SEQ ID NO 8
<211> LENGTH: 871
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #1

<400> SEQUENCE: 8

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160
```

-continued

```
Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Met Gln Ile Phe Val Lys Thr Leu Thr
    450                 455                 460

Gly Lys Thr Ile Thr Leu Glu Val Glu Pro Ser Asp Thr Ile Glu Asn
465                 470                 475                 480

Val Lys Ala Lys Ile Gln Asp Lys Glu Gly Ile Pro Pro Asp Gln Gln
                485                 490                 495

Arg Leu Ile Phe Ala Gly Lys Gln Leu Glu Asp Gly Arg Thr Leu Ser
            500                 505                 510

Asp Tyr Asn Ile Gln Lys Glu Ser Thr Leu His Leu Val Leu Arg Leu
        515                 520                 525

Arg Gly Gly Asp Ile Gln Met Thr Gln Ser Pro Ser Ser Leu Ser Ala
    530                 535                 540

Ser Val Gly Asp Arg Val Thr Ile Thr Cys Arg Ala Ser Gln Trp Ile
545                 550                 555                 560

Gly Ile Leu Val Asp Trp Tyr Gln Gln Lys Pro Gly Glu Ala Pro Lys
                565                 570                 575
```

-continued

```
Leu Leu Ile Tyr Tyr Ala Ser Phe Leu Gln Ser Gly Val Pro Ser Arg
            580                 585                 590

Phe Ser Gly Ser Gly Phe Gly Thr Asp Phe Thr Leu Thr Ile Ser Ser
        595                 600                 605

Leu His Pro Glu Asp Phe Ala Thr Tyr Tyr Cys Gln Gln Ala Asn Pro
    610                 615                 620

Ala Pro Leu Thr Phe Gly Gln Gly Thr Lys Val Glu Ile Lys Arg Glu
625                 630                 635                 640

Pro Lys Ser Cys Asp Lys Thr His Thr Cys Pro Pro Cys Pro Ala Pro
                645                 650                 655

Glu Leu Leu Gly Gly Pro Ser Val Phe Leu Phe Pro Pro Lys Pro Lys
            660                 665                 670

Asp Thr Leu Met Ile Ser Arg Thr Pro Glu Val Thr Cys Val Val Val
        675                 680                 685

Asp Val Ser His Glu Asp Pro Glu Val Lys Phe Asn Trp Tyr Val Asp
    690                 695                 700

Gly Val Glu Val His Asn Ala Lys Thr Lys Pro Arg Glu Glu Gln Tyr
705                 710                 715                 720

Asn Ser Thr Tyr Arg Val Val Ser Val Leu Thr Val Leu His Gln Asp
                725                 730                 735

Trp Leu Asn Gly Lys Glu Tyr Lys Cys Lys Val Ser Asn Lys Ala Leu
            740                 745                 750

Pro Ala Pro Ile Glu Lys Thr Ile Ser Lys Ala Lys Gly Gln Pro Arg
        755                 760                 765

Glu Pro Gln Val Tyr Thr Leu Pro Pro Ser Arg Glu Glu Met Thr Lys
    770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
        835                 840                 845

Cys Ser Val Met His Glu Ala Leu His Asn His Tyr Thr Gln Lys Ser
    850                 855                 860

Leu Ser Leu Ser Pro Gly Lys
865                 870


<210> SEQ ID NO 9
<211> LENGTH: 876
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #2

<400> SEQUENCE: 9

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45
```

-continued

```
Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Met Gln Ile Phe
    450                 455                 460
```

-continued

```
Val Lys Thr Leu Thr Gly Lys Thr Ile Thr Leu Glu Val Glu Pro Ser
465                 470                 475                 480

Asp Thr Ile Glu Asn Val Lys Ala Lys Ile Gln Asp Lys Glu Gly Ile
                485                 490                 495

Pro Pro Asp Gln Gln Arg Leu Ile Phe Ala Gly Lys Gln Leu Glu Asp
            500                 505                 510

Gly Arg Thr Leu Ser Asp Tyr Asn Ile Gln Lys Glu Ser Thr Leu His
        515                 520                 525

Leu Val Leu Arg Leu Arg Gly Gly Asp Ile Gln Met Thr Gln Ser Pro
    530                 535                 540

Ser Ser Leu Ser Ala Ser Val Gly Asp Arg Val Thr Ile Thr Cys Arg
545                 550                 555                 560

Ala Ser Gln Trp Ile Gly Ile Leu Val Asp Trp Tyr Gln Gln Lys Pro
                565                 570                 575

Gly Glu Ala Pro Lys Leu Leu Ile Tyr Tyr Ala Ser Phe Leu Gln Ser
            580                 585                 590

Gly Val Pro Ser Arg Phe Ser Gly Ser Gly Phe Gly Thr Asp Phe Thr
        595                 600                 605

Leu Thr Ile Ser Ser Leu His Pro Glu Asp Phe Ala Thr Tyr Tyr Cys
    610                 615                 620

Gln Gln Ala Asn Pro Ala Pro Leu Thr Phe Gly Gln Gly Thr Lys Val
625                 630                 635                 640

Glu Ile Lys Arg Glu Pro Lys Ser Cys Asp Lys Thr His Thr Cys Pro
                645                 650                 655

Pro Cys Pro Ala Pro Glu Leu Leu Gly Gly Pro Ser Val Phe Leu Phe
            660                 665                 670

Pro Pro Lys Pro Lys Asp Thr Leu Met Ile Ser Arg Thr Pro Glu Val
        675                 680                 685

Thr Cys Val Val Val Asp Val Ser His Glu Asp Pro Glu Val Lys Phe
    690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
    770                 775                 780

Glu Glu Met Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
    850                 855                 860

Tyr Thr Gln Lys Ser Leu Ser Leu Ser Pro Gly Lys
865                 870                 875
```

-continued

<210> SEQ ID NO 10
<211> LENGTH: 881
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR specific binding peptides #3

<400> SEQUENCE: 10

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350
```

-continued

```
Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Asp Ile Gln
    530                 535                 540

Met Thr Gln Ser Pro Ser Ser Leu Ser Ala Ser Val Gly Asp Arg Val
545                 550                 555                 560

Thr Ile Thr Cys Arg Ala Ser Gln Trp Ile Gly Ile Leu Val Asp Trp
                565                 570                 575

Tyr Gln Gln Lys Pro Gly Glu Ala Pro Lys Leu Leu Ile Tyr Tyr Ala
            580                 585                 590

Ser Phe Leu Gln Ser Gly Val Pro Ser Arg Phe Ser Gly Ser Gly Phe
        595                 600                 605

Gly Thr Asp Phe Thr Leu Thr Ile Ser Ser Leu His Pro Glu Asp Phe
    610                 615                 620

Ala Thr Tyr Tyr Cys Gln Gln Ala Asn Pro Ala Pro Leu Thr Phe Gly
625                 630                 635                 640

Gln Gly Thr Lys Val Glu Ile Lys Arg Glu Pro Lys Ser Cys Asp Lys
                645                 650                 655

Thr His Thr Cys Pro Pro Cys Pro Ala Pro Glu Leu Leu Gly Gly Pro
            660                 665                 670

Ser Val Phe Leu Phe Pro Pro Lys Pro Lys Asp Thr Leu Met Ile Ser
        675                 680                 685

Arg Thr Pro Glu Val Thr Cys Val Val Val Asp Val Ser His Glu Asp
    690                 695                 700

Pro Glu Val Lys Phe Asn Trp Tyr Val Asp Gly Val Glu Val His Asn
705                 710                 715                 720

Ala Lys Thr Lys Pro Arg Glu Glu Gln Tyr Asn Ser Thr Tyr Arg Val
                725                 730                 735

Val Ser Val Leu Thr Val Leu His Gln Asp Trp Leu Asn Gly Lys Glu
            740                 745                 750

Tyr Lys Cys Lys Val Ser Asn Lys Ala Leu Pro Ala Pro Ile Glu Lys
        755                 760                 765

Thr Ile Ser Lys Ala Lys Gly Gln Pro Arg Glu Pro Gln Val Tyr Thr
```

```
    770                 775                 780

Leu Pro Pro Ser Arg Glu Glu Met Thr Lys Asn Gln Val Ser Leu Thr
785                 790                 795                 800

Cys Leu Val Lys Gly Phe Tyr Pro Ser Asp Ile Ala Val Glu Trp Glu
                805                 810                 815

Ser Asn Gly Gln Pro Glu Asn Asn Tyr Lys Thr Thr Pro Pro Val Leu
            820                 825                 830

Asp Ser Asp Gly Ser Phe Phe Leu Tyr Ser Lys Leu Thr Val Asp Lys
        835                 840                 845

Ser Arg Trp Gln Gln Gly Asn Val Phe Ser Cys Ser Val Met His Glu
    850                 855                 860

Ala Leu His Asn His Tyr Thr Gln Lys Ser Leu Ser Leu Ser Pro Gly
865                 870                 875                 880

Lys


<210> SEQ ID NO 11
<211> LENGTH: 886
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #4

<400> SEQUENCE: 11

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
```

-continued

```
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Met Gln Ile Phe Val Lys Thr Leu Thr Gly
465                 470                 475                 480

Lys Thr Ile Thr Leu Glu Val Glu Pro Ser Asp Thr Ile Glu Asn Val
                485                 490                 495

Lys Ala Lys Ile Gln Asp Lys Glu Gly Ile Pro Pro Asp Gln Gln Arg
            500                 505                 510

Leu Ile Phe Ala Gly Lys Gln Leu Glu Asp Gly Arg Thr Leu Ser Asp
        515                 520                 525

Tyr Asn Ile Gln Lys Glu Ser Thr Leu His Leu Val Leu Arg Leu Arg
    530                 535                 540

Gly Gly Asp Ile Gln Met Thr Gln Ser Pro Ser Ser Leu Ser Ala Ser
545                 550                 555                 560

Val Gly Asp Arg Val Thr Ile Thr Cys Arg Ala Ser Gln Trp Ile Gly
                565                 570                 575

Ile Leu Val Asp Trp Tyr Gln Gln Lys Pro Gly Glu Ala Pro Lys Leu
            580                 585                 590

Leu Ile Tyr Tyr Ala Ser Phe Leu Gln Ser Gly Val Pro Ser Arg Phe
        595                 600                 605

Ser Gly Ser Gly Phe Gly Thr Asp Phe Thr Leu Thr Ile Ser Ser Leu
    610                 615                 620

His Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655
```

Lys Ser Cys Asp Lys Thr His Thr Cys Pro Pro Cys Pro Ala Pro Glu
660 665 670

Leu Leu Gly Gly Pro Ser Val Phe Leu Phe Pro Pro Lys Pro Lys Asp
675 680 685

Thr Leu Met Ile Ser Arg Thr Pro Glu Val Thr Cys Val Val Val Asp
690 695 700

Val Ser His Glu Asp Pro Glu Val Lys Phe Asn Trp Tyr Val Asp Gly
705 710 715 720

Val Glu Val His Asn Ala Lys Thr Lys Pro Arg Glu Glu Gln Tyr Asn
725 730 735

Ser Thr Tyr Arg Val Val Ser Val Leu Thr Val Leu His Gln Asp Trp
740 745 750

Leu Asn Gly Lys Glu Tyr Lys Cys Lys Val Ser Asn Lys Ala Leu Pro
755 760 765

Ala Pro Ile Glu Lys Thr Ile Ser Lys Ala Lys Gly Gln Pro Arg Glu
770 775 780

Pro Gln Val Tyr Thr Leu Pro Pro Ser Arg Glu Glu Met Thr Lys Asn
785 790 795 800

Gln Val Ser Leu Thr Cys Leu Val Lys Gly Phe Tyr Pro Ser Asp Ile
805 810 815

Ala Val Glu Trp Glu Ser Asn Gly Gln Pro Glu Asn Asn Tyr Lys Thr
820 825 830

Thr Pro Pro Val Leu Asp Ser Asp Gly Ser Phe Phe Leu Tyr Ser Lys
835 840 845

Leu Thr Val Asp Lys Ser Arg Trp Gln Gln Gly Asn Val Phe Ser Cys
850 855 860

Ser Val Met His Glu Ala Leu His Asn His Tyr Thr Gln Lys Ser Leu
865 870 875 880

Ser Leu Ser Pro Gly Lys
885

<210> SEQ ID NO 12
<211> LENGTH: 891
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR specific binding peptides #5

<400> SEQUENCE: 12

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Arg Ala Ser Gln Trp Ile
35 40 45

Gly Pro Glu Leu Ser Trp Tyr Gln Gln Lys Pro Gly Lys Ala Pro Lys
50 55 60

Leu Leu Ile Tyr His Thr Ser Ile Leu Gln Ser Gly Val Pro Ser Arg
65 70 75 80

Phe Ser Gly Ser Gly Ser Gly Thr Asp Phe Thr Leu Thr Ile Ser Ser
85 90 95

Leu Gln Pro Glu Asp Phe Ala Thr Tyr Tyr Cys Gln Gln Tyr Met Phe

-continued

```
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Met Gln Ile Phe Val
465                 470                 475                 480

Lys Thr Leu Thr Gly Lys Thr Ile Thr Leu Glu Val Glu Pro Ser Asp
                485                 490                 495

Thr Ile Glu Asn Val Lys Ala Lys Ile Gln Asp Lys Glu Gly Ile Pro
            500                 505                 510

Pro Asp Gln Gln Arg Leu Ile Phe Ala Gly Lys Gln Leu Glu Asp Gly
        515                 520                 525
```

```
Arg Thr Leu Ser Asp Tyr Asn Ile Gln Lys Glu Ser Thr Leu His Leu
    530                 535                 540

Val Leu Arg Leu Arg Gly Gly Asp Ile Gln Met Thr Gln Ser Pro Ser
545                 550                 555                 560

Ser Leu Ser Ala Ser Val Gly Asp Arg Val Thr Ile Thr Cys Arg Ala
                565                 570                 575

Ser Gln Trp Ile Gly Ile Leu Val Asp Trp Tyr Gln Gln Lys Pro Gly
            580                 585                 590

Glu Ala Pro Lys Leu Leu Ile Tyr Tyr Ala Ser Phe Leu Gln Ser Gly
        595                 600                 605

Val Pro Ser Arg Phe Ser Gly Ser Gly Phe Gly Thr Asp Phe Thr Leu
    610                 615                 620

Thr Ile Ser Ser Leu His Pro Glu Asp Phe Ala Thr Tyr Tyr Cys Gln
625                 630                 635                 640

Gln Ala Asn Pro Ala Pro Leu Thr Phe Gly Gln Gly Thr Lys Val Glu
                645                 650                 655

Ile Lys Arg Glu Pro Lys Ser Cys Asp Lys Thr His Thr Cys Pro Pro
            660                 665                 670

Cys Pro Ala Pro Glu Leu Leu Gly Gly Pro Ser Val Phe Leu Phe Pro
        675                 680                 685

Pro Lys Pro Lys Asp Thr Leu Met Ile Ser Arg Thr Pro Glu Val Thr
    690                 695                 700

Cys Val Val Val Asp Val Ser His Glu Asp Pro Glu Val Lys Phe Asn
705                 710                 715                 720

Trp Tyr Val Asp Gly Val Glu Val His Asn Ala Lys Thr Lys Pro Arg
                725                 730                 735

Glu Glu Gln Tyr Asn Ser Thr Tyr Arg Val Val Ser Val Leu Thr Val
            740                 745                 750

Leu His Gln Asp Trp Leu Asn Gly Lys Glu Tyr Lys Cys Lys Val Ser
        755                 760                 765

Asn Lys Ala Leu Pro Ala Pro Ile Glu Lys Thr Ile Ser Lys Ala Lys
    770                 775                 780

Gly Gln Pro Arg Glu Pro Gln Val Tyr Thr Leu Pro Pro Ser Arg Glu
785                 790                 795                 800

Glu Met Thr Lys Asn Gln Val Ser Leu Thr Cys Leu Val Lys Gly Phe
                805                 810                 815

Tyr Pro Ser Asp Ile Ala Val Glu Trp Glu Ser Asn Gly Gln Pro Glu
            820                 825                 830

Asn Asn Tyr Lys Thr Thr Pro Pro Val Leu Asp Ser Asp Gly Ser Phe
        835                 840                 845

Phe Leu Tyr Ser Lys Leu Thr Val Asp Lys Ser Arg Trp Gln Gln Gly
    850                 855                 860

Asn Val Phe Ser Cys Ser Val Met His Glu Ala Leu His Asn His Tyr
865                 870                 875                 880

Thr Gln Lys Ser Leu Ser Leu Ser Pro Gly Lys
                885                 890
```

<210> SEQ ID NO 13
<211> LENGTH: 896
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
specific binding peptides #6

<400> SEQUENCE: 13

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400
```

-continued

```
Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Met Gln Ile Phe Val Lys Thr Leu Thr Gly Lys Thr Ile Thr Leu Glu
                485                 490                 495

Val Glu Pro Ser Asp Thr Ile Glu Asn Val Lys Ala Lys Ile Gln Asp
            500                 505                 510

Lys Glu Gly Ile Pro Pro Asp Gln Gln Arg Leu Ile Phe Ala Gly Lys
        515                 520                 525

Gln Leu Glu Asp Gly Arg Thr Leu Ser Asp Tyr Asn Ile Gln Lys Glu
    530                 535                 540

Ser Thr Leu His Leu Val Leu Arg Leu Arg Gly Gly Asp Ile Gln Met
545                 550                 555                 560

Thr Gln Ser Pro Ser Ser Leu Ser Ala Ser Val Gly Asp Arg Val Thr
                565                 570                 575

Ile Thr Cys Arg Ala Ser Gln Trp Ile Gly Ile Leu Val Asp Trp Tyr
            580                 585                 590

Gln Gln Lys Pro Gly Glu Ala Pro Lys Leu Leu Ile Tyr Tyr Ala Ser
        595                 600                 605

Phe Leu Gln Ser Gly Val Pro Ser Arg Phe Ser Gly Ser Gly Phe Gly
    610                 615                 620

Thr Asp Phe Thr Leu Thr Ile Ser Ser Leu His Pro Glu Asp Phe Ala
625                 630                 635                 640

Thr Tyr Tyr Cys Gln Gln Ala Asn Pro Ala Pro Leu Thr Phe Gly Gln
                645                 650                 655

Gly Thr Lys Val Glu Ile Lys Arg Glu Pro Lys Ser Cys Asp Lys Thr
            660                 665                 670

His Thr Cys Pro Pro Cys Pro Ala Pro Glu Leu Leu Gly Gly Pro Ser
        675                 680                 685

Val Phe Leu Phe Pro Pro Lys Pro Lys Asp Thr Leu Met Ile Ser Arg
    690                 695                 700

Thr Pro Glu Val Thr Cys Val Val Val Asp Val Ser His Glu Asp Pro
705                 710                 715                 720

Glu Val Lys Phe Asn Trp Tyr Val Asp Gly Val Glu Val His Asn Ala
                725                 730                 735

Lys Thr Lys Pro Arg Glu Glu Gln Tyr Asn Ser Thr Tyr Arg Val Val
            740                 745                 750

Ser Val Leu Thr Val Leu His Gln Asp Trp Leu Asn Gly Lys Glu Tyr
        755                 760                 765

Lys Cys Lys Val Ser Asn Lys Ala Leu Pro Ala Pro Ile Glu Lys Thr
    770                 775                 780

Ile Ser Lys Ala Lys Gly Gln Pro Arg Glu Pro Gln Val Tyr Thr Leu
785                 790                 795                 800

Pro Pro Ser Arg Glu Glu Met Thr Lys Asn Gln Val Ser Leu Thr Cys
                805                 810                 815
```

```
Leu Val Lys Gly Phe Tyr Pro Ser Asp Ile Ala Val Glu Trp Glu Ser
            820                 825                 830

Asn Gly Gln Pro Glu Asn Asn Tyr Lys Thr Thr Pro Pro Val Leu Asp
        835                 840                 845

Ser Asp Gly Ser Phe Phe Leu Tyr Ser Lys Leu Thr Val Asp Lys Ser
    850                 855                 860

Arg Trp Gln Gln Gly Asn Val Phe Ser Cys Ser Val Met His Glu Ala
865                 870                 875                 880

Leu His Asn His Tyr Thr Gln Lys Ser Leu Ser Leu Ser Pro Gly Lys
                885                 890                 895
```

```
<210> SEQ ID NO 14
<211> LENGTH: 901
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #7

<400> SEQUENCE: 14

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270
```

```
Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Gly Gly Gly Gly Ser Met Gln Ile Phe Val Lys Thr Leu Thr Gly Lys
                485                 490                 495

Thr Ile Thr Leu Glu Val Glu Pro Ser Asp Thr Ile Glu Asn Val Lys
            500                 505                 510

Ala Lys Ile Gln Asp Lys Glu Gly Ile Pro Pro Asp Gln Gln Arg Leu
        515                 520                 525

Ile Phe Ala Gly Lys Gln Leu Glu Asp Gly Arg Thr Leu Ser Asp Tyr
    530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Ser Ser Leu Ser Ala Ser Val
                565                 570                 575

Gly Asp Arg Val Thr Ile Thr Cys Arg Ala Ser Gln Trp Ile Gly Ile
            580                 585                 590

Leu Val Asp Trp Tyr Gln Gln Lys Pro Gly Glu Ala Pro Lys Leu Leu
        595                 600                 605

Ile Tyr Tyr Ala Ser Phe Leu Gln Ser Gly Val Pro Ser Arg Phe Ser
    610                 615                 620

Gly Ser Gly Phe Gly Thr Asp Phe Thr Leu Thr Ile Ser Ser Leu His
625                 630                 635                 640

Pro Glu Asp Phe Ala Thr Tyr Tyr Cys Gln Gln Ala Asn Pro Ala Pro
                645                 650                 655

Leu Thr Phe Gly Gln Gly Thr Lys Val Glu Ile Lys Arg Glu Pro Lys
            660                 665                 670

Ser Cys Asp Lys Thr His Thr Cys Pro Pro Cys Pro Ala Pro Glu Leu
        675                 680                 685
```

Leu Gly Gly Pro Ser Val Phe Leu Phe Pro Pro Lys Pro Lys Asp Thr
    690                 695                 700

Leu Met Ile Ser Arg Thr Pro Glu Val Thr Cys Val Val Val Asp Val
705                 710                 715                 720

Ser His Glu Asp Pro Glu Val Lys Phe Asn Trp Tyr Val Asp Gly Val
                725                 730                 735

Glu Val His Asn Ala Lys Thr Lys Pro Arg Glu Glu Gln Tyr Asn Ser
            740                 745                 750

Thr Tyr Arg Val Val Ser Val Leu Thr Val Leu His Gln Asp Trp Leu
        755                 760                 765

Asn Gly Lys Glu Tyr Lys Cys Lys Val Ser Asn Lys Ala Leu Pro Ala
    770                 775                 780

Pro Ile Glu Lys Thr Ile Ser Lys Ala Lys Gly Gln Pro Arg Glu Pro
785                 790                 795                 800

Gln Val Tyr Thr Leu Pro Pro Ser Arg Glu Glu Met Thr Lys Asn Gln
                805                 810                 815

Val Ser Leu Thr Cys Leu Val Lys Gly Phe Tyr Pro Ser Asp Ile Ala
            820                 825                 830

Val Glu Trp Glu Ser Asn Gly Gln Pro Glu Asn Asn Tyr Lys Thr Thr
        835                 840                 845

Pro Pro Val Leu Asp Ser Asp Gly Ser Phe Phe Leu Tyr Ser Lys Leu
    850                 855                 860

Thr Val Asp Lys Ser Arg Trp Gln Gln Gly Asn Val Phe Ser Cys Ser
865                 870                 875                 880

Val Met His Glu Ala Leu His Asn His Tyr Thr Gln Lys Ser Leu Ser
                885                 890                 895

Leu Ser Pro Gly Lys
            900

<210> SEQ ID NO 15
<211> LENGTH: 871
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR specific binding peptides #8

<400> SEQUENCE: 15

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

-continued

```
Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Met Gln Ile Phe Val Lys Thr Leu Thr
    450                 455                 460

Gly Lys Thr Ile Thr Leu Glu Val Glu Pro Ser Asp Thr Ile Glu Asn
465                 470                 475                 480

Val Lys Ala Lys Ile Gln Asp Lys Glu Gly Ile Pro Pro Asp Gln Gln
                485                 490                 495

Arg Leu Ile Phe Ala Gly Lys Gln Leu Glu Asp Gly Arg Thr Leu Ser
            500                 505                 510

Asp Tyr Asn Ile Gln Lys Glu Ser Thr Leu His Leu Val Leu Arg Leu
        515                 520                 525

Arg Gly Gly Asp Ile Gln Met Thr Gln Ser Pro Thr Ser Leu Ser Ala
    530                 535                 540
```

Ser Val Gly Asp Arg Val Thr Ile Thr Cys Arg Ala Ser Gln Trp Ile
545 550 555 560

Gly Asn Leu Leu Asp Trp Tyr Gln Gln Lys Pro Gly Glu Ala Pro Lys
565 570 575

Leu Leu Ile Tyr Tyr Ala Ser Phe Leu Gln Ser Gly Val Pro Ser Arg
580 585 590

Phe Ser Gly Gly Gly Phe Gly Thr Asp Phe Thr Leu Thr Ile Ser Ser
595 600 605

Leu Gln Pro Glu Asp Phe Ala Thr Tyr Tyr Cys Gln Gln Ala Asn Pro
610 615 620

Ala Pro Leu Thr Phe Gly Gln Gly Thr Lys Val Glu Ile Lys Arg Glu
625 630 635 640

Pro Lys Ser Cys Asp Lys Thr His Thr Cys Pro Pro Cys Pro Ala Pro
645 650 655

Glu Leu Leu Gly Gly Pro Ser Val Phe Leu Phe Pro Pro Lys Pro Lys
660 665 670

Asp Thr Leu Met Ile Ser Arg Thr Pro Glu Val Thr Cys Val Val Val
675 680 685

Asp Val Ser His Glu Asp Pro Glu Val Lys Phe Asn Trp Tyr Val Asp
690 695 700

Gly Val Glu Val His Asn Ala Lys Thr Lys Pro Arg Glu Glu Gln Tyr
705 710 715 720

Asn Ser Thr Tyr Arg Val Val Ser Val Leu Thr Val Leu His Gln Asp
725 730 735

Trp Leu Asn Gly Lys Glu Tyr Lys Cys Lys Val Ser Asn Lys Ala Leu
740 745 750

Pro Ala Pro Ile Glu Lys Thr Ile Ser Lys Ala Lys Gly Gln Pro Arg
755 760 765

Glu Pro Gln Val Tyr Thr Leu Pro Pro Ser Arg Glu Glu Met Thr Lys
770 775 780

Asn Gln Val Ser Leu Thr Cys Leu Val Lys Gly Phe Tyr Pro Ser Asp
785 790 795 800

Ile Ala Val Glu Trp Glu Ser Asn Gly Gln Pro Glu Asn Asn Tyr Lys
805 810 815

Thr Thr Pro Pro Val Leu Asp Ser Asp Gly Ser Phe Phe Leu Tyr Ser
820 825 830

Lys Leu Thr Val Asp Lys Ser Arg Trp Gln Gln Gly Asn Val Phe Ser
835 840 845

Cys Ser Val Met His Glu Ala Leu His Asn His Tyr Thr Gln Lys Ser
850 855 860

Leu Ser Leu Ser Pro Gly Lys
865 870

<210> SEQ ID NO 16
<211> LENGTH: 876
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
specific binding peptides #9

<400> SEQUENCE: 16

Met Gly Trp Ser Cys Ile Ile Leu Phe Leu Val Ala Thr Ala Thr Gly
1 5 10 15

-continued

```
Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430
```

-continued

```
Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Met Gln Ile Phe
    450                 455                 460

Val Lys Thr Leu Thr Gly Lys Thr Ile Thr Leu Glu Val Glu Pro Ser
465                 470                 475                 480

Asp Thr Ile Glu Asn Val Lys Ala Lys Ile Gln Asp Lys Glu Gly Ile
                485                 490                 495

Pro Pro Asp Gln Gln Arg Leu Ile Phe Ala Gly Lys Gln Leu Glu Asp
            500                 505                 510

Gly Arg Thr Leu Ser Asp Tyr Asn Ile Gln Lys Glu Ser Thr Leu His
        515                 520                 525

Leu Val Leu Arg Leu Arg Gly Gly Asp Ile Gln Met Thr Gln Ser Pro
    530                 535                 540

Thr Ser Leu Ser Ala Ser Val Gly Asp Arg Val Thr Ile Thr Cys Arg
545                 550                 555                 560

Ala Ser Gln Trp Ile Gly Asn Leu Leu Asp Trp Tyr Gln Gln Lys Pro
                565                 570                 575

Gly Glu Ala Pro Lys Leu Leu Ile Tyr Tyr Ala Ser Phe Leu Gln Ser
            580                 585                 590

Gly Val Pro Ser Arg Phe Ser Gly Gly Gly Phe Gly Thr Asp Phe Thr
        595                 600                 605

Leu Thr Ile Ser Ser Leu Gln Pro Glu Asp Phe Ala Thr Tyr Tyr Cys
    610                 615                 620

Gln Gln Ala Asn Pro Ala Pro Leu Thr Phe Gly Gln Gly Thr Lys Val
625                 630                 635                 640

Glu Ile Lys Arg Glu Pro Lys Ser Cys Asp Lys Thr His Thr Cys Pro
                645                 650                 655

Pro Cys Pro Ala Pro Glu Leu Leu Gly Gly Pro Ser Val Phe Leu Phe
            660                 665                 670

Pro Pro Lys Pro Lys Asp Thr Leu Met Ile Ser Arg Thr Pro Glu Val
        675                 680                 685

Thr Cys Val Val Val Asp Val Ser His Glu Asp Pro Glu Val Lys Phe
    690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
    770                 775                 780

Glu Glu Met Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
```

```
    850                 855                 860

Tyr Thr Gln Lys Ser Leu Ser Leu Ser Pro Gly Lys
865                 870                 875


<210> SEQ ID NO 17
<211> LENGTH: 881
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #10

<400> SEQUENCE: 17

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320
```

-continued

```
Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Asp Ile Gln
    530                 535                 540

Met Thr Gln Ser Pro Thr Ser Leu Ser Ala Ser Val Gly Asp Arg Val
545                 550                 555                 560

Thr Ile Thr Cys Arg Ala Ser Gln Trp Ile Gly Asn Leu Leu Asp Trp
                565                 570                 575

Tyr Gln Gln Lys Pro Gly Glu Ala Pro Lys Leu Leu Ile Tyr Tyr Ala
            580                 585                 590

Ser Phe Leu Gln Ser Gly Val Pro Ser Arg Phe Ser Gly Gly Gly Phe
        595                 600                 605

Gly Thr Asp Phe Thr Leu Thr Ile Ser Ser Leu Gln Pro Glu Asp Phe
    610                 615                 620

Ala Thr Tyr Tyr Cys Gln Gln Ala Asn Pro Ala Pro Leu Thr Phe Gly
625                 630                 635                 640

Gln Gly Thr Lys Val Glu Ile Lys Arg Glu Pro Lys Ser Cys Asp Lys
                645                 650                 655

Thr His Thr Cys Pro Pro Cys Pro Ala Pro Glu Leu Leu Gly Gly Pro
            660                 665                 670

Ser Val Phe Leu Phe Pro Pro Lys Pro Lys Asp Thr Leu Met Ile Ser
        675                 680                 685

Arg Thr Pro Glu Val Thr Cys Val Val Val Asp Val Ser His Glu Asp
    690                 695                 700

Pro Glu Val Lys Phe Asn Trp Tyr Val Asp Gly Val Glu Val His Asn
705                 710                 715                 720

Ala Lys Thr Lys Pro Arg Glu Glu Gln Tyr Asn Ser Thr Tyr Arg Val
                725                 730                 735

Val Ser Val Leu Thr Val Leu His Gln Asp Trp Leu Asn Gly Lys Glu
```

```
            740                 745                 750

Tyr Lys Cys Lys Val Ser Asn Lys Ala Leu Pro Ala Pro Ile Glu Lys
        755                 760                 765

Thr Ile Ser Lys Ala Lys Gly Gln Pro Arg Glu Pro Gln Val Tyr Thr
    770                 775                 780

Leu Pro Pro Ser Arg Glu Glu Met Thr Lys Asn Gln Val Ser Leu Thr
785                 790                 795                 800

Cys Leu Val Lys Gly Phe Tyr Pro Ser Asp Ile Ala Val Glu Trp Glu
                805                 810                 815

Ser Asn Gly Gln Pro Glu Asn Asn Tyr Lys Thr Thr Pro Pro Val Leu
            820                 825                 830

Asp Ser Asp Gly Ser Phe Phe Leu Tyr Ser Lys Leu Thr Val Asp Lys
        835                 840                 845

Ser Arg Trp Gln Gln Gly Asn Val Phe Ser Cys Ser Val Met His Glu
    850                 855                 860

Ala Leu His Asn His Tyr Thr Gln Lys Ser Leu Ser Leu Ser Pro Gly
865                 870                 875                 880

Lys


<210> SEQ ID NO 18
<211> LENGTH: 886
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #11

<400> SEQUENCE: 18

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
```

-continued

```
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Met Gln Ile Phe Val Lys Thr Leu Thr Gly
465                 470                 475                 480

Lys Thr Ile Thr Leu Glu Val Glu Pro Ser Asp Thr Ile Glu Asn Val
                485                 490                 495

Lys Ala Lys Ile Gln Asp Lys Glu Gly Ile Pro Pro Asp Gln Gln Arg
            500                 505                 510

Leu Ile Phe Ala Gly Lys Gln Leu Glu Asp Gly Arg Thr Leu Ser Asp
        515                 520                 525

Tyr Asn Ile Gln Lys Glu Ser Thr Leu His Leu Val Leu Arg Leu Arg
    530                 535                 540

Gly Gly Asp Ile Gln Met Thr Gln Ser Pro Thr Ser Leu Ser Ala Ser
545                 550                 555                 560

Val Gly Asp Arg Val Thr Ile Thr Cys Arg Ala Ser Gln Trp Ile Gly
                565                 570                 575

Asn Leu Leu Asp Trp Tyr Gln Gln Lys Pro Gly Glu Ala Pro Lys Leu
            580                 585                 590

Leu Ile Tyr Tyr Ala Ser Phe Leu Gln Ser Gly Val Pro Ser Arg Phe
        595                 600                 605

Ser Gly Gly Gly Phe Gly Thr Asp Phe Thr Leu Thr Ile Ser Ser Leu
    610                 615                 620
```

```
Gln Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655

Lys Ser Cys Asp Lys Thr His Thr Cys Pro Pro Cys Pro Ala Pro Glu
            660                 665                 670

Leu Leu Gly Gly Pro Ser Val Phe Leu Phe Pro Pro Lys Pro Lys Asp
        675                 680                 685

Thr Leu Met Ile Ser Arg Thr Pro Glu Val Thr Cys Val Val Val Asp
    690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
            740                 745                 750

Leu Asn Gly Lys Glu Tyr Lys Cys Lys Val Ser Asn Lys Ala Leu Pro
        755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
                885


<210> SEQ ID NO 19
<211> LENGTH: 891
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #12

<400> SEQUENCE: 19

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
```

-continued

```
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Met Gln Ile Phe Val
465                 470                 475                 480

Lys Thr Leu Thr Gly Lys Thr Ile Thr Leu Glu Val Glu Pro Ser Asp
                485                 490                 495
```

```
Thr Ile Glu Asn Val Lys Ala Lys Ile Gln Asp Lys Glu Gly Ile Pro
            500                 505                 510

Pro Asp Gln Gln Arg Leu Ile Phe Ala Gly Lys Gln Leu Glu Asp Gly
        515                 520                 525

Arg Thr Leu Ser Asp Tyr Asn Ile Gln Lys Glu Ser Thr Leu His Leu
    530                 535                 540

Val Leu Arg Leu Arg Gly Gly Asp Ile Gln Met Thr Gln Ser Pro Thr
545                 550                 555                 560

Ser Leu Ser Ala Ser Val Gly Asp Arg Val Thr Ile Thr Cys Arg Ala
                565                 570                 575

Ser Gln Trp Ile Gly Asn Leu Leu Asp Trp Tyr Gln Gln Lys Pro Gly
            580                 585                 590

Glu Ala Pro Lys Leu Leu Ile Tyr Tyr Ala Ser Phe Leu Gln Ser Gly
        595                 600                 605

Val Pro Ser Arg Phe Ser Gly Gly Gly Phe Gly Thr Asp Phe Thr Leu
    610                 615                 620

Thr Ile Ser Ser Leu Gln Pro Glu Asp Phe Ala Thr Tyr Tyr Cys Gln
625                 630                 635                 640

Gln Ala Asn Pro Ala Pro Leu Thr Phe Gly Gln Gly Thr Lys Val Glu
                645                 650                 655

Ile Lys Arg Glu Pro Lys Ser Cys Asp Lys Thr His Thr Cys Pro Pro
            660                 665                 670

Cys Pro Ala Pro Glu Leu Leu Gly Gly Pro Ser Val Phe Leu Phe Pro
        675                 680                 685

Pro Lys Pro Lys Asp Thr Leu Met Ile Ser Arg Thr Pro Glu Val Thr
    690                 695                 700

Cys Val Val Val Asp Val Ser His Glu Asp Pro Glu Val Lys Phe Asn
705                 710                 715                 720

Trp Tyr Val Asp Gly Val Glu Val His Asn Ala Lys Thr Lys Pro Arg
                725                 730                 735

Glu Glu Gln Tyr Asn Ser Thr Tyr Arg Val Val Ser Val Leu Thr Val
            740                 745                 750

Leu His Gln Asp Trp Leu Asn Gly Lys Glu Tyr Lys Cys Lys Val Ser
        755                 760                 765

Asn Lys Ala Leu Pro Ala Pro Ile Glu Lys Thr Ile Ser Lys Ala Lys
    770                 775                 780

Gly Gln Pro Arg Glu Pro Gln Val Tyr Thr Leu Pro Pro Ser Arg Glu
785                 790                 795                 800

Glu Met Thr Lys Asn Gln Val Ser Leu Thr Cys Leu Val Lys Gly Phe
                805                 810                 815

Tyr Pro Ser Asp Ile Ala Val Glu Trp Glu Ser Asn Gly Gln Pro Glu
            820                 825                 830

Asn Asn Tyr Lys Thr Thr Pro Pro Val Leu Asp Ser Asp Gly Ser Phe
        835                 840                 845

Phe Leu Tyr Ser Lys Leu Thr Val Asp Lys Ser Arg Trp Gln Gln Gly
    850                 855                 860

Asn Val Phe Ser Cys Ser Val Met His Glu Ala Leu His Asn His Tyr
865                 870                 875                 880

Thr Gln Lys Ser Leu Ser Leu Ser Pro Gly Lys
                885                 890
```

<210> SEQ ID NO 20
<211> LENGTH: 896

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #13

<400> SEQUENCE: 20

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Trp Ile
        35                  40                  45

Gly Pro Glu Leu Ser Trp Tyr Gln Gln Lys Pro Gly Lys Ala Pro Lys
    50                  55                  60

Leu Leu Ile Tyr His Thr Ser Ile Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Met Phe
            100                 105                 110

Gln Pro Arg Thr Phe Gly Gln Gly Thr Lys Val Glu Ile Arg Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365
```

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Met Gln Ile Phe Val Lys Thr Leu Thr Gly Lys Thr Ile Thr Leu Glu
                485                 490                 495

Val Glu Pro Ser Asp Thr Ile Glu Asn Val Lys Ala Lys Ile Gln Asp
            500                 505                 510

Lys Glu Gly Ile Pro Pro Asp Gln Gln Arg Leu Ile Phe Ala Gly Lys
        515                 520                 525

Gln Leu Glu Asp Gly Arg Thr Leu Ser Asp Tyr Asn Ile Gln Lys Glu
    530                 535                 540

Ser Thr Leu His Leu Val Leu Arg Leu Arg Gly Gly Asp Ile Gln Met
545                 550                 555                 560

Thr Gln Ser Pro Thr Ser Leu Ser Ala Ser Val Gly Asp Arg Val Thr
                565                 570                 575

Ile Thr Cys Arg Ala Ser Gln Trp Ile Gly Asn Leu Leu Asp Trp Tyr
            580                 585                 590

Gln Gln Lys Pro Gly Glu Ala Pro Lys Leu Leu Ile Tyr Tyr Ala Ser
        595                 600                 605

Phe Leu Gln Ser Gly Val Pro Ser Arg Phe Ser Gly Gly Gly Phe Gly
    610                 615                 620

Thr Asp Phe Thr Leu Thr Ile Ser Ser Leu Gln Pro Glu Asp Phe Ala
625                 630                 635                 640

Thr Tyr Tyr Cys Gln Gln Ala Asn Pro Ala Pro Leu Thr Phe Gly Gln
                645                 650                 655

Gly Thr Lys Val Glu Ile Lys Arg Glu Pro Lys Ser Cys Asp Lys Thr
            660                 665                 670

His Thr Cys Pro Pro Cys Pro Ala Pro Glu Leu Leu Gly Gly Pro Ser
        675                 680                 685

Val Phe Leu Phe Pro Pro Lys Pro Lys Asp Thr Leu Met Ile Ser Arg
    690                 695                 700

Thr Pro Glu Val Thr Cys Val Val Val Asp Val Ser His Glu Asp Pro
705                 710                 715                 720

Glu Val Lys Phe Asn Trp Tyr Val Asp Gly Val Glu Val His Asn Ala
                725                 730                 735

Lys Thr Lys Pro Arg Glu Glu Gln Tyr Asn Ser Thr Tyr Arg Val Val
            740                 745                 750

Ser Val Leu Thr Val Leu His Gln Asp Trp Leu Asn Gly Lys Glu Tyr
        755                 760                 765

Lys Cys Lys Val Ser Asn Lys Ala Leu Pro Ala Pro Ile Glu Lys Thr
    770                 775                 780

Ile Ser Lys Ala Lys Gly Gln Pro Arg Glu Pro Gln Val Tyr Thr Leu
785 790 795 800

Pro Pro Ser Arg Glu Glu Met Thr Lys Asn Gln Val Ser Leu Thr Cys
805 810 815

Leu Val Lys Gly Phe Tyr Pro Ser Asp Ile Ala Val Glu Trp Glu Ser
820 825 830

Asn Gly Gln Pro Glu Asn Asn Tyr Lys Thr Thr Pro Pro Val Leu Asp
835 840 845

Ser Asp Gly Ser Phe Phe Leu Tyr Ser Lys Leu Thr Val Asp Lys Ser
850 855 860

Arg Trp Gln Gln Gly Asn Val Phe Ser Cys Ser Val Met His Glu Ala
865 870 875 880

Leu His Asn His Tyr Thr Gln Lys Ser Leu Ser Leu Ser Pro Gly Lys
885 890 895

<210> SEQ ID NO 21
<211> LENGTH: 901
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR specific binding peptides #14

<400> SEQUENCE: 21

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Arg Ala Ser Gln Trp Ile
35 40 45

Gly Pro Glu Leu Ser Trp Tyr Gln Gln Lys Pro Gly Lys Ala Pro Lys
50 55 60

Leu Leu Ile Tyr His Thr Ser Ile Leu Gln Ser Gly Val Pro Ser Arg
65 70 75 80

Phe Ser Gly Ser Gly Ser Gly Thr Asp Phe Thr Leu Thr Ile Ser Ser
85 90 95

Leu Gln Pro Glu Asp Phe Ala Thr Tyr Tyr Cys Gln Gln Tyr Met Phe
100 105 110

Gln Pro Arg Thr Phe Gly Gln Gly Thr Lys Val Glu Ile Arg Arg Glu
115 120 125

Pro Lys Ser Cys Asp Lys Thr His Thr Cys Pro Pro Cys Pro Ala Pro
130 135 140

Glu Leu Leu Gly Gly Pro Ser Val Phe Leu Phe Pro Pro Lys Pro Lys
145 150 155 160

Asp Thr Leu Met Ile Ser Arg Thr Pro Glu Val Thr Cys Val Val Val
165 170 175

Asp Val Ser His Glu Asp Pro Glu Val Lys Phe Asn Trp Tyr Val Asp
180 185 190

Gly Val Glu Val His Asn Ala Lys Thr Lys Pro Arg Glu Glu Gln Tyr
195 200 205

Asn Ser Thr Tyr Arg Val Val Ser Val Leu Thr Val Leu His Gln Asp
210 215 220

Trp Leu Asn Gly Lys Glu Tyr Lys Cys Lys Val Ser Asn Lys Ala Leu
225 230 235 240

-continued

```
Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Gly Gly Gly Gly Ser Met Gln Ile Phe Val Lys Thr Leu Thr Gly Lys
                485                 490                 495

Thr Ile Thr Leu Glu Val Glu Pro Ser Asp Thr Ile Glu Asn Val Lys
            500                 505                 510

Ala Lys Ile Gln Asp Lys Glu Gly Ile Pro Pro Asp Gln Gln Arg Leu
        515                 520                 525

Ile Phe Ala Gly Lys Gln Leu Glu Asp Gly Arg Thr Leu Ser Asp Tyr
    530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Thr Ser Leu Ser Ala Ser Val
                565                 570                 575

Gly Asp Arg Val Thr Ile Thr Cys Arg Ala Ser Gln Trp Ile Gly Asn
            580                 585                 590

Leu Leu Asp Trp Tyr Gln Gln Lys Pro Gly Glu Ala Pro Lys Leu Leu
        595                 600                 605

Ile Tyr Tyr Ala Ser Phe Leu Gln Ser Gly Val Pro Ser Arg Phe Ser
    610                 615                 620

Gly Gly Gly Phe Gly Thr Asp Phe Thr Leu Thr Ile Ser Ser Leu Gln
625                 630                 635                 640

Pro Glu Asp Phe Ala Thr Tyr Tyr Cys Gln Gln Ala Asn Pro Ala Pro
                645                 650                 655
```

-continued

```
Leu Thr Phe Gly Gln Gly Thr Lys Val Glu Ile Lys Arg Glu Pro Lys
            660                 665                 670

Ser Cys Asp Lys Thr His Thr Cys Pro Pro Cys Pro Ala Pro Glu Leu
        675                 680                 685

Leu Gly Gly Pro Ser Val Phe Leu Phe Pro Pro Lys Pro Lys Asp Thr
    690                 695                 700

Leu Met Ile Ser Arg Thr Pro Glu Val Thr Cys Val Val Val Asp Val
705                 710                 715                 720

Ser His Glu Asp Pro Glu Val Lys Phe Asn Trp Tyr Val Asp Gly Val
                725                 730                 735

Glu Val His Asn Ala Lys Thr Lys Pro Arg Glu Glu Gln Tyr Asn Ser
            740                 745                 750

Thr Tyr Arg Val Val Ser Val Leu Thr Val Leu His Gln Asp Trp Leu
        755                 760                 765

Asn Gly Lys Glu Tyr Lys Cys Lys Val Ser Asn Lys Ala Leu Pro Ala
    770                 775                 780

Pro Ile Glu Lys Thr Ile Ser Lys Ala Lys Gly Gln Pro Arg Glu Pro
785                 790                 795                 800

Gln Val Tyr Thr Leu Pro Pro Ser Arg Glu Glu Met Thr Lys Asn Gln
                805                 810                 815

Val Ser Leu Thr Cys Leu Val Lys Gly Phe Tyr Pro Ser Asp Ile Ala
            820                 825                 830

Val Glu Trp Glu Ser Asn Gly Gln Pro Glu Asn Asn Tyr Lys Thr Thr
        835                 840                 845

Pro Pro Val Leu Asp Ser Asp Gly Ser Phe Phe Leu Tyr Ser Lys Leu
    850                 855                 860

Thr Val Asp Lys Ser Arg Trp Gln Gln Gly Asn Val Phe Ser Cys Ser
865                 870                 875                 880

Val Met His Glu Ala Leu His Asn His Tyr Thr Gln Lys Ser Leu Ser
                885                 890                 895

Leu Ser Pro Gly Lys
            900


<210> SEQ ID NO 22
<211> LENGTH: 871
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #15

<400> SEQUENCE: 22

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95
```

```
Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Met Gln Ile Phe Val Lys Thr Leu Thr
    450                 455                 460

Gly Lys Thr Ile Thr Leu Glu Val Glu Pro Ser Asp Thr Ile Glu Asn
465                 470                 475                 480

Val Lys Ala Lys Ile Gln Asp Lys Glu Gly Ile Pro Pro Asp Gln Gln
                485                 490                 495

Arg Leu Ile Phe Ala Gly Lys Gln Leu Glu Asp Gly Arg Thr Leu Ser
            500                 505                 510
```

-continued

Asp Tyr Asn Ile Gln Lys Glu Ser Thr Leu His Leu Val Leu Arg Leu
        515                 520                 525

Arg Gly Gly Asp Ile Gln Met Thr Gln Ser Pro Ser Ser Leu Ser Ala
    530                 535                 540

Ser Val Gly Asp Arg Val Thr Ile Thr Cys Arg Ala Ser Gln Trp Ile
545                 550                 555                 560

Gly Ile Leu Val Asp Trp Tyr Gln Gln Lys Pro Gly Glu Ala Pro Lys
                565                 570                 575

Leu Leu Ile Tyr Tyr Ala Ser Phe Leu Gln Ser Gly Val Pro Ser Arg
            580                 585                 590

Phe Ser Gly Ser Gly Phe Gly Thr Asp Phe Thr Leu Thr Ile Ser Ser
        595                 600                 605

Leu His Pro Glu Asp Phe Ala Thr Tyr Tyr Cys Gln Gln Ala Asn Pro
    610                 615                 620

Ala Pro Leu Thr Phe Gly Gln Gly Thr Lys Val Glu Ile Lys Arg Glu
625                 630                 635                 640

Pro Lys Ser Cys Asp Lys Thr His Thr Cys Pro Pro Cys Pro Ala Pro
                645                 650                 655

Glu Leu Leu Gly Gly Pro Ser Val Phe Leu Phe Pro Pro Lys Pro Lys
            660                 665                 670

Asp Thr Leu Met Ile Ser Arg Thr Pro Glu Val Thr Cys Val Val Val
        675                 680                 685

Asp Val Ser His Glu Asp Pro Glu Val Lys Phe Asn Trp Tyr Val Asp
    690                 695                 700

Gly Val Glu Val His Asn Ala Lys Thr Lys Pro Arg Glu Glu Gln Tyr
705                 710                 715                 720

Asn Ser Thr Tyr Arg Val Val Ser Val Leu Thr Val Leu His Gln Asp
                725                 730                 735

Trp Leu Asn Gly Lys Glu Tyr Lys Cys Lys Val Ser Asn Lys Ala Leu
            740                 745                 750

Pro Ala Pro Ile Glu Lys Thr Ile Ser Lys Ala Lys Gly Gln Pro Arg
        755                 760                 765

Glu Pro Gln Val Tyr Thr Leu Pro Pro Ser Arg Glu Glu Met Thr Lys
    770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
        835                 840                 845

Cys Ser Val Met His Glu Ala Leu His Asn His Tyr Thr Gln Lys Ser
    850                 855                 860

Leu Ser Leu Ser Pro Gly Lys
865                 870

<210> SEQ ID NO 23
<211> LENGTH: 876
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR specific binding peptides #16

<400> SEQUENCE: 23

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400
```

```
Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Met Gln Ile Phe
    450                 455                 460

Val Lys Thr Leu Thr Gly Lys Thr Ile Thr Leu Glu Val Glu Pro Ser
465                 470                 475                 480

Asp Thr Ile Glu Asn Val Lys Ala Lys Ile Gln Asp Lys Glu Gly Ile
                485                 490                 495

Pro Pro Asp Gln Gln Arg Leu Ile Phe Ala Gly Lys Gln Leu Glu Asp
            500                 505                 510

Gly Arg Thr Leu Ser Asp Tyr Asn Ile Gln Lys Glu Ser Thr Leu His
        515                 520                 525

Leu Val Leu Arg Leu Arg Gly Gly Asp Ile Gln Met Thr Gln Ser Pro
    530                 535                 540

Ser Ser Leu Ser Ala Ser Val Gly Asp Arg Val Thr Ile Thr Cys Arg
545                 550                 555                 560

Ala Ser Gln Trp Ile Gly Ile Leu Val Asp Trp Tyr Gln Gln Lys Pro
                565                 570                 575

Gly Glu Ala Pro Lys Leu Leu Ile Tyr Tyr Ala Ser Phe Leu Gln Ser
            580                 585                 590

Gly Val Pro Ser Arg Phe Ser Gly Ser Gly Phe Gly Thr Asp Phe Thr
        595                 600                 605

Leu Thr Ile Ser Ser Leu His Pro Glu Asp Phe Ala Thr Tyr Tyr Cys
    610                 615                 620

Gln Gln Ala Asn Pro Ala Pro Leu Thr Phe Gly Gln Gly Thr Lys Val
625                 630                 635                 640

Glu Ile Lys Arg Glu Pro Lys Ser Cys Asp Lys Thr His Thr Cys Pro
                645                 650                 655

Pro Cys Pro Ala Pro Glu Leu Leu Gly Gly Pro Ser Val Phe Leu Phe
            660                 665                 670

Pro Pro Lys Pro Lys Asp Thr Leu Met Ile Ser Arg Thr Pro Glu Val
        675                 680                 685

Thr Cys Val Val Val Asp Val Ser His Glu Asp Pro Glu Val Lys Phe
    690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
    770                 775                 780

Glu Glu Met Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
```

```
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
    850                 855                 860

Tyr Thr Gln Lys Ser Leu Ser Leu Ser Pro Gly Lys
865                 870                 875


<210> SEQ ID NO 24
<211> LENGTH: 881
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #17

<400> SEQUENCE: 24

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285
```

-continued

```
Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Asp Ile Gln
    530                 535                 540

Met Thr Gln Ser Pro Ser Ser Leu Ser Ala Ser Val Gly Asp Arg Val
545                 550                 555                 560

Thr Ile Thr Cys Arg Ala Ser Gln Trp Ile Gly Ile Leu Val Asp Trp
                565                 570                 575

Tyr Gln Gln Lys Pro Gly Glu Ala Pro Lys Leu Leu Ile Tyr Tyr Ala
            580                 585                 590

Ser Phe Leu Gln Ser Gly Val Pro Ser Arg Phe Ser Gly Ser Gly Phe
        595                 600                 605

Gly Thr Asp Phe Thr Leu Thr Ile Ser Ser Leu His Pro Glu Asp Phe
    610                 615                 620

Ala Thr Tyr Tyr Cys Gln Gln Ala Asn Pro Ala Pro Leu Thr Phe Gly
625                 630                 635                 640

Gln Gly Thr Lys Val Glu Ile Lys Arg Glu Pro Lys Ser Cys Asp Lys
                645                 650                 655

Thr His Thr Cys Pro Pro Cys Pro Ala Pro Glu Leu Leu Gly Gly Pro
            660                 665                 670

Ser Val Phe Leu Phe Pro Pro Lys Pro Lys Asp Thr Leu Met Ile Ser
        675                 680                 685

Arg Thr Pro Glu Val Thr Cys Val Val Val Asp Val Ser His Glu Asp
    690                 695                 700

Pro Glu Val Lys Phe Asn Trp Tyr Val Asp Gly Val Glu Val His Asn
```

-continued

```
705                 710                 715                 720

Ala Lys Thr Lys Pro Arg Glu Glu Gln Tyr Asn Ser Thr Tyr Arg Val
                725                 730                 735

Val Ser Val Leu Thr Val Leu His Gln Asp Trp Leu Asn Gly Lys Glu
            740                 745                 750

Tyr Lys Cys Lys Val Ser Asn Lys Ala Leu Pro Ala Pro Ile Glu Lys
        755                 760                 765

Thr Ile Ser Lys Ala Lys Gly Gln Pro Arg Glu Pro Gln Val Tyr Thr
    770                 775                 780

Leu Pro Pro Ser Arg Glu Glu Met Thr Lys Asn Gln Val Ser Leu Thr
785                 790                 795                 800

Cys Leu Val Lys Gly Phe Tyr Pro Ser Asp Ile Ala Val Glu Trp Glu
                805                 810                 815

Ser Asn Gly Gln Pro Glu Asn Asn Tyr Lys Thr Thr Pro Pro Val Leu
            820                 825                 830

Asp Ser Asp Gly Ser Phe Phe Leu Tyr Ser Lys Leu Thr Val Asp Lys
        835                 840                 845

Ser Arg Trp Gln Gln Gly Asn Val Phe Ser Cys Ser Val Met His Glu
    850                 855                 860

Ala Leu His Asn His Tyr Thr Gln Lys Ser Leu Ser Leu Ser Pro Gly
865                 870                 875                 880

Lys


<210> SEQ ID NO 25
<211> LENGTH: 886
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #18

<400> SEQUENCE: 25

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
```

```
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Met Gln Ile Phe Val Lys Thr Leu Thr Gly
465                 470                 475                 480

Lys Thr Ile Thr Leu Glu Val Glu Pro Ser Asp Thr Ile Glu Asn Val
                485                 490                 495

Lys Ala Lys Ile Gln Asp Lys Glu Gly Ile Pro Pro Asp Gln Gln Arg
            500                 505                 510

Leu Ile Phe Ala Gly Lys Gln Leu Glu Asp Gly Arg Thr Leu Ser Asp
        515                 520                 525

Tyr Asn Ile Gln Lys Glu Ser Thr Leu His Leu Val Leu Arg Leu Arg
    530                 535                 540

Gly Gly Asp Ile Gln Met Thr Gln Ser Pro Ser Ser Leu Ser Ala Ser
545                 550                 555                 560

Val Gly Asp Arg Val Thr Ile Thr Cys Arg Ala Ser Gln Trp Ile Gly
                565                 570                 575

Ile Leu Val Asp Trp Tyr Gln Gln Lys Pro Gly Glu Ala Pro Lys Leu
            580                 585                 590
```

-continued

Leu Ile Tyr Tyr Ala Ser Phe Leu Gln Ser Gly Val Pro Ser Arg Phe
        595                 600                 605

Ser Gly Ser Gly Phe Gly Thr Asp Phe Thr Leu Thr Ile Ser Ser Leu
    610                 615                 620

His Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655

Lys Ser Cys Asp Lys Thr His Thr Cys Pro Pro Cys Pro Ala Pro Glu
            660                 665                 670

Leu Leu Gly Gly Pro Ser Val Phe Leu Phe Pro Pro Lys Pro Lys Asp
        675                 680                 685

Thr Leu Met Ile Ser Arg Thr Pro Glu Val Thr Cys Val Val Val Asp
    690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
            740                 745                 750

Leu Asn Gly Lys Glu Tyr Lys Cys Lys Val Ser Asn Lys Ala Leu Pro
        755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
                885

<210> SEQ ID NO 26
<211> LENGTH: 891
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #19

<400> SEQUENCE: 26

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile

```
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460
```

-continued

```
Ser Gly Gly Gly Gly Ser Gly Gly Gly Gly Ser Met Gln Ile Phe Val
465                 470                 475                 480

Lys Thr Leu Thr Gly Lys Thr Ile Thr Leu Glu Val Glu Pro Ser Asp
                485                 490                 495

Thr Ile Glu Asn Val Lys Ala Lys Ile Gln Asp Lys Glu Gly Ile Pro
            500                 505                 510

Pro Asp Gln Gln Arg Leu Ile Phe Ala Gly Lys Gln Leu Glu Asp Gly
        515                 520                 525

Arg Thr Leu Ser Asp Tyr Asn Ile Gln Lys Glu Ser Thr Leu His Leu
    530                 535                 540

Val Leu Arg Leu Arg Gly Gly Asp Ile Gln Met Thr Gln Ser Pro Ser
545                 550                 555                 560

Ser Leu Ser Ala Ser Val Gly Asp Arg Val Thr Ile Thr Cys Arg Ala
                565                 570                 575

Ser Gln Trp Ile Gly Ile Leu Val Asp Trp Tyr Gln Gln Lys Pro Gly
            580                 585                 590

Glu Ala Pro Lys Leu Leu Ile Tyr Tyr Ala Ser Phe Leu Gln Ser Gly
        595                 600                 605

Val Pro Ser Arg Phe Ser Gly Ser Gly Phe Gly Thr Asp Phe Thr Leu
    610                 615                 620

Thr Ile Ser Ser Leu His Pro Glu Asp Phe Ala Thr Tyr Tyr Cys Gln
625                 630                 635                 640

Gln Ala Asn Pro Ala Pro Leu Thr Phe Gly Gln Gly Thr Lys Val Glu
                645                 650                 655

Ile Lys Arg Glu Pro Lys Ser Cys Asp Lys Thr His Thr Cys Pro Pro
            660                 665                 670

Cys Pro Ala Pro Glu Leu Leu Gly Gly Pro Ser Val Phe Leu Phe Pro
        675                 680                 685

Pro Lys Pro Lys Asp Thr Leu Met Ile Ser Arg Thr Pro Glu Val Thr
    690                 695                 700

Cys Val Val Val Asp Val Ser His Glu Asp Pro Glu Val Lys Phe Asn
705                 710                 715                 720

Trp Tyr Val Asp Gly Val Glu Val His Asn Ala Lys Thr Lys Pro Arg
                725                 730                 735

Glu Glu Gln Tyr Asn Ser Thr Tyr Arg Val Val Ser Val Leu Thr Val
            740                 745                 750

Leu His Gln Asp Trp Leu Asn Gly Lys Glu Tyr Lys Cys Lys Val Ser
        755                 760                 765

Asn Lys Ala Leu Pro Ala Pro Ile Glu Lys Thr Ile Ser Lys Ala Lys
    770                 775                 780

Gly Gln Pro Arg Glu Pro Gln Val Tyr Thr Leu Pro Pro Ser Arg Glu
785                 790                 795                 800

Glu Met Thr Lys Asn Gln Val Ser Leu Thr Cys Leu Val Lys Gly Phe
                805                 810                 815

Tyr Pro Ser Asp Ile Ala Val Glu Trp Glu Ser Asn Gly Gln Pro Glu
            820                 825                 830

Asn Asn Tyr Lys Thr Thr Pro Pro Val Leu Asp Ser Asp Gly Ser Phe
        835                 840                 845

Phe Leu Tyr Ser Lys Leu Thr Val Asp Lys Ser Arg Trp Gln Gln Gly
    850                 855                 860

Asn Val Phe Ser Cys Ser Val Met His Glu Ala Leu His Asn His Tyr
865                 870                 875                 880
```

```
Thr Gln Lys Ser Leu Ser Leu Ser Pro Gly Lys
                885                 890


<210> SEQ ID NO 27
<211> LENGTH: 896
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #20

<400> SEQUENCE: 27

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335
```

-continued

```
Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Met Gln Ile Phe Val Lys Thr Leu Thr Gly Lys Thr Ile Thr Leu Glu
                485                 490                 495

Val Glu Pro Ser Asp Thr Ile Glu Asn Val Lys Ala Lys Ile Gln Asp
            500                 505                 510

Lys Glu Gly Ile Pro Pro Asp Gln Gln Arg Leu Ile Phe Ala Gly Lys
        515                 520                 525

Gln Leu Glu Asp Gly Arg Thr Leu Ser Asp Tyr Asn Ile Gln Lys Glu
    530                 535                 540

Ser Thr Leu His Leu Val Leu Arg Leu Arg Gly Gly Asp Ile Gln Met
545                 550                 555                 560

Thr Gln Ser Pro Ser Ser Leu Ser Ala Ser Val Gly Asp Arg Val Thr
                565                 570                 575

Ile Thr Cys Arg Ala Ser Gln Trp Ile Gly Ile Leu Val Asp Trp Tyr
            580                 585                 590

Gln Gln Lys Pro Gly Glu Ala Pro Lys Leu Leu Ile Tyr Tyr Ala Ser
        595                 600                 605

Phe Leu Gln Ser Gly Val Pro Ser Arg Phe Ser Gly Ser Gly Phe Gly
    610                 615                 620

Thr Asp Phe Thr Leu Thr Ile Ser Ser Leu His Pro Glu Asp Phe Ala
625                 630                 635                 640

Thr Tyr Tyr Cys Gln Gln Ala Asn Pro Ala Pro Leu Thr Phe Gly Gln
                645                 650                 655

Gly Thr Lys Val Glu Ile Lys Arg Glu Pro Lys Ser Cys Asp Lys Thr
            660                 665                 670

His Thr Cys Pro Pro Cys Pro Ala Pro Glu Leu Leu Gly Gly Pro Ser
        675                 680                 685

Val Phe Leu Phe Pro Pro Lys Pro Lys Asp Thr Leu Met Ile Ser Arg
    690                 695                 700

Thr Pro Glu Val Thr Cys Val Val Val Asp Val Ser His Glu Asp Pro
705                 710                 715                 720

Glu Val Lys Phe Asn Trp Tyr Val Asp Gly Val Glu Val His Asn Ala
                725                 730                 735

Lys Thr Lys Pro Arg Glu Glu Gln Tyr Asn Ser Thr Tyr Arg Val Val
            740                 745                 750
```

-continued

```
Ser Val Leu Thr Val Leu His Gln Asp Trp Leu Asn Gly Lys Glu Tyr
        755                 760                 765

Lys Cys Lys Val Ser Asn Lys Ala Leu Pro Ala Pro Ile Glu Lys Thr
    770                 775                 780

Ile Ser Lys Ala Lys Gly Gln Pro Arg Glu Pro Gln Val Tyr Thr Leu
785                 790                 795                 800

Pro Pro Ser Arg Glu Glu Met Thr Lys Asn Gln Val Ser Leu Thr Cys
                805                 810                 815

Leu Val Lys Gly Phe Tyr Pro Ser Asp Ile Ala Val Glu Trp Glu Ser
            820                 825                 830

Asn Gly Gln Pro Glu Asn Asn Tyr Lys Thr Thr Pro Pro Val Leu Asp
        835                 840                 845

Ser Asp Gly Ser Phe Phe Leu Tyr Ser Lys Leu Thr Val Asp Lys Ser
    850                 855                 860

Arg Trp Gln Gln Gly Asn Val Phe Ser Cys Ser Val Met His Glu Ala
865                 870                 875                 880

Leu His Asn His Tyr Thr Gln Lys Ser Leu Ser Leu Ser Pro Gly Lys
                885                 890                 895


<210> SEQ ID NO 28
<211> LENGTH: 901
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #21

<400> SEQUENCE: 28

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205
```

-continued

```
Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Gly Gly Gly Gly Ser Met Gln Ile Phe Val Lys Thr Leu Thr Gly Lys
                485                 490                 495

Thr Ile Thr Leu Glu Val Glu Pro Ser Asp Thr Ile Glu Asn Val Lys
            500                 505                 510

Ala Lys Ile Gln Asp Lys Glu Gly Ile Pro Pro Asp Gln Gln Arg Leu
        515                 520                 525

Ile Phe Ala Gly Lys Gln Leu Glu Asp Gly Arg Thr Leu Ser Asp Tyr
    530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Ser Ser Leu Ser Ala Ser Val
                565                 570                 575

Gly Asp Arg Val Thr Ile Thr Cys Arg Ala Ser Gln Trp Ile Gly Ile
            580                 585                 590

Leu Val Asp Trp Tyr Gln Gln Lys Pro Gly Glu Ala Pro Lys Leu Leu
        595                 600                 605

Ile Tyr Tyr Ala Ser Phe Leu Gln Ser Gly Val Pro Ser Arg Phe Ser
    610                 615                 620
```

-continued

Gly Ser Gly Phe Gly Thr Asp Phe Thr Leu Thr Ile Ser Ser Leu His
625 630 635 640

Pro Glu Asp Phe Ala Thr Tyr Tyr Cys Gln Gln Ala Asn Pro Ala Pro
645 650 655

Leu Thr Phe Gly Gln Gly Thr Lys Val Glu Ile Lys Arg Glu Pro Lys
660 665 670

Ser Cys Asp Lys Thr His Thr Cys Pro Pro Cys Pro Ala Pro Glu Leu
675 680 685

Leu Gly Gly Pro Ser Val Phe Leu Phe Pro Pro Lys Pro Lys Asp Thr
690 695 700

Leu Met Ile Ser Arg Thr Pro Glu Val Thr Cys Val Val Val Asp Val
705 710 715 720

Ser His Glu Asp Pro Glu Val Lys Phe Asn Trp Tyr Val Asp Gly Val
725 730 735

Glu Val His Asn Ala Lys Thr Lys Pro Arg Glu Glu Gln Tyr Asn Ser
740 745 750

Thr Tyr Arg Val Val Ser Val Leu Thr Val Leu His Gln Asp Trp Leu
755 760 765

Asn Gly Lys Glu Tyr Lys Cys Lys Val Ser Asn Lys Ala Leu Pro Ala
770 775 780

Pro Ile Glu Lys Thr Ile Ser Lys Ala Lys Gly Gln Pro Arg Glu Pro
785 790 795 800

Gln Val Tyr Thr Leu Pro Pro Ser Arg Glu Glu Met Thr Lys Asn Gln
805 810 815

Val Ser Leu Thr Cys Leu Val Lys Gly Phe Tyr Pro Ser Asp Ile Ala
820 825 830

Val Glu Trp Glu Ser Asn Gly Gln Pro Glu Asn Asn Tyr Lys Thr Thr
835 840 845

Pro Pro Val Leu Asp Ser Asp Gly Ser Phe Phe Leu Tyr Ser Lys Leu
850 855 860

Thr Val Asp Lys Ser Arg Trp Gln Gln Gly Asn Val Phe Ser Cys Ser
865 870 875 880

Val Met His Glu Ala Leu His Asn His Tyr Thr Gln Lys Ser Leu Ser
885 890 895

Leu Ser Pro Gly Lys
900

<210> SEQ ID NO 29
<211> LENGTH: 871
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR specific binding peptides #22

<400> SEQUENCE: 29

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Arg Ala Ser Gln Lys Ile
35 40 45

Phe Asn Gly Leu Ser Trp Tyr Gln Gln Lys Pro Gly Lys Ala Pro Lys
50 55 60

-continued

```
Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Met Gln Ile Phe Val Lys Thr Leu Thr
    450                 455                 460

Gly Lys Thr Ile Thr Leu Glu Val Glu Pro Ser Asp Thr Ile Glu Asn
465                 470                 475                 480
```

```
Val Lys Ala Lys Ile Gln Asp Lys Glu Gly Ile Pro Pro Asp Gln Gln
                485                 490                 495

Arg Leu Ile Phe Ala Gly Lys Gln Leu Glu Asp Gly Arg Thr Leu Ser
            500                 505                 510

Asp Tyr Asn Ile Gln Lys Glu Ser Thr Leu His Leu Val Leu Arg Leu
        515                 520                 525

Arg Gly Gly Asp Ile Gln Met Thr Gln Ser Pro Thr Ser Leu Ser Ala
    530                 535                 540

Ser Val Gly Asp Arg Val Thr Ile Thr Cys Arg Ala Ser Gln Trp Ile
545                 550                 555                 560

Gly Asn Leu Leu Asp Trp Tyr Gln Gln Lys Pro Gly Glu Ala Pro Lys
                565                 570                 575

Leu Leu Ile Tyr Tyr Ala Ser Phe Leu Gln Ser Gly Val Pro Ser Arg
            580                 585                 590

Phe Ser Gly Gly Gly Phe Gly Thr Asp Phe Thr Leu Thr Ile Ser Ser
        595                 600                 605

Leu Gln Pro Glu Asp Phe Ala Thr Tyr Tyr Cys Gln Gln Ala Asn Pro
    610                 615                 620

Ala Pro Leu Thr Phe Gly Gln Gly Thr Lys Val Glu Ile Lys Arg Glu
625                 630                 635                 640

Pro Lys Ser Cys Asp Lys Thr His Thr Cys Pro Pro Cys Pro Ala Pro
                645                 650                 655

Glu Leu Leu Gly Gly Pro Ser Val Phe Leu Phe Pro Pro Lys Pro Lys
            660                 665                 670

Asp Thr Leu Met Ile Ser Arg Thr Pro Glu Val Thr Cys Val Val Val
        675                 680                 685

Asp Val Ser His Glu Asp Pro Glu Val Lys Phe Asn Trp Tyr Val Asp
    690                 695                 700

Gly Val Glu Val His Asn Ala Lys Thr Lys Pro Arg Glu Glu Gln Tyr
705                 710                 715                 720

Asn Ser Thr Tyr Arg Val Val Ser Val Leu Thr Val Leu His Gln Asp
                725                 730                 735

Trp Leu Asn Gly Lys Glu Tyr Lys Cys Lys Val Ser Asn Lys Ala Leu
            740                 745                 750

Pro Ala Pro Ile Glu Lys Thr Ile Ser Lys Ala Lys Gly Gln Pro Arg
        755                 760                 765

Glu Pro Gln Val Tyr Thr Leu Pro Pro Ser Arg Glu Glu Met Thr Lys
    770                 775                 780

Asn Gln Val Ser Leu Thr Cys Leu Val Lys Gly Phe Tyr Pro Ser Asp
785                 790                 795                 800

Ile Ala Val Glu Trp Glu Ser Asn Gly Gln Pro Glu Asn Asn Tyr Lys
                805                 810                 815

Thr Thr Pro Pro Val Leu Asp Ser Asp Gly Ser Phe Phe Leu Tyr Ser
            820                 825                 830

Lys Leu Thr Val Asp Lys Ser Arg Trp Gln Gln Gly Asn Val Phe Ser
        835                 840                 845

Cys Ser Val Met His Glu Ala Leu His Asn His Tyr Thr Gln Lys Ser
    850                 855                 860

Leu Ser Leu Ser Pro Gly Lys
865                 870
```

<210> SEQ ID NO 30
<211> LENGTH: 876
<212> TYPE: PRT

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #23

<400> SEQUENCE: 30

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365
```

```
Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Met Gln Ile Phe
    450                 455                 460

Val Lys Thr Leu Thr Gly Lys Thr Ile Thr Leu Glu Val Glu Pro Ser
465                 470                 475                 480

Asp Thr Ile Glu Asn Val Lys Ala Lys Ile Gln Asp Lys Glu Gly Ile
                485                 490                 495

Pro Pro Asp Gln Gln Arg Leu Ile Phe Ala Gly Lys Gln Leu Glu Asp
            500                 505                 510

Gly Arg Thr Leu Ser Asp Tyr Asn Ile Gln Lys Glu Ser Thr Leu His
        515                 520                 525

Leu Val Leu Arg Leu Arg Gly Gly Asp Ile Gln Met Thr Gln Ser Pro
    530                 535                 540

Thr Ser Leu Ser Ala Ser Val Gly Asp Arg Val Thr Ile Thr Cys Arg
545                 550                 555                 560

Ala Ser Gln Trp Ile Gly Asn Leu Leu Asp Trp Tyr Gln Gln Lys Pro
                565                 570                 575

Gly Glu Ala Pro Lys Leu Leu Ile Tyr Tyr Ala Ser Phe Leu Gln Ser
            580                 585                 590

Gly Val Pro Ser Arg Phe Ser Gly Gly Gly Phe Gly Thr Asp Phe Thr
        595                 600                 605

Leu Thr Ile Ser Ser Leu Gln Pro Glu Asp Phe Ala Thr Tyr Tyr Cys
    610                 615                 620

Gln Gln Ala Asn Pro Ala Pro Leu Thr Phe Gly Gln Gly Thr Lys Val
625                 630                 635                 640

Glu Ile Lys Arg Glu Pro Lys Ser Cys Asp Lys Thr His Thr Cys Pro
                645                 650                 655

Pro Cys Pro Ala Pro Glu Leu Leu Gly Gly Pro Ser Val Phe Leu Phe
            660                 665                 670

Pro Pro Lys Pro Lys Asp Thr Leu Met Ile Ser Arg Thr Pro Glu Val
        675                 680                 685

Thr Cys Val Val Val Asp Val Ser His Glu Asp Pro Glu Val Lys Phe
    690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
    770                 775                 780

Glu Glu Met Thr Lys Asn Gln Val Ser Leu Thr Cys Leu Val Lys Gly
```

-continued

```
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
    850                 855                 860

Tyr Thr Gln Lys Ser Leu Ser Leu Ser Pro Gly Lys
865                 870                 875


<210> SEQ ID NO 31
<211> LENGTH: 881
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #24

<400> SEQUENCE: 31

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255
```

-continued

```
Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Asp Ile Gln
    530                 535                 540

Met Thr Gln Ser Pro Thr Ser Leu Ser Ala Ser Val Gly Asp Arg Val
545                 550                 555                 560

Thr Ile Thr Cys Arg Ala Ser Gln Trp Ile Gly Asn Leu Leu Asp Trp
                565                 570                 575

Tyr Gln Gln Lys Pro Gly Glu Ala Pro Lys Leu Leu Ile Tyr Tyr Ala
            580                 585                 590

Ser Phe Leu Gln Ser Gly Val Pro Ser Arg Phe Ser Gly Gly Gly Phe
        595                 600                 605

Gly Thr Asp Phe Thr Leu Thr Ile Ser Ser Leu Gln Pro Glu Asp Phe
    610                 615                 620

Ala Thr Tyr Tyr Cys Gln Gln Ala Asn Pro Ala Pro Leu Thr Phe Gly
625                 630                 635                 640

Gln Gly Thr Lys Val Glu Ile Lys Arg Glu Pro Lys Ser Cys Asp Lys
                645                 650                 655

Thr His Thr Cys Pro Pro Cys Pro Ala Pro Glu Leu Leu Gly Gly Pro
            660                 665                 670

Ser Val Phe Leu Phe Pro Pro Lys Pro Lys Asp Thr Leu Met Ile Ser
```

```
        675                 680                 685

Arg Thr Pro Glu Val Thr Cys Val Val Val Asp Val Ser His Glu Asp
    690                 695                 700

Pro Glu Val Lys Phe Asn Trp Tyr Val Asp Gly Val Glu Val His Asn
705                 710                 715                 720

Ala Lys Thr Lys Pro Arg Glu Glu Gln Tyr Asn Ser Thr Tyr Arg Val
                725                 730                 735

Val Ser Val Leu Thr Val Leu His Gln Asp Trp Leu Asn Gly Lys Glu
            740                 745                 750

Tyr Lys Cys Lys Val Ser Asn Lys Ala Leu Pro Ala Pro Ile Glu Lys
        755                 760                 765

Thr Ile Ser Lys Ala Lys Gly Gln Pro Arg Glu Pro Gln Val Tyr Thr
    770                 775                 780

Leu Pro Pro Ser Arg Glu Glu Met Thr Lys Asn Gln Val Ser Leu Thr
785                 790                 795                 800

Cys Leu Val Lys Gly Phe Tyr Pro Ser Asp Ile Ala Val Glu Trp Glu
                805                 810                 815

Ser Asn Gly Gln Pro Glu Asn Asn Tyr Lys Thr Thr Pro Pro Val Leu
            820                 825                 830

Asp Ser Asp Gly Ser Phe Phe Leu Tyr Ser Lys Leu Thr Val Asp Lys
        835                 840                 845

Ser Arg Trp Gln Gln Gly Asn Val Phe Ser Cys Ser Val Met His Glu
    850                 855                 860

Ala Leu His Asn His Tyr Thr Gln Lys Ser Leu Ser Leu Ser Pro Gly
865                 870                 875                 880

Lys


<210> SEQ ID NO 32
<211> LENGTH: 886
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #25

<400> SEQUENCE: 32

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
```

-continued

```
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Met Gln Ile Phe Val Lys Thr Leu Thr Gly
465                 470                 475                 480

Lys Thr Ile Thr Leu Glu Val Glu Pro Ser Asp Thr Ile Glu Asn Val
                485                 490                 495

Lys Ala Lys Ile Gln Asp Lys Glu Gly Ile Pro Pro Asp Gln Gln Arg
            500                 505                 510

Leu Ile Phe Ala Gly Lys Gln Leu Glu Asp Gly Arg Thr Leu Ser Asp
        515                 520                 525

Tyr Asn Ile Gln Lys Glu Ser Thr Leu His Leu Val Leu Arg Leu Arg
    530                 535                 540

Gly Gly Asp Ile Gln Met Thr Gln Ser Pro Thr Ser Leu Ser Ala Ser
545                 550                 555                 560
```

```
Val Gly Asp Arg Val Thr Ile Thr Cys Arg Ala Ser Gln Trp Ile Gly
                565                 570                 575

Asn Leu Leu Asp Trp Tyr Gln Gln Lys Pro Gly Glu Ala Pro Lys Leu
            580                 585                 590

Leu Ile Tyr Tyr Ala Ser Phe Leu Gln Ser Gly Val Pro Ser Arg Phe
        595                 600                 605

Ser Gly Gly Gly Phe Gly Thr Asp Phe Thr Leu Thr Ile Ser Ser Leu
    610                 615                 620

Gln Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655

Lys Ser Cys Asp Lys Thr His Thr Cys Pro Pro Cys Pro Ala Pro Glu
            660                 665                 670

Leu Leu Gly Gly Pro Ser Val Phe Leu Phe Pro Pro Lys Pro Lys Asp
        675                 680                 685

Thr Leu Met Ile Ser Arg Thr Pro Glu Val Thr Cys Val Val Val Asp
    690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
            740                 745                 750

Leu Asn Gly Lys Glu Tyr Lys Cys Lys Val Ser Asn Lys Ala Leu Pro
        755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
                885
```

<210> SEQ ID NO 33
<211> LENGTH: 891
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #26

<400> SEQUENCE: 33

```
Met Gly Trp Ser Cys Ile Ile Leu Phe Leu Val Ala Thr Ala Thr Gly
```

-continued

```
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430
```

```
Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Met Gln Ile Phe Val
465                 470                 475                 480

Lys Thr Leu Thr Gly Lys Thr Ile Thr Leu Glu Val Glu Pro Ser Asp
                485                 490                 495

Thr Ile Glu Asn Val Lys Ala Lys Ile Gln Asp Lys Glu Gly Ile Pro
            500                 505                 510

Pro Asp Gln Gln Arg Leu Ile Phe Ala Gly Lys Gln Leu Glu Asp Gly
        515                 520                 525

Arg Thr Leu Ser Asp Tyr Asn Ile Gln Lys Glu Ser Thr Leu His Leu
    530                 535                 540

Val Leu Arg Leu Arg Gly Gly Asp Ile Gln Met Thr Gln Ser Pro Thr
545                 550                 555                 560

Ser Leu Ser Ala Ser Val Gly Asp Arg Val Thr Ile Thr Cys Arg Ala
                565                 570                 575

Ser Gln Trp Ile Gly Asn Leu Leu Asp Trp Tyr Gln Gln Lys Pro Gly
            580                 585                 590

Glu Ala Pro Lys Leu Leu Ile Tyr Tyr Ala Ser Phe Leu Gln Ser Gly
        595                 600                 605

Val Pro Ser Arg Phe Ser Gly Gly Gly Phe Gly Thr Asp Phe Thr Leu
    610                 615                 620

Thr Ile Ser Ser Leu Gln Pro Glu Asp Phe Ala Thr Tyr Tyr Cys Gln
625                 630                 635                 640

Gln Ala Asn Pro Ala Pro Leu Thr Phe Gly Gln Gly Thr Lys Val Glu
                645                 650                 655

Ile Lys Arg Glu Pro Lys Ser Cys Asp Lys Thr His Thr Cys Pro Pro
            660                 665                 670

Cys Pro Ala Pro Glu Leu Leu Gly Gly Pro Ser Val Phe Leu Phe Pro
        675                 680                 685

Pro Lys Pro Lys Asp Thr Leu Met Ile Ser Arg Thr Pro Glu Val Thr
    690                 695                 700

Cys Val Val Val Asp Val Ser His Glu Asp Pro Glu Val Lys Phe Asn
705                 710                 715                 720

Trp Tyr Val Asp Gly Val Glu Val His Asn Ala Lys Thr Lys Pro Arg
                725                 730                 735

Glu Glu Gln Tyr Asn Ser Thr Tyr Arg Val Val Ser Val Leu Thr Val
            740                 745                 750

Leu His Gln Asp Trp Leu Asn Gly Lys Glu Tyr Lys Cys Lys Val Ser
        755                 760                 765

Asn Lys Ala Leu Pro Ala Pro Ile Glu Lys Thr Ile Ser Lys Ala Lys
    770                 775                 780

Gly Gln Pro Arg Glu Pro Gln Val Tyr Thr Leu Pro Pro Ser Arg Glu
785                 790                 795                 800

Glu Met Thr Lys Asn Gln Val Ser Leu Thr Cys Leu Val Lys Gly Phe
                805                 810                 815

Tyr Pro Ser Asp Ile Ala Val Glu Trp Glu Ser Asn Gly Gln Pro Glu
            820                 825                 830

Asn Asn Tyr Lys Thr Thr Pro Pro Val Leu Asp Ser Asp Gly Ser Phe
        835                 840                 845
```

-continued

```
Phe Leu Tyr Ser Lys Leu Thr Val Asp Lys Ser Arg Trp Gln Gln Gly
    850                 855                 860

Asn Val Phe Ser Cys Ser Val Met His Glu Ala Leu His Asn His Tyr
865                 870                 875                 880

Thr Gln Lys Ser Leu Ser Leu Ser Pro Gly Lys
                885                 890


<210> SEQ ID NO 34
<211> LENGTH: 896
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #27

<400> SEQUENCE: 34

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300
```

```
Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Met Gln Ile Phe Val Lys Thr Leu Thr Gly Lys Thr Ile Thr Leu Glu
                485                 490                 495

Val Glu Pro Ser Asp Thr Ile Glu Asn Val Lys Ala Lys Ile Gln Asp
            500                 505                 510

Lys Glu Gly Ile Pro Pro Asp Gln Gln Arg Leu Ile Phe Ala Gly Lys
        515                 520                 525

Gln Leu Glu Asp Gly Arg Thr Leu Ser Asp Tyr Asn Ile Gln Lys Glu
    530                 535                 540

Ser Thr Leu His Leu Val Leu Arg Leu Arg Gly Gly Asp Ile Gln Met
545                 550                 555                 560

Thr Gln Ser Pro Thr Ser Leu Ser Ala Ser Val Gly Asp Arg Val Thr
                565                 570                 575

Ile Thr Cys Arg Ala Ser Gln Trp Ile Gly Asn Leu Leu Asp Trp Tyr
            580                 585                 590

Gln Gln Lys Pro Gly Glu Ala Pro Lys Leu Leu Ile Tyr Tyr Ala Ser
        595                 600                 605

Phe Leu Gln Ser Gly Val Pro Ser Arg Phe Ser Gly Gly Gly Phe Gly
    610                 615                 620

Thr Asp Phe Thr Leu Thr Ile Ser Ser Leu Gln Pro Glu Asp Phe Ala
625                 630                 635                 640

Thr Tyr Tyr Cys Gln Gln Ala Asn Pro Ala Pro Leu Thr Phe Gly Gln
                645                 650                 655

Gly Thr Lys Val Glu Ile Lys Arg Glu Pro Lys Ser Cys Asp Lys Thr
            660                 665                 670

His Thr Cys Pro Pro Cys Pro Ala Pro Glu Leu Leu Gly Gly Pro Ser
        675                 680                 685

Val Phe Leu Phe Pro Pro Lys Pro Lys Asp Thr Leu Met Ile Ser Arg
    690                 695                 700

Thr Pro Glu Val Thr Cys Val Val Val Asp Val Ser His Glu Asp Pro
705                 710                 715                 720
```

```
Glu Val Lys Phe Asn Trp Tyr Val Asp Gly Val Glu Val His Asn Ala
                725                 730                 735

Lys Thr Lys Pro Arg Glu Glu Gln Tyr Asn Ser Thr Tyr Arg Val Val
            740                 745                 750

Ser Val Leu Thr Val Leu His Gln Asp Trp Leu Asn Gly Lys Glu Tyr
        755                 760                 765

Lys Cys Lys Val Ser Asn Lys Ala Leu Pro Ala Pro Ile Glu Lys Thr
    770                 775                 780

Ile Ser Lys Ala Lys Gly Gln Pro Arg Glu Pro Gln Val Tyr Thr Leu
785                 790                 795                 800

Pro Pro Ser Arg Glu Glu Met Thr Lys Asn Gln Val Ser Leu Thr Cys
                805                 810                 815

Leu Val Lys Gly Phe Tyr Pro Ser Asp Ile Ala Val Glu Trp Glu Ser
            820                 825                 830

Asn Gly Gln Pro Glu Asn Asn Tyr Lys Thr Thr Pro Pro Val Leu Asp
        835                 840                 845

Ser Asp Gly Ser Phe Phe Leu Tyr Ser Lys Leu Thr Val Asp Lys Ser
    850                 855                 860

Arg Trp Gln Gln Gly Asn Val Phe Ser Cys Ser Val Met His Glu Ala
865                 870                 875                 880

Leu His Asn His Tyr Thr Gln Lys Ser Leu Ser Leu Ser Pro Gly Lys
                885                 890                 895


<210> SEQ ID NO 35
<211> LENGTH: 901
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #28

<400> SEQUENCE: 35

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175
```

-continued

```
Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Gly Gly Gly Gly Ser Met Gln Ile Phe Val Lys Thr Leu Thr Gly Lys
                485                 490                 495

Thr Ile Thr Leu Glu Val Glu Pro Ser Asp Thr Ile Glu Asn Val Lys
            500                 505                 510

Ala Lys Ile Gln Asp Lys Glu Gly Ile Pro Pro Asp Gln Gln Arg Leu
        515                 520                 525

Ile Phe Ala Gly Lys Gln Leu Glu Asp Gly Arg Thr Leu Ser Asp Tyr
    530                 535                 540

Asn Ile Gln Lys Glu Ser Thr Leu His Leu Val Leu Arg Leu Arg Gly
545                 550                 555                 560

Gly Asp Ile Gln Met Thr Gln Ser Pro Thr Ser Leu Ser Ala Ser Val
                565                 570                 575

Gly Asp Arg Val Thr Ile Thr Cys Arg Ala Ser Gln Trp Ile Gly Asn
            580                 585                 590
```

-continued

```
Leu Leu Asp Trp Tyr Gln Gln Lys Pro Gly Glu Ala Pro Lys Leu Leu
        595                 600                 605

Ile Tyr Tyr Ala Ser Phe Leu Gln Ser Gly Val Pro Ser Arg Phe Ser
    610                 615                 620

Gly Gly Gly Phe Gly Thr Asp Phe Thr Leu Thr Ile Ser Ser Leu Gln
625                 630                 635                 640

Pro Glu Asp Phe Ala Thr Tyr Tyr Cys Gln Gln Ala Asn Pro Ala Pro
                645                 650                 655

Leu Thr Phe Gly Gln Gly Thr Lys Val Glu Ile Lys Arg Glu Pro Lys
            660                 665                 670

Ser Cys Asp Lys Thr His Thr Cys Pro Pro Cys Pro Ala Pro Glu Leu
        675                 680                 685

Leu Gly Gly Pro Ser Val Phe Leu Phe Pro Pro Lys Pro Lys Asp Thr
    690                 695                 700

Leu Met Ile Ser Arg Thr Pro Glu Val Thr Cys Val Val Val Asp Val
705                 710                 715                 720

Ser His Glu Asp Pro Glu Val Lys Phe Asn Trp Tyr Val Asp Gly Val
                725                 730                 735

Glu Val His Asn Ala Lys Thr Lys Pro Arg Glu Glu Gln Tyr Asn Ser
            740                 745                 750

Thr Tyr Arg Val Val Ser Val Leu Thr Val Leu His Gln Asp Trp Leu
        755                 760                 765

Asn Gly Lys Glu Tyr Lys Cys Lys Val Ser Asn Lys Ala Leu Pro Ala
    770                 775                 780

Pro Ile Glu Lys Thr Ile Ser Lys Ala Lys Gly Gln Pro Arg Glu Pro
785                 790                 795                 800

Gln Val Tyr Thr Leu Pro Pro Ser Arg Glu Glu Met Thr Lys Asn Gln
                805                 810                 815

Val Ser Leu Thr Cys Leu Val Lys Gly Phe Tyr Pro Ser Asp Ile Ala
            820                 825                 830

Val Glu Trp Glu Ser Asn Gly Gln Pro Glu Asn Asn Tyr Lys Thr Thr
        835                 840                 845

Pro Pro Val Leu Asp Ser Asp Gly Ser Phe Phe Leu Tyr Ser Lys Leu
    850                 855                 860

Thr Val Asp Lys Ser Arg Trp Gln Gln Gly Asn Val Phe Ser Cys Ser
865                 870                 875                 880

Val Met His Glu Ala Leu His Asn His Tyr Thr Gln Lys Ser Leu Ser
                885                 890                 895

Leu Ser Pro Gly Lys
            900


<210> SEQ ID NO 36
<211> LENGTH: 880
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #29

<400> SEQUENCE: 36

Gly Trp Ser Cys Ile Ile Leu Phe Leu Val Ala Thr Ala Thr Gly Val
1               5                   10                  15

His Ser Asp Ile Gln Met Thr Gln Ser Pro Ser Ser Leu Ser Ala Ser
            20                  25                  30
```

```
Val Gly Asp Arg Val Thr Ile Thr Cys Arg Ala Ser Gln Lys Ile Phe
        35                  40                  45

Asn Gly Leu Ser Trp Tyr Gln Gln Lys Pro Gly Lys Ala Pro Lys Leu
    50                  55                  60

Leu Ile Tyr His Ser Ser Thr Leu Gln Ser Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys Gln Gln Val Leu Leu Tyr
            100                 105                 110

Pro Tyr Thr Phe Gly Gln Gly Thr Lys Val Glu Ile Lys Arg Glu Pro
        115                 120                 125

Lys Ser Cys Asp Lys Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys Met Gln Ile Phe Val Lys Thr Leu Thr Gly
        355                 360                 365

Lys Thr Ile Thr Leu Glu Val Glu Pro Ser Asp Thr Ile Glu Asn Val
    370                 375                 380

Lys Ala Lys Ile Gln Asp Lys Glu Gly Ile Pro Pro Asp Gln Gln Arg
385                 390                 395                 400

Leu Ile Phe Ala Gly Lys Gln Leu Glu Asp Gly Arg Thr Leu Ser Asp
                405                 410                 415

Tyr Asn Ile Gln Lys Glu Ser Thr Leu His Leu Val Leu Arg Leu Arg
            420                 425                 430

Gly Gly Gly Gly Gly Gly Ser Gly Gly Gly Gly Ser Gly Gly Gly Gly
        435                 440                 445
```

-continued

```
Ser Gly Gly Gly Gly Ser Gly Gly Gly Gly Ser Gly Gly Gly Gly Ser
    450                 455                 460

Met Gln Ile Phe Val Lys Thr Leu Thr Gly Lys Thr Ile Thr Leu Glu
465                 470                 475                 480

Val Glu Pro Ser Asp Thr Ile Glu Asn Val Lys Ala Lys Ile Gln Asp
                485                 490                 495

Lys Glu Gly Ile Pro Pro Asp Gln Gln Arg Leu Ile Phe Ala Gly Lys
            500                 505                 510

Gln Leu Glu Asp Gly Arg Thr Leu Ser Asp Tyr Asn Ile Gln Lys Glu
        515                 520                 525

Ser Thr Leu His Leu Val Leu Arg Leu Arg Gly Gly Asp Ile Gln Met
    530                 535                 540

Thr Gln Ser Pro Thr Ser Leu Ser Ala Ser Val Gly Asp Arg Val Thr
545                 550                 555                 560

Ile Thr Cys Arg Ala Ser Gln Trp Ile Gly Asn Leu Leu Asp Trp Tyr
                565                 570                 575

Gln Gln Lys Pro Gly Glu Ala Pro Lys Leu Leu Ile Tyr Tyr Ala Ser
            580                 585                 590

Phe Leu Gln Ser Gly Val Pro Ser Arg Phe Ser Gly Gly Gly Phe Gly
        595                 600                 605

Thr Asp Phe Thr Leu Thr Ile Ser Ser Leu Gln Pro Glu Asp Phe Ala
    610                 615                 620

Thr Tyr Tyr Cys Gln Gln Ala Asn Pro Ala Pro Leu Thr Phe Gly Gln
625                 630                 635                 640

Gly Thr Lys Val Glu Ile Lys Arg Glu Pro Lys Ser Cys Asp Lys Thr
                645                 650                 655

His Thr Cys Pro Pro Cys Pro Ala Pro Glu Leu Leu Gly Gly Pro Ser
            660                 665                 670

Val Phe Leu Phe Pro Pro Lys Pro Lys Asp Thr Leu Met Ile Ser Arg
        675                 680                 685

Thr Pro Glu Val Thr Cys Val Val Val Asp Val Ser His Glu Asp Pro
    690                 695                 700

Glu Val Lys Phe Asn Trp Tyr Val Asp Gly Val Glu Val His Asn Ala
705                 710                 715                 720

Lys Thr Lys Pro Arg Glu Glu Gln Tyr Asn Ser Thr Tyr Arg Val Val
                725                 730                 735

Ser Val Leu Thr Val Leu His Gln Asp Trp Leu Asn Gly Lys Glu Tyr
            740                 745                 750

Lys Cys Lys Val Ser Asn Lys Ala Leu Pro Ala Pro Ile Glu Lys Thr
        755                 760                 765

Ile Ser Lys Ala Lys Gly Gln Pro Arg Glu Pro Gln Val Tyr Thr Leu
    770                 775                 780

Pro Pro Ser Arg Glu Glu Met Thr Lys Asn Gln Val Ser Leu Thr Cys
785                 790                 795                 800

Leu Val Lys Gly Phe Tyr Pro Ser Asp Ile Ala Val Glu Trp Glu Ser
                805                 810                 815

Asn Gly Gln Pro Glu Asn Asn Tyr Lys Thr Thr Pro Pro Val Leu Asp
            820                 825                 830

Ser Asp Gly Ser Phe Phe Leu Tyr Ser Lys Leu Thr Val Asp Lys Ser
        835                 840                 845

Arg Trp Gln Gln Gly Asn Val Phe Ser Cys Ser Val Met His Glu Ala
    850                 855                 860

Leu His Asn His Tyr Thr Gln Lys Ser Leu Ser Leu Ser Pro Gly Lys
```

865 870 875 880

<210> SEQ ID NO 37
<211> LENGTH: 777
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
specific binding peptides #30

<400> SEQUENCE: 37

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335
```

```
Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Asp Ile Gln Met Thr Gln Ser Pro Thr Ser Leu
        435                 440                 445

Ser Ala Ser Val Gly Asp Arg Val Thr Ile Thr Cys Arg Ala Ser Gln
    450                 455                 460

Trp Ile Gly Asn Leu Leu Asp Trp Tyr Gln Gln Lys Pro Gly Glu Ala
465                 470                 475                 480

Pro Lys Leu Leu Ile Tyr Tyr Ala Ser Phe Leu Gln Ser Gly Val Pro
                485                 490                 495

Ser Arg Phe Ser Gly Gly Gly Phe Gly Thr Asp Phe Thr Leu Thr Ile
            500                 505                 510

Ser Ser Leu Gln Pro Glu Asp Phe Ala Thr Tyr Tyr Cys Gln Gln Ala
        515                 520                 525

Asn Pro Ala Pro Leu Thr Phe Gly Gln Gly Thr Lys Val Glu Ile Lys
    530                 535                 540

Arg Glu Pro Lys Ser Cys Asp Lys Thr His Thr Cys Pro Pro Cys Pro
545                 550                 555                 560

Ala Pro Glu Leu Leu Gly Gly Pro Ser Val Phe Leu Phe Pro Pro Lys
                565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
        595                 600                 605

Val Asp Gly Val Glu Val His Asn Ala Lys Thr Lys Pro Arg Glu Glu
    610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
                645                 650                 655

Ala Leu Pro Ala Pro Ile Glu Lys Thr Ile Ser Lys Ala Lys Gly Gln
            660                 665                 670

Pro Arg Glu Pro Gln Val Tyr Thr Leu Pro Pro Ser Arg Glu Glu Met
        675                 680                 685

Thr Lys Asn Gln Val Ser Leu Thr Cys Leu Val Lys Gly Phe Tyr Pro
    690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
                725                 730                 735

Tyr Ser Lys Leu Thr Val Asp Lys Ser Arg Trp Gln Gln Gly Asn Val
            740                 745                 750

Phe Ser Cys Ser Val Met His Glu Ala Leu His Asn His Tyr Thr Gln
```

```
        755                 760                 765

Lys Ser Leu Ser Leu Ser Pro Gly Lys
    770                 775


<210> SEQ ID NO 38
<211> LENGTH: 886
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #31

<400> SEQUENCE: 38

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320
```

```
Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Gly Gly Gly
    530                 535                 540

Gly Ser Asp Ile Gln Met Thr Gln Ser Pro Thr Ser Leu Ser Ala Ser
545                 550                 555                 560

Val Gly Asp Arg Val Thr Ile Thr Cys Arg Ala Ser Gln Trp Ile Gly
                565                 570                 575

Asn Leu Leu Asp Trp Tyr Gln Gln Lys Pro Gly Glu Ala Pro Lys Leu
            580                 585                 590

Leu Ile Tyr Tyr Ala Ser Phe Leu Gln Ser Gly Val Pro Ser Arg Phe
        595                 600                 605

Ser Gly Gly Gly Phe Gly Thr Asp Phe Thr Leu Thr Ile Ser Ser Leu
    610                 615                 620

Gln Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655

Lys Ser Cys Asp Lys Thr His Thr Cys Pro Pro Cys Pro Ala Pro Glu
            660                 665                 670

Leu Leu Gly Gly Pro Ser Val Phe Leu Phe Pro Pro Lys Pro Lys Asp
        675                 680                 685

Thr Leu Met Ile Ser Arg Thr Pro Glu Val Thr Cys Val Val Val Asp
    690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
```

```
            740                 745                 750

Leu Asn Gly Lys Glu Tyr Lys Cys Lys Val Ser Asn Lys Ala Leu Pro
        755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
                885


<210> SEQ ID NO 39
<211> LENGTH: 883
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #32

<400> SEQUENCE: 39

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190
```

-continued

```
Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495

Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Gly Gly Asp
    530                 535                 540

Ile Gln Met Thr Gln Ser Pro Thr Ser Leu Ser Ala Ser Val Gly Asp
545                 550                 555                 560

Arg Val Thr Ile Thr Cys Arg Ala Ser Gln Trp Ile Gly Asn Leu Leu
                565                 570                 575

Asp Trp Tyr Gln Gln Lys Pro Gly Glu Ala Pro Lys Leu Leu Ile Tyr
            580                 585                 590

Tyr Ala Ser Phe Leu Gln Ser Gly Val Pro Ser Arg Phe Ser Gly Gly
        595                 600                 605

Gly Phe Gly Thr Asp Phe Thr Leu Thr Ile Ser Ser Leu Gln Pro Glu
```

```
    610                 615                 620

Asp Phe Ala Thr Tyr Tyr Cys Gln Gln Ala Asn Pro Ala Pro Leu Thr
625                 630                 635                 640

Phe Gly Gln Gly Thr Lys Val Glu Ile Lys Arg Glu Pro Lys Ser Cys
                645                 650                 655

Asp Lys Thr His Thr Cys Pro Pro Cys Pro Ala Pro Glu Leu Leu Gly
            660                 665                 670

Gly Pro Ser Val Phe Leu Phe Pro Pro Lys Pro Lys Asp Thr Leu Met
        675                 680                 685

Ile Ser Arg Thr Pro Glu Val Thr Cys Val Val Val Asp Val Ser His
    690                 695                 700

Glu Asp Pro Glu Val Lys Phe Asn Trp Tyr Val Asp Gly Val Glu Val
705                 710                 715                 720

His Asn Ala Lys Thr Lys Pro Arg Glu Glu Gln Tyr Asn Ser Thr Tyr
                725                 730                 735

Arg Val Val Ser Val Leu Thr Val Leu His Gln Asp Trp Leu Asn Gly
            740                 745                 750

Lys Glu Tyr Lys Cys Lys Val Ser Asn Lys Ala Leu Pro Ala Pro Ile
        755                 760                 765

Glu Lys Thr Ile Ser Lys Ala Lys Gly Gln Pro Arg Glu Pro Gln Val
    770                 775                 780

Tyr Thr Leu Pro Pro Ser Arg Glu Glu Met Thr Lys Asn Gln Val Ser
785                 790                 795                 800

Leu Thr Cys Leu Val Lys Gly Phe Tyr Pro Ser Asp Ile Ala Val Glu
                805                 810                 815

Trp Glu Ser Asn Gly Gln Pro Glu Asn Asn Tyr Lys Thr Thr Pro Pro
            820                 825                 830

Val Leu Asp Ser Asp Gly Ser Phe Phe Leu Tyr Ser Lys Leu Thr Val
        835                 840                 845

Asp Lys Ser Arg Trp Gln Gln Gly Asn Val Phe Ser Cys Ser Val Met
    850                 855                 860

His Glu Ala Leu His Asn His Tyr Thr Gln Lys Ser Leu Ser Leu Ser
865                 870                 875                 880

Pro Gly Lys


<210> SEQ ID NO 40
<211> LENGTH: 886
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #33

<400> SEQUENCE: 40

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
```

```
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Gly Gly Gly Gly Ser Gly Gly Gly
        435                 440                 445

Gly Ser Gly Gly Gly Gly Ser Gly Gly Gly Gly Ser Gly Gly Gly Gly
    450                 455                 460

Ser Met Gln Ile Phe Val Lys Thr Leu Thr Gly Lys Thr Ile Thr Leu
465                 470                 475                 480

Glu Val Glu Pro Ser Asp Thr Ile Glu Asn Val Lys Ala Lys Ile Gln
                485                 490                 495
```

```
Asp Lys Glu Gly Ile Pro Pro Asp Gln Gln Arg Leu Ile Phe Ala Gly
            500                 505                 510

Lys Gln Leu Glu Asp Gly Arg Thr Leu Ser Asp Tyr Asn Ile Gln Lys
        515                 520                 525

Glu Ser Thr Leu His Leu Val Leu Arg Leu Arg Gly Gly Gly Gly Gly
    530                 535                 540

Gly Ser Asp Ile Gln Met Thr Gln Ser Pro Thr Ser Leu Ser Ala Ser
545                 550                 555                 560

Val Gly Asp Arg Val Thr Ile Thr Cys Arg Ala Ser Gln Trp Ile Gly
                565                 570                 575

Asn Leu Leu Asp Trp Tyr Gln Gln Lys Pro Gly Glu Ala Pro Lys Leu
            580                 585                 590

Leu Ile Tyr Tyr Ala Ser Phe Leu Gln Ser Gly Val Pro Ser Arg Phe
        595                 600                 605

Ser Gly Gly Gly Phe Gly Thr Asp Phe Thr Leu Thr Ile Ser Ser Leu
    610                 615                 620

Gln Pro Glu Asp Phe Ala Thr Tyr Tyr Cys Gln Gln Ala Asn Pro Ala
625                 630                 635                 640

Pro Leu Thr Phe Gly Gln Gly Thr Lys Val Glu Ile Lys Arg Glu Pro
                645                 650                 655

Lys Ser Cys Asp Lys Thr His Thr Cys Pro Pro Cys Pro Ala Pro Glu
            660                 665                 670

Leu Leu Gly Gly Pro Ser Val Phe Leu Phe Pro Pro Lys Pro Lys Asp
        675                 680                 685

Thr Leu Met Ile Ser Arg Thr Pro Glu Val Thr Cys Val Val Val Asp
    690                 695                 700

Val Ser His Glu Asp Pro Glu Val Lys Phe Asn Trp Tyr Val Asp Gly
705                 710                 715                 720

Val Glu Val His Asn Ala Lys Thr Lys Pro Arg Glu Glu Gln Tyr Asn
                725                 730                 735

Ser Thr Tyr Arg Val Val Ser Val Leu Thr Val Leu His Gln Asp Trp
            740                 745                 750

Leu Asn Gly Lys Glu Tyr Lys Cys Lys Val Ser Asn Lys Ala Leu Pro
        755                 760                 765

Ala Pro Ile Glu Lys Thr Ile Ser Lys Ala Lys Gly Gln Pro Arg Glu
    770                 775                 780

Pro Gln Val Tyr Thr Leu Pro Pro Ser Arg Glu Glu Met Thr Lys Asn
785                 790                 795                 800

Gln Val Ser Leu Thr Cys Leu Val Lys Gly Phe Tyr Pro Ser Asp Ile
                805                 810                 815

Ala Val Glu Trp Glu Ser Asn Gly Gln Pro Glu Asn Asn Tyr Lys Thr
            820                 825                 830

Thr Pro Pro Val Leu Asp Ser Asp Gly Ser Phe Phe Leu Tyr Ser Lys
        835                 840                 845

Leu Thr Val Asp Lys Ser Arg Trp Gln Gln Gly Asn Val Phe Ser Cys
    850                 855                 860

Ser Val Met His Glu Ala Leu His Asn His Tyr Thr Gln Lys Ser Leu
865                 870                 875                 880

Ser Leu Ser Pro Gly Lys
                885
```

<210> SEQ ID NO 41
<211> LENGTH: 777

<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
specific binding peptides #34

<400> SEQUENCE: 41

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Met Gln Ile Phe Val Lys Thr Leu Thr
        355                 360                 365
```

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Asp Ile Gln Met Thr Gln Ser Pro Thr Ser Leu
        435                 440                 445

Ser Ala Ser Val Gly Asp Arg Val Thr Ile Thr Cys Arg Ala Ser Gln
    450                 455                 460

Trp Ile Gly Asn Leu Leu Asp Trp Tyr Gln Gln Lys Pro Gly Glu Ala
465                 470                 475                 480

Pro Lys Leu Leu Ile Tyr Tyr Ala Ser Phe Leu Gln Ser Gly Val Pro
                485                 490                 495

Ser Arg Phe Ser Gly Gly Gly Phe Gly Thr Asp Phe Thr Leu Thr Ile
            500                 505                 510

Ser Ser Leu Gln Pro Glu Asp Phe Ala Thr Tyr Tyr Cys Gln Gln Ala
        515                 520                 525

Asn Pro Ala Pro Leu Thr Phe Gly Gln Gly Thr Lys Val Glu Ile Lys
    530                 535                 540

Arg Glu Pro Lys Ser Cys Asp Lys Thr His Thr Cys Pro Pro Cys Pro
545                 550                 555                 560

Ala Pro Glu Leu Leu Gly Gly Pro Ser Val Phe Leu Phe Pro Pro Lys
                565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
        595                 600                 605

Val Asp Gly Val Glu Val His Asn Ala Lys Thr Lys Pro Arg Glu Glu
    610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
                645                 650                 655

Ala Leu Pro Ala Pro Ile Glu Lys Thr Ile Ser Lys Ala Lys Gly Gln
            660                 665                 670

Pro Arg Glu Pro Gln Val Tyr Thr Leu Pro Pro Ser Arg Glu Glu Met
        675                 680                 685

Thr Lys Asn Gln Val Ser Leu Thr Cys Leu Val Lys Gly Phe Tyr Pro
    690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
                725                 730                 735

Tyr Ser Lys Leu Thr Val Asp Lys Ser Arg Trp Gln Gln Gly Asn Val
            740                 745                 750

Phe Ser Cys Ser Val Met His Glu Ala Leu His Asn His Tyr Thr Gln
        755                 760                 765

Lys Ser Leu Ser Leu Ser Pro Gly Lys
    770                 775

-continued

<210> SEQ ID NO 42
<211> LENGTH: 780
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
specific binding peptides #35

<400> SEQUENCE: 42

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350
```

-continued

```
Leu Ser Leu Ser Pro Gly Lys Met Gln Ile Phe Val Lys Thr Leu Thr
        355                 360                 365

Gly Lys Thr Ile Thr Leu Glu Val Glu Pro Ser Asp Thr Ile Glu Asn
    370                 375                 380

Val Lys Ala Lys Ile Gln Asp Lys Glu Gly Ile Pro Pro Asp Gln Gln
385                 390                 395                 400

Arg Leu Ile Phe Ala Gly Lys Gln Leu Glu Asp Gly Arg Thr Leu Ser
                405                 410                 415

Asp Tyr Asn Ile Gln Lys Glu Ser Thr Leu His Leu Val Leu Arg Leu
            420                 425                 430

Arg Gly Gly Gly Gly Gly Gly Ser Asp Ile Gln Met Thr Gln Ser Pro
        435                 440                 445

Thr Ser Leu Ser Ala Ser Val Gly Asp Arg Val Thr Ile Thr Cys Arg
    450                 455                 460

Ala Ser Gln Trp Ile Gly Asn Leu Leu Asp Trp Tyr Gln Gln Lys Pro
465                 470                 475                 480

Gly Glu Ala Pro Lys Leu Leu Ile Tyr Tyr Ala Ser Phe Leu Gln Ser
                485                 490                 495

Gly Val Pro Ser Arg Phe Ser Gly Gly Gly Phe Gly Thr Asp Phe Thr
            500                 505                 510

Leu Thr Ile Ser Ser Leu Gln Pro Glu Asp Phe Ala Thr Tyr Tyr Cys
        515                 520                 525

Gln Gln Ala Asn Pro Ala Pro Leu Thr Phe Gly Gln Gly Thr Lys Val
    530                 535                 540

Glu Ile Lys Arg Glu Pro Lys Ser Cys Asp Lys Thr His Thr Cys Pro
545                 550                 555                 560

Pro Cys Pro Ala Pro Glu Leu Leu Gly Gly Pro Ser Val Phe Leu Phe
                565                 570                 575

Pro Pro Lys Pro Lys Asp Thr Leu Met Ile Ser Arg Thr Pro Glu Val
            580                 585                 590

Thr Cys Val Val Val Asp Val Ser His Glu Asp Pro Glu Val Lys Phe
        595                 600                 605

Asn Trp Tyr Val Asp Gly Val Glu Val His Asn Ala Lys Thr Lys Pro
    610                 615                 620

Arg Glu Glu Gln Tyr Asn Ser Thr Tyr Arg Val Val Ser Val Leu Thr
625                 630                 635                 640

Val Leu His Gln Asp Trp Leu Asn Gly Lys Glu Tyr Lys Cys Lys Val
                645                 650                 655

Ser Asn Lys Ala Leu Pro Ala Pro Ile Glu Lys Thr Ile Ser Lys Ala
            660                 665                 670

Lys Gly Gln Pro Arg Glu Pro Gln Val Tyr Thr Leu Pro Pro Ser Arg
        675                 680                 685

Glu Glu Met Thr Lys Asn Gln Val Ser Leu Thr Cys Leu Val Lys Gly
    690                 695                 700

Phe Tyr Pro Ser Asp Ile Ala Val Glu Trp Glu Ser Asn Gly Gln Pro
705                 710                 715                 720

Glu Asn Asn Tyr Lys Thr Thr Pro Pro Val Leu Asp Ser Asp Gly Ser
                725                 730                 735

Phe Phe Leu Tyr Ser Lys Leu Thr Val Asp Lys Ser Arg Trp Gln Gln
            740                 745                 750

Gly Asn Val Phe Ser Cys Ser Val Met His Glu Ala Leu His Asn His
        755                 760                 765
```

Tyr Thr Gln Lys Ser Leu Ser Leu Ser Pro Gly Lys
    770                 775                 780

<210> SEQ ID NO 43
<211> LENGTH: 825
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #36

<400> SEQUENCE: 43

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

-continued

```
Cys Ser Val Met His Glu Ala Leu His Asn His Tyr Thr Gln Lys Ser
            340                 345                 350

Leu Ser Leu Ser Pro Gly Lys Gly Gly Met Lys Arg Gln Gly Lys Glu
        355                 360                 365

Met Asp Ser Leu Arg Phe Leu Tyr Asp Gly Ile Arg Ile Gln Ala Asp
    370                 375                 380

Gln Ala Pro Glu Asp Leu Asp Met Glu Asp Asn Asp Ile Ile Glu Ala
385                 390                 395                 400

His Arg Glu Gln Ile Gly Gly Gly Gly Gly Gly Ser Gly Gly Gly Gly
                405                 410                 415

Ser Gly Gly Gly Gly Ser Gly Gly Gly Gly Ser Gly Gly Gly Gly Ser
            420                 425                 430

Gly Gly Gly Gly Ser Met Lys Arg Gln Gly Lys Glu Met Asp Ser Leu
        435                 440                 445

Arg Phe Leu Tyr Asp Gly Ile Arg Ile Gln Ala Asp Gln Ala Pro Glu
    450                 455                 460

Asp Leu Asp Met Glu Asp Asn Asp Ile Ile Glu Ala His Arg Glu Gln
465                 470                 475                 480

Ile Gly Gly Gly Gly Asp Ile Gln Met Thr Gln Ser Pro Thr Ser Leu
                485                 490                 495

Ser Ala Ser Val Gly Asp Arg Val Thr Ile Thr Cys Arg Ala Ser Gln
            500                 505                 510

Trp Ile Gly Asn Leu Leu Asp Trp Tyr Gln Gln Lys Pro Gly Glu Ala
        515                 520                 525

Pro Lys Leu Leu Ile Tyr Tyr Ala Ser Phe Leu Gln Ser Gly Val Pro
    530                 535                 540

Ser Arg Phe Ser Gly Gly Gly Phe Gly Thr Asp Phe Thr Leu Thr Ile
545                 550                 555                 560

Ser Ser Leu Gln Pro Glu Asp Phe Ala Thr Tyr Tyr Cys Gln Gln Ala
                565                 570                 575

Asn Pro Ala Pro Leu Thr Phe Gly Gln Gly Thr Lys Val Glu Ile Lys
            580                 585                 590

Arg Glu Pro Lys Ser Cys Asp Lys Thr His Thr Cys Pro Pro Cys Pro
        595                 600                 605

Ala Pro Glu Leu Leu Gly Gly Pro Ser Val Phe Leu Phe Pro Pro Lys
    610                 615                 620

Pro Lys Asp Thr Leu Met Ile Ser Arg Thr Pro Glu Val Thr Cys Val
625                 630                 635                 640

Val Val Asp Val Ser His Glu Asp Pro Glu Val Lys Phe Asn Trp Tyr
                645                 650                 655

Val Asp Gly Val Glu Val His Asn Ala Lys Thr Lys Pro Arg Glu Glu
            660                 665                 670

Gln Tyr Asn Ser Thr Tyr Arg Val Val Ser Val Leu Thr Val Leu His
        675                 680                 685

Gln Asp Trp Leu Asn Gly Lys Glu Tyr Lys Cys Lys Val Ser Asn Lys
    690                 695                 700

Ala Leu Pro Ala Pro Ile Glu Lys Thr Ile Ser Lys Ala Lys Gly Gln
705                 710                 715                 720

Pro Arg Glu Pro Gln Val Tyr Thr Leu Pro Pro Ser Arg Glu Glu Met
                725                 730                 735

Thr Lys Asn Gln Val Ser Leu Thr Cys Leu Val Lys Gly Phe Tyr Pro
            740                 745                 750
```

-continued

```
Ser Asp Ile Ala Val Glu Trp Glu Ser Asn Gly Gln Pro Glu Asn Asn
        755                 760                 765

Tyr Lys Thr Thr Pro Pro Val Leu Asp Ser Asp Gly Ser Phe Phe Leu
    770                 775                 780

Tyr Ser Lys Leu Thr Val Asp Lys Ser Arg Trp Gln Gln Gly Asn Val
785                 790                 795                 800

Phe Ser Cys Ser Val Met His Glu Ala Leu His Asn His Tyr Thr Gln
                805                 810                 815

Lys Ser Leu Ser Leu Ser Pro Gly Lys
            820                 825


<210> SEQ ID NO 44
<211> LENGTH: 753
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein complex comprising VEGF and EGFR
      specific binding peptides #37

<400> SEQUENCE: 44

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Lys Ile
        35                  40                  45

Phe Asn Gly Leu Ser Trp Tyr Gln Gln Lys Pro Gly Lys Ala Pro Lys
    50                  55                  60

Leu Leu Ile Tyr His Ser Ser Thr Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Val Leu Leu
            100                 105                 110

Tyr Pro Tyr Thr Phe Gly Gln Gly Thr Lys Val Glu Ile Lys Arg Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270
```

-continued

```
Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Asp Tyr Asp Ile Pro Thr Thr Glu Asn
        355                 360                 365

Leu Tyr Phe Gln Gly Gly Gly Gly Gly Ser Gly Gly Gly Gly Ser Gly
    370                 375                 380

Gly Gly Gly Ser Gly Gly Gly Gly Ser Gly Gly Gly Gly Ser Gly Gly
385                 390                 395                 400

Gly Gly Ser Glu Asn Leu Tyr Phe Gln Gly Ser Gly Gly Asp Ile Gln
                405                 410                 415

Met Thr Gln Ser Pro Thr Ser Leu Ser Ala Ser Val Gly Asp Arg Val
            420                 425                 430

Thr Ile Thr Cys Arg Ala Ser Gln Trp Ile Gly Asn Leu Leu Asp Trp
        435                 440                 445

Tyr Gln Gln Lys Pro Gly Glu Ala Pro Lys Leu Leu Ile Tyr Tyr Ala
    450                 455                 460

Ser Phe Leu Gln Ser Gly Val Pro Ser Arg Phe Ser Gly Gly Gly Phe
465                 470                 475                 480

Gly Thr Asp Phe Thr Leu Thr Ile Ser Ser Leu Gln Pro Glu Asp Phe
                485                 490                 495

Ala Thr Tyr Tyr Cys Gln Gln Ala Asn Pro Ala Pro Leu Thr Phe Gly
            500                 505                 510

Gln Gly Thr Lys Val Glu Ile Lys Arg Glu Pro Lys Ser Cys Asp Lys
        515                 520                 525

Thr His Thr Cys Pro Pro Cys Pro Ala Pro Glu Leu Leu Gly Gly Pro
    530                 535                 540

Ser Val Phe Leu Phe Pro Pro Lys Pro Lys Asp Thr Leu Met Ile Ser
545                 550                 555                 560

Arg Thr Pro Glu Val Thr Cys Val Val Val Asp Val Ser His Glu Asp
                565                 570                 575

Pro Glu Val Lys Phe Asn Trp Tyr Val Asp Gly Val Glu Val His Asn
            580                 585                 590

Ala Lys Thr Lys Pro Arg Glu Glu Gln Tyr Asn Ser Thr Tyr Arg Val
        595                 600                 605

Val Ser Val Leu Thr Val Leu His Gln Asp Trp Leu Asn Gly Lys Glu
    610                 615                 620

Tyr Lys Cys Lys Val Ser Asn Lys Ala Leu Pro Ala Pro Ile Glu Lys
625                 630                 635                 640

Thr Ile Ser Lys Ala Lys Gly Gln Pro Arg Glu Pro Gln Val Tyr Thr
                645                 650                 655

Leu Pro Pro Ser Arg Glu Glu Met Thr Lys Asn Gln Val Ser Leu Thr
            660                 665                 670

Cys Leu Val Lys Gly Phe Tyr Pro Ser Asp Ile Ala Val Glu Trp Glu
        675                 680                 685
```

```
Ser Asn Gly Gln Pro Glu Asn Asn Tyr Lys Thr Thr Pro Pro Val Leu
    690                 695                 700

Asp Ser Asp Gly Ser Phe Phe Leu Tyr Ser Lys Leu Thr Val Asp Lys
705                 710                 715                 720

Ser Arg Trp Gln Gln Gly Asn Val Phe Ser Cys Ser Val Met His Glu
                725                 730                 735

Ala Leu His Asn His Tyr Thr Gln Lys Ser Leu Ser Leu Ser Pro Gly
            740                 745                 750

Lys


<210> SEQ ID NO 45
<211> LENGTH: 2634
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #1

<400> SEQUENCE: 45

gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtag agccagccag tggatcggcc ctgagctgag ctggtatcag    180

cagaagcccg gcaaggcccc caagctgctg atctaccaca ccagcatcct gcagagcggc    240

gtgcccagca gattttctgg cagcggcagc ggcaccgact tcaccctgac aatcagcagc    300

ctgcagcccg aggacttcgc cacctactac tgccagcagt acatgttcca gccccggacc    360

tttggccagg gcaccaaggt ggaaatcaga agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagccccaga    780

gaaccccagg tgtacacact gccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtatg   1380

cagatttttg tcaagacact gaccgggaaa acaatcacac tcgaagtcga gccctccgat   1440

acaattgaga atgtgaaagc caaaattcag gacaaagaag ggattcctcc tgatcagcag   1500

cggctgattt ttgccggaaa acagctcgaa gatggacgga ccctgtccga ttacaatatt   1560
```

-continued

```
cagaaagaaa gcaccctcca tctggtcctg aggctgcggg gaggcgacat tcagatgaca   1620

cagtccccca gctccctgag cgccagcgtg ggagatcgcg tgaccattac atgccgggcc   1680

tcccagtgga ttggcatcct ggtggattgg tatcagcaga aacctgggga ggctcctaaa   1740

ctgctgatct attacgccag ctttctgcag tccggcgtgc cctctagatt cagcggctct   1800

ggcttcggca cagatttcac actgaccatc tctagcctgc accctgaaga ttttgccaca   1860

tattactgtc agcaggccaa ccctgccccc ctgacattcg gccagggaac aaaggtcgag   1920

atcaagcgcg agcccaagtc ctgtgataag acacatacct gccccccctg cccagctcca   1980

gaactgctcg gaggaccttc tgtgtttctg tttccaccca agcctaagga tacactcatg   2040

atctccagaa cacctgaagt gacatgtgtg gtcgtcgacg tgtcacatga ggatccagaa   2100

gtcaagttta actggtatgt ggatggggtc gaggtgcaca atgccaaaac aaaacctcgg   2160

gaagaacagt ataattccac ctatagagtc gtgtctgtgc tcaccgtgct ccatcaggat   2220

tggctcaatg ggaaagaata caaatgtaaa gtctctaaca aagccctgcc cgctcctatc   2280

gaaaagacaa tctccaaggc caaaggacag cctcgcgagc ctcaggtcta caccctgcca   2340

ccttcccgcg aggaaatgac aaaaaatcag gtgtcactca cctgtctcgt gaaggggttt   2400

taccctccg acattgccgt cgagtgggag tccaatggac agcccgagaa caattataag   2460

acaacacctc ccgtcctgga ctccgatgga tcattttttc tgtactccaa gctcaccgtc   2520

gataagtcca gatggcagca gggaaatgtc ttttcctgct ccgtgatgca tgaagctctc   2580

cacaatcatt acacacagaa aagcctgtcc ctgtccccg gcaagtgact cgag          2634
```

<210> SEQ ID NO 46
<211> LENGTH: 2649
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #2

<400> SEQUENCE: 46

```
gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtag agccagccag tggatcggcc ctgagctgag ctggtatcag    180

cagaagcccg gcaaggcccc caagctgctg atctaccaca ccagcatcct gcagagcggc    240

gtgcccagca gattttctgg cagcggcagc ggcaccgact tcaccctgac aatcagcagc    300

ctgcagcccg aggacttcgc cacctactac tgccagcagt acatgttcca gccccggacc    360

tttggccagg gcaccaaggt ggaaatcaga agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gccccccagc agagaagaga tgaccaagaa ccaggtgtcc    840
```

```
ctgacctgcc tggtcaaggg cttctacccc agcgatatcg ccgtggaatg ggagagcaac    900

ggccagcctg agaacaacta caagaccacc cccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtggt   1380

ggcggtggta gtatgcagat ttttgtcaag acactgaccg ggaaaacaat cacactcgaa   1440

gtcgagccct ccgatacaat tgagaatgtg aaagccaaaa ttcaggacaa agaagggatt   1500

cctcctgatc agcagcggct gatttttgcc ggaaaacagc tcgaagatgg acggaccctg   1560

tccgattaca atattcagaa agaaagcacc ctccatctgg tcctgaggct gcggggaggc   1620

gacattcaga tgacacagtc ccccagctcc ctgagcgcca gcgtgggaga tcgcgtgacc   1680

attacatgcc gggcctccca gtggattggc atcctggtgg attggtatca gcagaaacct   1740

ggggaggctc ctaaactgct gatctattac gccagctttc tgcagtccgg cgtgccctct   1800

agattcagcg gctctggctt cggcacagat ttcacactga ccatctctag cctgcaccct   1860

gaagattttg ccacatatta ctgtcagcag gccaaccctg ccccctgac attcggccag   1920

ggaacaaagg tcgagatcaa gcgcgagccc aagtcctgtg ataagacaca tacctgcccc   1980

ccctgcccag ctccagaact gctcggagga ccttctgtgt ttctgtttcc acccaagcct   2040

aaggatacac tcatgatctc cagaacacct gaagtgacat gtgtggtcgt cgacgtgtca   2100

catgaggatc cagaagtcaa gtttaactgg tatgtggatg gggtcgaggt gcacaatgcc   2160

aaaacaaaac ctcgggaaga acagtataat tccacctata gagtcgtgtc tgtgctcacc   2220

gtgctccatc aggattggct caatgggaaa gaatacaaat gtaaagtctc taacaaagcc   2280

ctgcccgctc ctatcgaaaa gacaatctcc aaggccaaag gacagcctcg cgagcctcag   2340

gtctacaccc tgccaccttc ccgcgaggaa atgacaaaaa atcaggtgtc actcacctgt   2400

ctcgtgaagg ggttttaccc ctccgacatt gccgtcgagt gggagtccaa tggacagccc   2460

gagaacaatt ataagacaac acctcccgtc ctggactccg atggatcatt ttttctgtac   2520

tccaagctca ccgtcgataa gtccagatgg cagcagggaa atgtcttttc ctgctccgtg   2580

atgcatgaag ctctccacaa tcattacaca cagaaaagcc tgtccctgtc ccccggcaag   2640

tgactcgag                                                           2649
```

```
<210> SEQ ID NO 47
<211> LENGTH: 2664
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #3

<400> SEQUENCE: 47

gaattcgcca ccatgggctg gtcctgcatc atcctgtttc tggtggccac cgccaccggc     60

gtgcactctg atatccagat gacccagagc cccagcagcc tgtctgcctc tgtgggcgac    120
```

-continued

```
agagtgacca tcacctgtag agccagccag tggatcggcc ctgagctgag ctggtatcag    180
cagaagcccg gcaaggcccc caagctgctg atctaccaca ccagcatcct gcagagcggc    240
gtgcccagca gattttctgg cagcggcagc ggcaccgact tcaccctgac aatcagcagc    300
ctgcagcccg aggacttcgc cacctactac tgccagcagt acatgttcca gccccggacc    360
tttggccagg gcaccaaggt ggaaatcaga agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccagc agagaagaga tgaccaagaa ccaggtgtcc     840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcatg cagatttttg tcaagacact gaccgggaaa   1440
acaatcacac tcgaagtcga gccctccgat acaattgaga atgtgaaagc caaaattcag   1500
gacaaagaag ggattcctcc tgatcagcag cggctgattt ttgccggaaa acagctcgaa   1560
gatggacgga ccctgtccga ttacaatatt cagaaagaaa gcaccctcca tctggtcctg   1620
aggctgcggg gaggcgacat tcagatgaca cagtccccca gctccctgag cgccagcgtg   1680
ggagatcgcg tgaccattac atgccgggcc tcccagtgga ttggcatcct ggtggattgg   1740
tatcagcaga aacctgggga ggctcctaaa ctgctgatct attacgccag ctttctgcag   1800
tccggcgtgc cctctagatt cagcggctct ggcttcggca cagatttcac actgaccatc   1860
tctagcctgc accctgaaga ttttgccaca tattactgtc agcaggccaa ccctgccccc   1920
ctgacattcg gccagggaac aaaggtcgag atcaagcgcg agcccaagtc ctgtgataag   1980
acacatacct gcccccctg cccagctcca gaactgctcg gaggaccttc tgtgtttctg    2040
tttccaccca agcctaagga tacactcatg atctccagaa cacctgaagt gacatgtgtg   2100
gtcgtcgacg tgtcacatga ggatccagaa gtcaagttta actggtatgt ggatggggtc   2160
gaggtgcaca atgccaaaac aaaacctcgg gaagaacagt ataattccac ctatagagtc   2220
gtgtctgtgc tcaccgtgct ccatcaggat tggctcaatg ggaaagaata caaatgtaaa   2280
gtctctaaca aagccctgcc cgctcctatc gaaaagacaa tctccaaggc caaaggacag   2340
cctcgcgagc ctcaggtcta caccctgcca ccttcccgcg aggaaatgac aaaaaatcag   2400
gtgtcactca cctgtctcgt gaaggggttt taccccctccg acattgccgt cgagtgggag   2460
```

tccaatggac agcccgagaa caattataag acaacacctc ccgtcctgga ctccgatgga 2520
tcattttttc tgtactccaa gctcaccgtc gataagtcca gatggcagca gggaaatgtc 2580
ttttcctgct ccgtgatgca tgaagctctc cacaatcatt acacacagaa aagcctgtcc 2640
ctgtcccccg gcaagtgact cgag 2664

<210> SEQ ID NO 48
<211> LENGTH: 2679
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #4

<400> SEQUENCE: 48
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtag agccagccag tggatcggcc ctgagctgag ctggtatcag 180
cagaagcccg gcaaggcccc caagctgctg atctaccaca ccagcatcct gcagagcggc 240
gtgcccagca gattttctgg cagcggcagc ggcaccgact tcaccctgac aatcagcagc 300
ctgcagcccg aggacttcgc cacctactac tgccagcagt acatgttcca gccccggacc 360
tttggccagg gcaccaaggt ggaaatcaga agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caatgcagat ttttgtcaag 1440
acactgaccg ggaaaacaat cacactcgaa gtcgagccct ccgatacaat tgagaatgtg 1500
aaagccaaaa ttcaggacaa agaagggatt cctcctgatc agcagcggct gatttttgcc 1560
ggaaaacagc tcgaagatgg acggaccctg tccgattaca atattcagaa agaaagcacc 1620
ctccatctgg tcctgaggct gcggggaggc gacattcaga tgacacagtc ccccagctcc 1680
ctgagcgcca gcgtgggaga tcgcgtgacc attacatgcc gggcctccca gtggattggc 1740
atcctggtgg attggtatca gcagaaacct ggggaggctc ctaaactgct gatctattac 1800
gccagctttc tgcagtccgg cgtgccctct agattcagcg gctctggctt cggcacagat 1860
ttcacactga ccatctctag cctgcaccct gaagattttg ccacatatta ctgtcagcag 1920
gccaaccctg ccccctgac attcggccag ggaacaaagg tcgagatcaa gcgcgagccc 1980
aagtcctgtg ataagacaca tacctgcccc ccctgcccag ctccagaact gctcggagga 2040
ccttctgtgt ttctgtttcc acccaagcct aaggatacac tcatgatctc cagaacacct 2100
gaagtgacat gtgtggtcgt cgacgtgtca catgaggatc cagaagtcaa gtttaactgg 2160
tatgtggatg gggtcgaggt gcacaatgcc aaaacaaaac ctcgggaaga acagtataat 2220
tccacctata gagtcgtgtc tgtgctcacc gtgctccatc aggattggct caatgggaaa 2280
gaatacaaat gtaaagtctc taacaaagcc ctgcccgctc ctatcgaaaa gacaatctcc 2340
aaggccaaag gacagcctcg cgagcctcag gtctacaccc tgccaccttc ccgcgaggaa 2400
atgacaaaaa atcaggtgtc actcacctgt ctcgtgaagg ggttttaccc ctccgacatt 2460
gccgtcgagt gggagtccaa tggacagccc gagaacaatt ataagacaac acctcccgtc 2520
ctggactccg atggatcatt ttttctgtac tccaagctca ccgtcgataa gtccagatgg 2580
cagcagggaa atgtcttttc ctgctccgtg atgcatgaag ctctccacaa tcattacaca 2640
cagaaaagcc tgtccctgtc ccccggcaag tgactcgag 2679

<210> SEQ ID NO 49
<211> LENGTH: 2694
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #5

<400> SEQUENCE: 49
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtag agccagccag tggatcggcc ctgagctgag ctggtatcag 180
cagaagcccg gcaaggcccc caagctgctg atctaccaca ccagcatcct gcagagcggc 240
gtgcccagca gattttctgg cagcggcagc ggcaccgact tcaccctgac aatcagcagc 300
ctgcagcccg aggacttcgc cacctactac tgccagcagt acatgttcca gccccggacc 360
tttggccagg gcaccaaggt ggaaatcaga agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960

-continued ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caggcggagg cggatcaatg 1440
cagatttttg tcaagacact gaccgggaaa acaatcacac tcgaagtcga gccctccgat 1500
acaattgaga atgtgaaagc caaaattcag gacaaagaag ggattcctcc tgatcagcag 1560
cggctgattt ttgccggaaa acagctcgaa gatggacgga ccctgtccga ttacaatatt 1620
cagaaagaaa gcaccctcca tctggtcctg aggctgcggg gaggcgacat tcagatgaca 1680
cagtccccca gctccctgag cgccagcgtg ggagatcgcg tgaccattac atgccgggcc 1740
tcccagtgga ttggcatcct ggtggattgg tatcagcaga aacctgggga ggctcctaaa 1800
ctgctgatct attacgccag ctttctgcag tccggcgtgc cctctagatt cagcggctct 1860
ggcttcggca cagatttcac actgaccatc tctagcctgc accctgaaga ttttgccaca 1920
tattactgtc agcaggccaa ccctgccccc ctgacattcg gccagggaac aaaggtcgag 1980
atcaagcgcg agcccaagtc ctgtgataag acacatacct gccccccctg cccagctcca 2040
gaactgctcg gaggaccttc tgtgtttctg tttccaccca agcctaagga tacactcatg 2100
atctccagaa cacctgaagt gacatgtgtg gtcgtcgacg tgtcacatga ggatccagaa 2160
gtcaagttta actggtatgt ggatggggtc gaggtgcaca atgccaaaac aaaacctcgg 2220
gaagaacagt ataattccac ctatagagtc gtgtctgtgc tcaccgtgct ccatcaggat 2280
tggctcaatg ggaaagaata caaatgtaaa gtctctaaca aagccctgcc cgctcctatc 2340
gaaaagacaa tctccaaggc caaaggacag cctcgcgagc ctcaggtcta caccctgcca 2400
ccttcccgcg aggaaatgac aaaaaatcag gtgtcactca cctgtctcgt gaaggggttt 2460 taccccctccg acattgccgt cgagtgggag tccaatggac agcccgagaa caattataag 2520
acaacacctc ccgtcctgga ctccgatgga tcattttttc tgtactccaa gctcaccgtc 2580
gataagtcca gatggcagca gggaaatgtc ttttcctgct ccgtgatgca tgaagctctc 2640
cacaatcatt acacacagaa aagcctgtcc ctgtcccccg gcaagtgact cgag 2694

<210> SEQ ID NO 50
<211> LENGTH: 2709
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #6

<400> SEQUENCE: 50
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtag agccagccag tggatcggcc ctgagctgag ctggtatcag 180
cagaagcccg gcaaggcccc caagctgctg atctaccaca ccagcatcct gcagagcggc 240

-continued

```
gtgcccagca gattttctgg cagcggcagc ggcaccgact tcaccctgac aatcagcagc    300
ctgcagcccg aggacttcgc cacctactac tgccagcagt acatgttcca gccccggacc    360
tttggccagg gcaccaaggt ggaaatcaga agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caggcggagg cggatcaggt   1440
ggcgggggtt caatgcagat ttttgtcaag acactgaccg ggaaaacaat cacactcgaa   1500
gtcgagccct ccgatacaat tgagaatgtg aaagccaaaa ttcaggacaa agaagggatt   1560
cctcctgatc agcagcggct gatttttgcc ggaaaacagc tcgaagatgg acggaccctg   1620
tccgattaca atattcagaa agaaagcacc ctccatctgg tcctgaggct gcggggaggc   1680
gacattcaga tgacacagtc cccagctcc ctgagcgcca gcgtgggaga tcgcgtgacc   1740
attacatgcc gggcctccca gtggattggc atcctggtgg attggtatca gcagaaacct   1800
ggggaggctc ctaaactgct gatctattac gccagctttc tgcagtccgg cgtgccctct   1860
agattcagcg gctctggctt cggcacagat ttcacactga ccatctctag cctgcaccct   1920
gaagattttg ccacatatta ctgtcagcag gccaaccctg cccccctgac attcggccag   1980
ggaacaaagg tcgagatcaa gcgcgagccc aagtcctgtg ataagacaca tacctgcccc   2040
ccctgcccag ctccagaact gctcggagga ccttctgtgt ttctgtttcc acccaagcct   2100
aaggatacac tcatgatctc cagaacacct gaagtgacat gtgtggtcgt cgacgtgtca   2160
catgaggatc cagaagtcaa gtttaactgg tatgtggatg gggtcgaggt gcacaatgcc   2220
aaaacaaaac ctcgggaaga acagtataat tccacctata gagtcgtgtc tgtgctcacc   2280
gtgctccatc aggattggct caatgggaaa gaatacaaat gtaaagtctc taacaaagcc   2340
ctgcccgctc ctatcgaaaa gacaatctcc aaggccaaag gacagcctcg cgagcctcag   2400
gtctacaccc tgccaccttc ccgcgaggaa atgacaaaaa atcaggtgtc actcacctgt   2460
ctcgtgaagg ggttttaccc ctccgacatt gccgtcgagt gggagtccaa tggacagccc   2520
gagaacaatt ataagacaac acctcccgtc ctggactccg atggatcatt ttttctgtac   2580
```

tccaagctca ccgtcgataa gtccagatgg cagcagggaa atgtcttttc ctgctccgtg 2640
atgcatgaag ctctccacaa tcattacaca cagaaaagcc tgtccctgtc cccggcaag 2700 tgactcgag 2709

<210> SEQ ID NO 51
<211> LENGTH: 2724
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #7

<400> SEQUENCE: 51
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtag agccagccag tggatcggcc ctgagctgag ctggtatcag 180
cagaagcccg gcaaggcccc caagctgctg atctaccaca ccagcatcct gcagagcggc 240
gtgcccagca gatttctgg cagcggcagc ggcaccgact tcaccctgac aatcagcagc 300
ctgcagcccg aggacttcgc cacctactac tgccagcagt acatgttcca gccccggacc 360
tttggccagg gcaccaaggt ggaaatcaga agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc cccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caggcggagg cggatcaggt 1440
ggcgggggtt caggggggtgg cggaagtatg cagatttttg tcaagacact gaccgggaaa 1500
acaatcacac tcgaagtcga gccctccgat acaattgaga atgtgaaagc caaaattcag 1560
gacaaagaag ggattcctcc tgatcagcag cggctgattt ttgccggaaa acagctcgaa 1620
gatggacgga ccctgtccga ttacaatatt cagaaagaaa gcaccctcca tctggtcctg 1680
aggctgcggg gaggcgacat tcagatgaca cagtccccca gctccctgag cgccagcgtg 1740
ggagatcgcg tgaccattac atgccgggcc tcccagtgga ttggcatcct ggtggattgg 1800

```
tatcagcaga aacctgggga ggctcctaaa ctgctgatct attacgccag ctttctgcag   1860

tccggcgtgc cctctagatt cagcggctct ggcttcggca cagatttcac actgaccatc   1920

tctagcctgc accctgaaga ttttgccaca tattactgtc agcaggccaa ccctgccccc   1980

ctgacattcg gccagggaac aaaggtcgag atcaagcgcg agcccaagtc ctgtgataag   2040

acacatacct gccccccctg cccagctcca gaactgctcg gaggaccttc tgtgtttctg   2100

tttccaccca agcctaagga tacactcatg atctccagaa cacctgaagt gacatgtgtg   2160

gtcgtcgacg tgtcacatga ggatccagaa gtcaagttta actggtatgt ggatggggtc   2220

gaggtgcaca atgccaaaac aaaacctcgg gaagaacagt ataattccac ctatagagtc   2280

gtgtctgtgc tcaccgtgct ccatcaggat tggctcaatg ggaaagaata caaatgtaaa   2340

gtctctaaca aagccctgcc cgctcctatc gaaaagacaa tctccaaggc caaaggacag   2400

cctcgcgagc ctcaggtcta caccctgcca ccttcccgcg aggaaatgac aaaaaatcag   2460

gtgtcactca cctgtctcgt gaaggggttt tacccctccg acattgccgt cgagtgggag   2520

tccaatggac agcccgagaa caattataag acaacacctc ccgtcctgga ctccgatgga   2580

tcatttttttc tgtactccaa gctcaccgtc gataagtcca gatggcagca gggaaatgtc   2640

ttttcctgct ccgtgatgca tgaagctctc cacaatcatt acacacagaa aagcctgtcc   2700

ctgtcccccg gcaagtgact cgag                                          2724
```

```
<210> SEQ ID NO 52
<211> LENGTH: 2634
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #8

<400> SEQUENCE: 52

gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtag agccagccag tggatcggcc ctgagctgag ctggtatcag    180

cagaagcccg gcaaggcccc caagctgctg atctaccaca ccagcatcct gcagagcggc    240

gtgcccagca gatttctggg cagcggcagc ggcaccgact tcaccctgac aatcagcagc    300

ctgcagcccg aggacttcgc cacctactac tgccagcagt acatgttcca gccccggacc    360

tttggccagg gcaccaaggt ggaaatcaga agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960
```

```
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtatg   1380
cagatttttg tcaagacact gaccgggaaa acaatcacac tcgaagtcga gccctccgat   1440
acaattgaga atgtgaaagc caaaattcag gacaaagaag ggattcctcc tgatcagcag   1500
cggctgattt ttgccggaaa acagctcgaa gatggacgga ccctgtccga ttacaatatt   1560
cagaaagaaa gcaccctcca tctggtcctg aggctgcggg gaggcgacat tcagatgaca   1620
cagtccccca cctccctgtc tgccagcgtg ggagatcgcg tgaccattac atgccgggcc   1680
tcccagtgga ttggcaacct gctggattgg tatcagcaga aacctgggga ggctcctaaa   1740
ctgctgatct attacgccag ctttctgcag tccggcgtgc cctccagatt cagcggcgga   1800
ggcttcggca cagatttcac actgaccatc tcatccctgc agcctgaaga ttttgccaca   1860
tattattgcc agcaggccaa ccctgccccc ctgacattcg gccagggaac aaaggtcgag   1920
atcaagcgcg agcccaagtc ctgtgataag acacatacct gccccccctg cccagctcca   1980
gaactgctcg gaggaccttc tgtgtttctg tttccaccca agcctaagga tacactcatg   2040
atctccagaa cacctgaagt gacatgtgtg gtcgtcgacg tgtcacatga ggatccagaa   2100
gtcaagttta actggtatgt ggatggggtc gaggtgcaca atgccaaaac aaaacctcgg   2160
gaagaacagt ataattccac ctatagagtc gtgtctgtgc tcaccgtgct ccatcaggat   2220
tggctcaatg ggaaagaata caaatgtaaa gtctctaaca aagccctgcc cgctcctatc   2280
gaaaagacaa tctccaaggc caaaggacag cctcgcgagc ctcaggtcta caccctgcca   2340
cctagccgcg aggaaatgac aaaaaatcag gtgtcactca cctgtctcgt gaaggggttt   2400
taccccctccg acattgccgt cgagtgggag tccaatggac agcccgagaa caattataag   2460
acaacacctc ccgtcctgga ctccgatgga tcatttttc tgtactccaa gctcaccgtc   2520
gataagtcca gatggcagca gggaaatgtc ttttcctgct ccgtgatgca tgaagctctc   2580
cacaatcatt acacacagaa aagcctgtcc ctgtccccg gcaagtgact cgag          2634
```

<210> SEQ ID NO 53
<211> LENGTH: 2649
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #9

<400> SEQUENCE: 53

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtag agccagccag tggatcggcc ctgagctgag ctggtatcag    180
cagaagcccg gcaaggcccc caagctgctg atctaccaca ccagcatcct gcagagcggc    240
gtgcccagca gattttctgg cagcggcagc ggcaccgact tcaccctgac aatcagcagc    300
```

-continued

```
ctgcagcccg aggacttcgc cacctactac tgccagcagt acatgttcca gccccggacc    360
tttggccagg gcaccaaggt ggaaatcaga agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtatgcagat ttttgtcaag acactgaccg ggaaaacaat cacactcgaa   1440
gtcgagccct ccgatacaat tgagaatgtg aaagccaaaa ttcaggacaa agaagggatt   1500
cctcctgatc agcagcggct gatttttgcc ggaaaacagc tcgaagatgg acggaccctg   1560
tccgattaca atattcagaa agaaagcacc ctccatctgg tcctgaggct gcggggaggc   1620
gacattcaga tgacacagtc ccccacctcc ctgtctgcca gcgtgggaga tcgcgtgacc   1680
attacatgcc gggcctccca gtggattggc aacctgctgg attggtatca gcagaaacct   1740
ggggaggctc ctaaactgct gatctattac gccagctttc tgcagtccgg cgtgccctcc   1800
agattcagcg gcggaggctt cggcacagat ttcacactga ccatctcatc cctgcagcct   1860
gaagattttg ccacatatta ttgccagcag gccaaccctg ccccccctgac attcggccag   1920
ggaacaaagg tcgagatcaa gcgcgagccc aagtcctgtg ataagacaca tacctgcccc   1980
ccctgcccag ctccagaact gctcggagga ccttctgtgt ttctgtttcc acccaagcct   2040
aaggatacac tcatgatctc cagaacacct gaagtgacat gtgtggtcgt cgacgtgtca   2100
catgaggatc cagaagtcaa gtttaactgg tatgtggatg gggtcgaggt gcacaatgcc   2160
aaaacaaaac ctcgggaaga acagtataat tccacctata gagtcgtgtc tgtgctcacc   2220
gtgctccatc aggattggct caatgggaaa gaatacaaat gtaaagtctc taacaaagcc   2280
ctgcccgctc ctatcgaaaa gacaatctcc aaggccaaag gacagcctcg cgagcctcag   2340
gtctacaccc tgccacctag ccgcgaggaa atgacaaaaa atcaggtgtc actcacctgt   2400
ctcgtgaagg ggttttaccc ctccgacatt gccgtcgagt gggagtccaa tggacagccc   2460
gagaacaatt ataagacaac acctcccgtc ctggactccg atggatcatt ttttctgtac   2520
tccaagctca ccgtcgataa gtccagatgg cagcagggaa atgtcttttc ctgctccgtg   2580
atgcatgaag ctctccacaa tcattacaca cagaaaagcc tgtccctgtc ccccggcaag   2640
```

tgactcgag 2649

<210> SEQ ID NO 54
<211> LENGTH: 2664
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #10

<400> SEQUENCE: 54
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtag agccagccag tggatcggcc ctgagctgag ctggtatcag 180
cagaagcccg gcaaggcccc caagctgctg atctaccaca ccagcatcct gcagagcggc 240
gtgcccagca gatttctgg cagcggcagc ggcaccgact tcaccctgac aatcagcagc 300
ctgcagcccg aggacttcgc cacctactac tgccagcagt acatgttcca gccccggacc 360
tttggccagg gcaccaaggt ggaaatcaga agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcatg cagatttttg tcaagacact gaccgggaaa 1440
acaatcacac tcgaagtcga gccctccgat acaattgaga atgtgaaagc caaaattcag 1500
gacaaagaag ggattcctcc tgatcagcag cggctgattt ttgccggaaa acagctcgaa 1560
gatggacgga ccctgtccga ttacaatatt cagaaagaaa gcaccctcca tctggtcctg 1620
aggctgcggg gaggcgacat tcagatgaca cagtccccca cctccctgtc tgccagcgtg 1680
ggagatcgcg tgaccattac atgccgggcc tcccagtgga ttggcaacct gctggattgg 1740
tatcagcaga aacctgggga ggctcctaaa ctgctgatct attacgccag ctttctgcag 1800
tccggcgtgc cctccagatt cagcggcgga ggcttcggca cagatttcac actgaccatc 1860
tcatccctgc agcctgaaga ttttgccaca tattattgcc agcaggccaa ccctgccccc 1920

```
ctgacattcg gccagggaac aaaggtcgag atcaagcgcg agcccaagtc ctgtgataag   1980

acacatacct gcccccctg cccagctcca gaactgctcg gaggaccttc tgtgtttctg   2040

tttccaccca agcctaagga tacactcatg atctccagaa cacctgaagt gacatgtgtg   2100

gtcgtcgacg tgtcacatga ggatccagaa gtcaagttta actggtatgt ggatggggtc   2160

gaggtgcaca atgccaaaac aaaacctcgg gaagaacagt ataattccac ctatagagtc   2220

gtgtctgtgc tcaccgtgct ccatcaggat tggctcaatg ggaaagaata caaatgtaaa   2280

gtctctaaca aagccctgcc cgctcctatc gaaaagacaa tctccaaggc caaaggacag   2340

cctcgcgagc ctcaggtcta caccctgcca cctagccgcg aggaaatgac aaaaaatcag   2400

gtgtcactca cctgtctcgt gaaggggttt taccccctccg acattgccgt cgagtgggag   2460

tccaatggac agcccgagaa caattataag acaacacctc ccgtcctgga ctccgatgga   2520

tcatttttc tgtactccaa gctcaccgtc gataagtcca gatggcagca gggaaatgtc   2580

ttttcctgct ccgtgatgca tgaagctctc cacaatcatt acacacagaa aagcctgtcc   2640

ctgtcccccg gcaagtgact cgag                                          2664
```

<210> SEQ ID NO 55
<211> LENGTH: 2679
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #11

<400> SEQUENCE: 55

```
gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtag agccagccag tggatcggcc ctgagctgag ctggtatcag    180

cagaagcccg gcaaggcccc caagctgctg atctaccaca ccagcatcct gcagagcggc    240

gtgcccagca gattttctgg cagcggcagc ggcaccgact tcaccctgac aatcagcagc    300

ctgcagcccg aggacttcgc cacctactac tgccagcagt acatgttcca gccccggacc    360

tttggccagg gcaccaaggt ggaaatcaga agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gcccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140
```

```
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caatgcagat ttttgtcaag   1440
acactgaccg ggaaaacaat cacactcgaa gtcgagccct ccgatacaat tgagaatgtg   1500
aaagccaaaa ttcaggacaa agaagggatt cctcctgatc agcagcggct gatttttgcc   1560
ggaaaacagc tcgaagatgg acggaccctg tccgattaca atattcagaa agaaagcacc   1620
ctccatctgg tcctgaggct gcggggaggc gacattcaga tgacacagtc ccccacctcc   1680
ctgtctgcca gcgtgggaga tcgcgtgacc attacatgcc gggcctccca gtggattggc   1740
aacctgctgg attggtatca gcagaaacct ggggaggctc ctaaactgct gatctattac   1800
gccagctttc tgcagtccgg cgtgccctcc agattcagcg gcggaggctt cggcacagat   1860
ttcacactga ccatctcatc cctgcagcct gaagattttg ccacatatta ttgccagcag   1920
gccaaccctg ccccctgac attcggccag ggaacaaagg tcgagatcaa gcgcgagccc   1980
aagtcctgtg ataagacaca tacctgcccc ccctgcccag ctccagaact gctcggagga   2040
ccttctgtgt ttctgtttcc acccaagcct aaggatacac tcatgatctc cagaacacct   2100
gaagtgacat gtgtggtcgt cgacgtgtca catgaggatc cagaagtcaa gtttaactgg   2160
tatgtggatg gggtcgaggt gcacaatgcc aaaacaaaac ctcgggaaga acagtataat   2220
tccacctata gagtcgtgtc tgtgctcacc gtgctccatc aggattggct caatgggaaa   2280
gaatacaaat gtaaagtctc taacaaagcc ctgcccgctc ctatcgaaaa gacaatctcc   2340
aaggccaaag gacagcctcg cgagcctcag gtctacaccc tgccacctag ccgcgaggaa   2400
atgacaaaaa atcaggtgtc actcacctgt ctcgtgaagg ggttttaccc ctccgacatt   2460
gccgtcgagt gggagtccaa tggacagccc gagaacaatt ataagacaac acctcccgtc   2520
ctggactccg atggatcatt ttttctgtac tccaagctca ccgtcgataa gtccagatgg   2580
cagcagggaa atgtcttttc ctgctccgtg atgcatgaag ctctccacaa tcattacaca   2640
cagaaaagcc tgtccctgtc ccccggcaag tgactcgag                          2679
```

<210> SEQ ID NO 56
<211> LENGTH: 2694
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #12

<400> SEQUENCE: 56

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtag agccagccag tggatcggcc ctgagctgag ctggtatcag    180
cagaagcccg gcaaggcccc caagctgctg atctaccaca ccagcatcct gcagagcggc    240
gtgcccagca gattttctgg cagcggcagc ggcaccgact tcaccctgac aatcagcagc    300
ctgcagcccg aggacttcgc cacctactac tgccagcagt acatgttcca gccccggacc    360
tttggccagg gcaccaaggt ggaaatcaga agagagccca agagctgcga caagacccac    420
```

-continued

```
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caggcggagg cggatcaatg   1440
cagatttttg tcaagacact gaccgggaaa acaatcacac tcgaagtcga gccctccgat   1500
acaattgaga atgtgaaagc caaaattcag gacaaagaag ggattcctcc tgatcagcag   1560
cggctgattt ttgccggaaa acagctcgaa gatggacgga ccctgtccga ttacaatatt   1620
cagaaagaaa gcaccctcca tctggtcctg aggctgcggg gaggcgacat tcagatgaca   1680
cagtccccca cctccctgtc tgccagcgtg ggagatcgcg tgaccattac atgccgggcc   1740
tcccagtgga ttggcaacct gctggattgg tatcagcaga aacctgggga ggctcctaaa   1800
ctgctgatct attacgccag ctttctgcag tccggcgtgc cctccagatt cagcggcgga   1860
ggcttcggca cagatttcac actgaccatc tcatccctgc agcctgaaga ttttgccaca   1920
tattattgcc agcaggccaa ccctgccccc ctgacattcg gccagggaac aaaggtcgag   1980
atcaagcgcg agcccaagtc ctgtgataag acacatacct gccccccctg cccagctcca   2040
gaactgctcg gaggaccttc tgtgtttctg tttccaccca agcctaagga tacactcatg   2100
atctccagaa cacctgaagt gacatgtgtg gtcgtcgacg tgtcacatga ggatccagaa   2160
gtcaagttta actggtatgt ggatggggtc gaggtgcaca atgccaaaac aaaacctcgg   2220
gaagaacagt ataattccac ctatagagtc gtgtctgtgc tcaccgtgct ccatcaggat   2280
tggctcaatg ggaaagaata caaatgtaaa gtctctaaca aagccctgcc cgctcctatc   2340
gaaaagacaa tctccaaggc caaaggacag cctcgcgagc ctcaggtcta caccctgcca   2400
cctagccgcg aggaaatgac aaaaaatcag gtgtcactca cctgtctcgt gaaggggttt   2460
taccccctccg acattgccgt cgagtgggag tccaatggac agcccgagaa caattataag   2520
acaacacctc ccgtcctgga ctccgatgga tcattttttc tgtactccaa gctcaccgtc   2580
gataagtcca gatggcagca gggaaatgtc ttttcctgct ccgtgatgca tgaagctctc   2640
cacaatcatt acacacagaa aagcctgtcc ctgtccccccg gcaagtgact cgag         2694
```

<210> SEQ ID NO 57

-continued

<211> LENGTH: 2709
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #13

<400> SEQUENCE: 57
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtag agccagccag tggatcggcc ctgagctgag ctggtatcag 180
cagaagcccg gcaaggcccc caagctgctg atctaccaca ccagcatcct gcagagcggc 240
gtgcccagca gattttctgg cagcggcagc ggcaccgact tcaccctgac aatcagcagc 300
ctgcagcccg aggacttcgc cacctactac tgccagcagt acatgttcca gccccggacc 360
tttggccagg gcaccaaggt ggaaatcaga agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caggcggagg cggatcaggt 1440
ggcggcggaa gtatgcagat ttttgtcaag acactgaccg ggaaaacaat cacactcgaa 1500
gtcgagccct ccgatacaat tgagaatgtg aaagccaaaa ttcaggacaa agaagggatt 1560
cctcctgatc agcagcggct gatttttgcc ggaaaacagc tcgaagatgg acggaccctg 1620
tccgattaca atattcagaa agaaagcacc ctccatctgg tcctgaggct gcggggaggc 1680
gacattcaga tgacacagtc ccccacctcc ctgtctgcca gcgtgggaga tcgcgtgacc 1740
attacatgcc gggcctccca gtggattggc aacctgctgg attggtatca gcagaaacct 1800
ggggaggctc ctaaactgct gatctattac gccagctttc tgcagtccgg cgtgccctcc 1860
agattcagcg gcggaggctt cggcacagat ttcacactga ccatctcatc cctgcagcct 1920
gaagattttg ccacatatta ttgccagcag gccaaccctg ccccccctgac attcggccag 1980 ggaacaaagg tcgagatcaa gcgcgagccc aagtcctgtg ataagacaca tacctgcccc 2040

```
ccctgcccag ctccagaact gctcggagga ccttctgtgt ttctgtttcc acccaagcct   2100

aaggatacac tcatgatctc cagaacacct gaagtgacat gtgtggtcgt cgacgtgtca   2160

catgaggatc cagaagtcaa gtttaactgg tatgtggatg ggtcgaggt gcacaatgcc    2220

aaaacaaaac ctcgggaaga acagtataat tccacctata gagtcgtgtc tgtgctcacc   2280

gtgctccatc aggattggct caatgggaaa gaatacaaat gtaaagtctc taacaaagcc   2340

ctgcccgctc ctatcgaaaa gacaatctcc aaggccaaag gacagcctcg cgagcctcag   2400

gtctacaccc tgccacctag ccgcgaggaa atgacaaaaa atcaggtgtc actcacctgt   2460

ctcgtgaagg ggttttaccc ctccgacatt gccgtcgagt gggagtccaa tggacagccc   2520

gagaacaatt ataagacaac acctcccgtc ctggactccg atggatcatt ttttctgtac   2580

tccaagctca ccgtcgataa gtccagatgg cagcagggaa atgtcttttc ctgctccgtg   2640

atgcatgaag ctctccacaa tcattacaca cagaaaagcc tgtccctgtc ccccggcaag   2700

tgactcgag                                                           2709
```

<210> SEQ ID NO 58
<211> LENGTH: 2724
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #14

<400> SEQUENCE: 58

```
gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtag agccagccag tggatcggcc ctgagctgag ctggtatcag    180

cagaagcccg gcaaggcccc caagctgctg atctaccaca ccagcatcct gcagagcggc    240

gtgcccagca gattttctgg cagcggcagc ggcaccgact tcaccctgac aatcagcagc    300

ctgcagcccg aggacttcgc cacctactac tgccagcagt acatgttcca gccccggacc    360

tttggccagg gcaccaaggt ggaaatcaga agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gcccccccagc agagaagaga tgaccaagaa ccaggtgtcc   840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200
```

-continued cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caggcggagg cggatcaggt 1440
ggcggcggaa gtggcggagg cggcagcatg cagatttttg tcaagacact gaccgggaaa 1500
acaatcacac tcgaagtcga gccctccgat acaattgaga atgtgaaagc caaaattcag 1560
gacaaagaag ggattcctcc tgatcagcag cggctgattt ttgccggaaa acagctcgaa 1620
gatggacgga ccctgtccga ttacaatatt cagaaagaaa gcaccctcca tctggtcctg 1680
aggctgcggg gaggcgacat tcagatgaca cagtccccca cctccctgtc tgccagcgtg 1740
ggagatcgcg tgaccattac atgccgggcc tcccagtgga ttggcaacct gctggattgg 1800
tatcagcaga aacctgggga ggctcctaaa ctgctgatct attacgccag ctttctgcag 1860
tccggcgtgc cctccagatt cagcggcgga ggcttcggca cagatttcac actgaccatc 1920
tcatccctgc agcctgaaga ttttgccaca tattattgcc agcaggccaa ccctgccccc 1980
ctgacattcg gccagggaac aaaggtcgag atcaagcgcg agcccaagtc ctgtgataag 2040
acacatacct gccccccctg cccagctcca gaactgctcg gaggaccttc tgtgtttctg 2100
tttccaccca agcctaagga tacactcatg atctccagaa cacctgaagt gacatgtgtg 2160
gtcgtcgacg tgtcacatga ggatccagaa gtcaagttta actggtatgt ggatggggtc 2220
gaggtgcaca atgccaaaac aaaacctcgg gaagaacagt ataattccac ctatagagtc 2280
gtgtctgtgc tcaccgtgct ccatcaggat tggctcaatg ggaaagaata caaatgtaaa 2340
gtctctaaca aagccctgcc cgctcctatc gaaaagacaa tctccaaggc caaaggacag 2400
cctcgcgagc ctcaggtcta caccctgcca cctagccgcg aggaaatgac aaaaaatcag 2460
gtgtcactca cctgtctcgt gaaggggttt taccccctccg acattgccgt cgagtgggag 2520
tccaatggac agcccgagaa caattataag acaacacctc ccgtcctgga ctccgatgga 2580
tcattttttc tgtactccaa gctcaccgtc gataagtcca gatggcagca gggaaatgtc 2640
ttttcctgct ccgtgatgca tgaagctctc cacaatcatt acacacagaa aagcctgtcc 2700
ctgtcccccg gcaagtgact cgag 2724

<210> SEQ ID NO 59
<211> LENGTH: 2634
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #15

<400> SEQUENCE: 59
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420

```
acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtatg   1380

cagatttttg tcaagacact gaccgggaaa acaatcacac tcgaagtcga gccctccgat   1440

acaattgaga atgtgaaagc caaaattcag gacaaagaag ggattcctcc tgatcagcag   1500

cggctgattt ttgccggaaa acagctcgaa gatggacgga ccctgtccga ttacaatatt   1560

cagaaagaaa gcaccctcca tctggtcctg aggctgcggg gaggcgacat tcagatgaca   1620

cagtccccca gctccctgag cgccagcgtg ggagatcgcg tgaccattac ctgcagagcc   1680

tcccagtgga tcggcatcct ggtggattgg tatcagcaga aacctgggga ggctcctaaa   1740

ctgctgatct attacgccag cttcctgcag tccggcgtgc cctctagatt cagcggctct   1800

ggcttcggca cagatttcac actgaccatc tctagcctgc accctgaaga ttttgccaca   1860

tattactgtc agcaggccaa ccctgccccc ctgacatttg gacagggaac aaaggtcgag   1920

atcaagcgcg agcctaagtc ctgtgacaag acacacacat gccctccctg cccagcccca   1980

gaactgctcg gtggaccctc tgtgtttctg tttccaccca agcctaagga tacactcatg   2040

atctccagaa cacctgaagt gacatgtgtg gtcgtcgacg tgtcacatga ggatccagaa   2100

gtcaagttta actggtatgt ggatggggtc gaggtgcaca atgccaaaac aaaacctcgg   2160

gaagaacagt ataattccac ctatagagtc gtgtctgtgc tcaccgtgct ccatcaggat   2220

tggctcaatg ggaaagaata caaatgtaaa gtctctaaca aagccctgcc cgctcctatc   2280

gaaaagacaa tctccaaggc caaaggacag cctcgcgagc ctcaggtcta caccctgcca   2340

ccttcccgcg aggaaatgac aaaaaatcag gtgtcactca cctgtctcgt gaaggggttt   2400

tacccctccg acattgccgt cgagtgggag tccaatggac agcccgagaa caattataag   2460

acaacacctc ccgtcctgga ctccgatgga tcatttttc tgtactccaa gctcaccgtc    2520

gataagtcca gatggcagca gggaaatgtc ttttcctgct ccgtgatgca tgaagctctc   2580

cacaatcatt acacacagaa aagcctgtcc ctgtccccg gcaagtgact cgag          2634
```

<210> SEQ ID NO 60
<211> LENGTH: 2649
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #16

<400> SEQUENCE: 60

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg tcctgctgta cccctacacc    360
tttggccagg gcaccaaggt ggaaatcaag agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtatgcagat ttttgtcaag acactgaccg ggaaaacaat cacactcgaa   1440
gtcgagccct ccgatacaat tgagaatgtg aaagccaaaa ttcaggacaa agaagggatt   1500
cctcctgatc agcagcggct gatttttgcc ggaaaacagc tcgaagatgg acggaccctg   1560
tccgattaca atattcagaa agaaagcacc ctccatctgg tcctgaggct gcggggaggc   1620
gacattcaga tgacacagtc cccagctcc ctgagcgcca gcgtgggaga tcgcgtgacc   1680
attacctgca gagcctccca gtggatcggc atcctggtgg attggtatca gcagaaacct   1740
ggggaggctc ctaaactgct gatctattac gccagcttcc tgcagtccgg cgtgccctct   1800
agattcagcg gctctggctt cggcacagat ttcacactga ccatctctag cctgcaccct   1860
gaagattttg ccacatatta ctgtcagcag gccaaccctg cccccctgac atttggacag   1920
ggaacaaagg tcgagatcaa gcgcgagcct aagtcctgtg acaagacaca cacatgccct   1980
ccctgcccag ccccagaact gctcggtgga ccctctgtgt ttctgtttcc acccaagcct   2040
aaggatacac tcatgatctc cagaacacct gaagtgacat gtgtggtcgt cgacgtgtca   2100
```

```
catgaggatc cagaagtcaa gtttaactgg tatgtggatg gggtcgaggt gcacaatgcc   2160

aaaacaaaac ctcgggaaga acagtataat tccacctata gagtcgtgtc tgtgctcacc   2220

gtgctccatc aggattggct caatgggaaa gaatacaaat gtaaagtctc taacaaagcc   2280

ctgcccgctc ctatcgaaaa gacaatctcc aaggccaaag gacagcctcg cgagcctcag   2340

gtctacaccc tgccaccttc ccgcgaggaa atgacaaaaa atcaggtgtc actcacctgt   2400

ctcgtgaagg ggttttaccc ctccgacatt gccgtcgagt gggagtccaa tggacagccc   2460

gagaacaatt ataagacaac acctcccgtc ctggactccg atggatcatt ttttctgtac   2520

tccaagctca ccgtcgataa gtccagatgg cagcagggaa atgtcttttc ctgctccgtg   2580

atgcatgaag ctctccacaa tcattacaca cagaaaagcc tgtccctgtc ccccggcaag   2640

tgactcgag                                                           2649
```

<210> SEQ ID NO 61
<211> LENGTH: 2664
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #17

<400> SEQUENCE: 61

```
gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gcccccagc agagaagaga tgaccaagaa ccaggtgtcc     840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320
```

```
ggtggtggtt ctggtggcgg aggatctggc ggtggtggat ctgggggagg tggaagtggt   1380

ggcggtggta gtggtggtgg cggaagcatg cagatttttg tcaagacact gaccgggaaa   1440

acaatcacac tcgaagtcga gccctccgat acaattgaga atgtgaaagc caaaattcag   1500

gacaaagaag ggattcctcc tgatcagcag cggctgattt ttgccggaaa acagctcgaa   1560

gatggacgga ccctgtccga ttacaatatt cagaaagaaa gcaccctcca tctggtcctg   1620

aggctgcggg gaggcgacat tcagatgaca cagtccccca gctccctgag cgccagcgtg   1680

ggagatcgcg tgaccattac ctgcagagcc tcccagtgga tcggcatcct ggtggattgg   1740

tatcagcaga aacctgggga ggctcctaaa ctgctgatct attacgccag cttcctgcag   1800

tccggcgtgc cctctagatt cagcggctct ggcttcggca cagatttcac actgaccatc   1860

tctagcctgc accctgaaga ttttgccaca tattactgtc agcaggccaa ccctgccccc   1920

ctgacatttg gacagggaac aaaggtcgag atcaagcgcg agcctaagtc ctgtgacaag   1980

acacacacat gccctccctg cccagcccca gaactgctcg gtggaccctc tgtgtttctg   2040

tttccaccca agcctaagga tacactcatg atctccagaa cacctgaagt gacatgtgtg   2100

gtcgtcgacg tgtcacatga ggatccagaa gtcaagttta actggtatgt ggatggggtc   2160

gaggtgcaca atgccaaaac aaaacctcgg gaagaacagt ataattccac ctatagagtc   2220

gtgtctgtgc tcaccgtgct ccatcaggat tggctcaatg ggaaagaata caaatgtaaa   2280

gtctctaaca aagccctgcc cgctcctatc gaaaagacaa tctccaaggc caaaggacag   2340

cctcgcgagc ctcaggtcta caccctgcca ccttcccgcg aggaaatgac aaaaaatcag   2400

gtgtcactca cctgtctcgt gaaggggttt taccccctccg acattgccgt cgagtgggag   2460

tccaatggac agcccgagaa caattataag acaacacctc ccgtcctgga ctccgatgga   2520

tcatttttttc tgtactccaa gctcaccgtc gataagtcca gatggcagca gggaaatgtc   2580

ttttcctgct ccgtgatgca tgaagctctc cacaatcatt acacacagaa aagcctgtcc   2640

ctgtcccccg gcaagtgact cgag                                          2664
```

```
<210> SEQ ID NO 62
<211> LENGTH: 2679
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #18

<400> SEQUENCE: 62

gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600
```

```
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc cccctgtgc tggacagcga cggctcattc     960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caatgcagat ttttgtcaag   1440
acactgaccg ggaaaacaat cacactcgaa gtcgagccct ccgatacaat tgagaatgtg   1500
aaagccaaaa ttcaggacaa agaagggatt cctcctgatc agcagcggct gatttttgcc   1560
ggaaaacagc tcgaagatgg acggaccctg tccgattaca atattcagaa agaaagcacc   1620
ctccatctgg tcctgaggct gcggggaggc gacattcaga tgacacagtc cccagctcc    1680
ctgagcgcca gcgtgggaga tcgcgtgacc attacctgca gagcctccca gtggatcggc   1740
atcctggtgg attggtatca gcagaaacct ggggaggctc ctaaactgct gatctattac   1800
gccagcttcc tgcagtccgg cgtgccctct agattcagcg gctctggctt cggcacagat   1860
ttcacactga ccatctctag cctgcaccct gaagattttg ccacatatta ctgtcagcag   1920
gccaaccctg cccccctgac atttggacag ggaacaaagg tcgagatcaa gcgcgagcct   1980
aagtcctgtg acaagacaca cacatgccct ccctgcccag ccccagaact gctcggtgga   2040
ccctctgtgt ttctgtttcc acccaagcct aaggatacac tcatgatctc cagaacacct   2100
gaagtgacat gtgtggtcgt cgacgtgtca catgaggatc cagaagtcaa gtttaactgg   2160
tatgtggatg gggtcgaggt gcacaatgcc aaaacaaaac ctcgggaaga acagtataat   2220
tccacctata gagtcgtgtc tgtgctcacc gtgctccatc aggattggct caatgggaaa   2280
gaatacaaat gtaaagtctc taacaaagcc ctgcccgctc ctatcgaaaa gacaatctcc   2340
aaggccaaag gacagcctcg cgagcctcag gtctacaccc tgccaccttc ccgcgaggaa   2400
atgacaaaaa atcaggtgtc actcacctgt ctcgtgaagg ggttttaccc ctccgacatt   2460
gccgtcgagt gggagtccaa tggacagccc gagaacaatt ataagacaac acctcccgtc   2520
ctggactccg atggatcatt ttttctgtac tccaagctca ccgtcgataa gtccagatgg   2580
cagcagggaa atgtcttttc ctgctccgtg atgcatgaag ctctccacaa tcattacaca   2640
cagaaaagcc tgtccctgtc ccccggcaag tgactcgag                          2679
```

<210> SEQ ID NO 63
<211> LENGTH: 2694
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: Nucleotide sequence encoding the protein
complex comprising VEGF and EGFR specific binding peptides #19

<400> SEQUENCE: 63

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gatttctgg cagcggcagc ggcaccgact tcaccctgac aatcagcagc     300
ctgcagcccg aggacttcgc cacctactac tgccagcagg tcctgctgta cccctacacc    360
tttggccagg gcaccaaggt ggaaatcaag agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caggcggagg cggatcaatg   1440
cagatttttg tcaagacact gaccgggaaa acaatcacac tcgaagtcga gccctccgat   1500
acaattgaga atgtgaaagc caaaattcag gacaaagaag ggattcctcc tgatcagcag   1560
cggctgattt ttgccggaaa acagctcgaa gatggacgga ccctgtccga ttacaatatt   1620
cagaaagaaa gcaccctcca tctggtcctg aggctgcggg gaggcgacat tcagatgaca   1680
cagtccccca gctccctgag cgccagcgtg ggagatcgcg tgaccattac ctgcagagcc   1740
tcccagtgga tcggcatcct ggtggattgg tatcagcaga aacctgggga ggctcctaaa   1800
ctgctgatct attacgccag cttcctgcag tccggcgtgc cctctagatt cagcggctct   1860
ggcttcggca cagatttcac actgaccatc tctagcctgc accctgaaga ttttgccaca   1920
tattactgtc agcaggccaa ccctgccccc ctgacatttg gacagggaac aaaggtcgag   1980
atcaagcgcg agcctaagtc ctgtgacaag acacacacat gccctccctg cccagcccca   2040
gaactgctcg gtggaccctc tgtgtttctg tttccaccca agcctaagga tacactcatg   2100
atctccagaa cacctgaagt gacatgtgtg gtcgtcgacg tgtcacatga ggatccagaa   2160
gtcaagttta actggtatgt ggatggggtc gaggtgcaca atgccaaaac aaaacctcgg   2220
```

```
gaagaacagt ataattccac ctatagagtc gtgtctgtgc tcaccgtgct ccatcaggat   2280

tggctcaatg ggaaagaata caaatgtaaa gtctctaaca aagccctgcc cgctcctatc   2340

gaaaagacaa tctccaaggc caaaggacag cctcgcgagc ctcaggtcta caccctgcca   2400

ccttcccgcg aggaaatgac aaaaaatcag gtgtcactca cctgtctcgt gaaggggttt   2460

taccccctccg acattgccgt cgagtgggag tccaatggac agcccgagaa caattataag   2520

acaacacctc ccgtcctgga ctccgatgga tcatttttc tgtactccaa gctcaccgtc   2580

gataagtcca gatggcagca gggaaatgtc ttttcctgct ccgtgatgca tgaagctctc   2640

cacaatcatt acacacagaa aagcctgtcc ctgtcccccg gcaagtgact cgag          2694
```

<210> SEQ ID NO 64
<211> LENGTH: 2709
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #20

<400> SEQUENCE: 64

```
gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gcccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtggt   1380

ggcggtggta gtggtggtgg cggaagcgga ggcggtggat caggcggagg cggatcaggt   1440
```

ggcgggggtt caatgcagat ttttgtcaag acactgaccg ggaaaacaat cacactcgaa 1500
gtcgagccct ccgatacaat tgagaatgtg aaagccaaaa ttcaggacaa agaagggatt 1560
cctcctgatc agcagcggct gatttttgcc ggaaaacagc tcgaagatgg acggaccctg 1620
tccgattaca atattcagaa agaaagcacc ctccatctgg tcctgaggct gcggggaggc 1680
gacattcaga tgacacagtc ccccagctcc ctgagcgcca gcgtgggaga tcgcgtgacc 1740
attacctgca gagcctccca gtggatcggc atcctggtgg attggtatca gcagaaacct 1800
ggggaggctc ctaaactgct gatctattac gccagcttcc tgcagtccgg cgtgccctct 1860
agattcagcg gctctggctt cggcacagat ttcacactga ccatctctag cctgcaccct 1920
gaagattttg ccacatatta ctgtcagcag gccaaccctg ccccctgac atttggacag 1980 ggaacaaagg tcgagatcaa gcgcgagcct aagtcctgtg acaagacaca cacatgccct 2040
ccctgcccag ccccagaact gctcggtgga ccctctgtgt ttctgtttcc acccaagcct 2100
aaggatacac tcatgatctc cagaacacct gaagtgacat gtgtggtcgt cgacgtgtca 2160
catgaggatc cagaagtcaa gtttaactgg tatgtggatg gggtcgaggt gcacaatgcc 2220
aaaacaaaac ctcgggaaga acagtataat tccacctata gagtcgtgtc tgtgctcacc 2280
gtgctccatc aggattggct caatgggaaa gaatacaaat gtaaagtctc taacaaagcc 2340
ctgcccgctc ctatcgaaaa gacaatctcc aaggccaaag gacagcctcg cgagcctcag 2400
gtctacaccc tgccaccttc ccgcgaggaa atgacaaaaa atcaggtgtc actcacctgt 2460
ctcgtgaagg ggttttaccc ctccgacatt gccgtcgagt gggagtccaa tggacagccc 2520
gagaacaatt ataagacaac acctcccgtc ctggactccg atggatcatt ttttctgtac 2580
tccaagctca ccgtcgataa gtccagatgg cagcagggaa atgtcttttc ctgctccgtg 2640
atgcatgaag ctctccacaa tcattacaca cagaaaagcc tgtccctgtc ccccggcaag 2700
tgactcgag 2709

<210> SEQ ID NO 65
<211> LENGTH: 2724
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #21

<400> SEQUENCE: 65
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660

-continued

```
gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtggt   1380

ggcggtggta gtggtggtgg cggaagcgga ggcggtggat caggcggagg cggatcaggt   1440

ggcgggggtt cagggggtgg cggaagtatg cagatttttg tcaagacact gaccgggaaa   1500

acaatcacac tcgaagtcga gccctccgat acaattgaga atgtgaaagc caaaattcag   1560

gacaaagaag ggattcctcc tgatcagcag cggctgattt ttgccggaaa acagctcgaa   1620

gatggacgga ccctgtccga ttacaatatt cagaaagaaa gcaccctcca tctggtcctg   1680

aggctgcggg gaggcgacat tcagatgaca cagtccccca gctccctgag cgccagcgtg   1740

ggagatcgcg tgaccattac ctgcagagcc tcccagtgga tcggcatcct ggtggattgg   1800

tatcagcaga aacctgggga ggctcctaaa ctgctgatct attacgccag cttcctgcag   1860

tccggcgtgc cctctagatt cagcggctct ggcttcggca cagatttcac actgaccatc   1920

tctagcctgc accctgaaga ttttgccaca tattactgtc agcaggccaa ccctgccccc   1980

ctgacatttg gacagggaac aaaggtcgag atcaagcgcg agcctaagtc ctgtgacaag   2040

acacacacat gccctccctg cccagcccca gaactgctcg gtggaccctc tgtgtttctg   2100

tttccaccca agcctaagga tacactcatg atctccagaa cacctgaagt gacatgtgtg   2160

gtcgtcgacg tgtcacatga ggatccagaa gtcaagttta actggtatgt ggatggggtc   2220

gaggtgcaca atgccaaaac aaaacctcgg gaagaacagt ataattccac ctatagagtc   2280

gtgtctgtgc tcaccgtgct ccatcaggat tggctcaatg ggaaagaata caaatgtaaa   2340

gtctctaaca aagccctgcc cgctcctatc gaaaagacaa tctccaaggc caaaggacag   2400

cctcgcgagc ctcaggtcta caccctgcca ccttcccgcg aggaaatgac aaaaaatcag   2460

gtgtcactca cctgtctcgt gaaggggttt taccoctccg acattgccgt cgagtgggag   2520

tccaatggac agcccgagaa caattataag acaacacctc ccgtcctgga ctccgatgga   2580

tcatttttc tgtactccaa gctcaccgtc gataagtcca gatggcagca gggaaatgtc   2640

ttttcctgct ccgtgatgca tgaagctctc cacaatcatt acacacagaa aagcctgtcc   2700

ctgtcccccg gcaagtgact cgag                                          2724
```

<210> SEQ ID NO 66
<211> LENGTH: 2634
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: Nucleotide sequence encoding the protein
      complex comprising VEGF and EGFR specific binding peptides #22

<400> SEQUENCE: 66
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gatttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc cccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtatg 1380 cagattttg tcaagacact gaccgggaaa acaatcacac tcgaagtcga gccctccgat 1440
acaattgaga atgtgaaagc caaaattcag gacaaagaag ggattcctcc tgatcagcag 1500
cggctgattt ttgccggaaa acagctcgaa gatggacgga ccctgtccga ttacaatatt 1560
cagaaagaaa gcaccctcca tctggtcctg aggctgcggg gaggcgacat tcagatgaca 1620
cagtccccca cctccctgtc tgccagcgtg ggagatcgcg tgaccattac ctgcagagcc 1680
tcccagtgga tcggcaacct gctggattgg tatcagcaga aacctgggga ggctcctaaa 1740
ctgctgatct attacgccag cttcctgcag tccggcgtgc cctctagatt ttccggcgga 1800
ggcttcggca cagatttcac actgaccatc tcatccctgc agcctgaaga ttttgccaca 1860
tattattgcc agcaggccaa ccctgccccc ctgacatttg gacagggaac aaaggtcgag 1920
atcaagcgcg agcctaagtc ctgtgacaag acacacacat gccctccctg cccagcccca 1980
gaactgctcg gtggaccctc tgtgtttctg tttccaccca agcctaagga tacactcatg 2040
atctccagaa cacctgaagt gacatgtgtg gtcgtcgacg tgtcacatga ggatccagaa 2100
gtcaagttta actggtatgt ggatggggtc gaggtgcaca atgccaaaac aaaacctcgg 2160
gaagaacagt ataattccac ctatagagtc gtgtctgtgc tcaccgtgct ccatcaggat 2220

```
tggctcaatg ggaaagaata caaatgtaaa gtctctaaca aagccctgcc cgctcctatc   2280

gaaaagacaa tctccaaggc caaaggacag cctcgcgagc ctcaggtcta caccctgcca   2340

ccttcccgcg aggaaatgac aaaaaatcag gtgtcactca cctgtctcgt gaaggggttt   2400

tacccctccg acattgccgt cgagtgggag tccaatggac agcccgagaa caattataag   2460

acaacacctc ccgtcctgga ctccgatgga tcatttttc tgtactccaa gctcaccgtc   2520

gataagtcca gatggcagca gggaaatgtc ttttcctgct ccgtgatgca tgaagctctc   2580

cacaatcatt acacacagaa aagcctgtcc ctgtccccg gcaagtgact cgag          2634
```

<210> SEQ ID NO 67
<211> LENGTH: 2649
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #23

<400> SEQUENCE: 67

```
gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtggt   1380

ggcggtggta gtatgcagat ttttgtcaag acactgaccg ggaaaacaat cacactcgaa   1440

gtcgagccct ccgatacaat tgagaatgtg aaagccaaaa ttcaggacaa agaagggatt   1500
```

```
cctcctgatc agcagcggct gatttttgcc ggaaaacagc tcgaagatgg acggaccctg   1560

tccgattaca atattcagaa agaaagcacc ctccatctgg tcctgaggct gcggggaggc   1620

gacattcaga tgacacagtc cccccacctcc ctgtctgcca gcgtgggaga tcgcgtgacc   1680

attacctgca gagcctccca gtggatcggc aacctgctgg attggtatca gcagaaacct   1740

ggggaggctc ctaaactgct gatctattac gccagcttcc tgcagtccgg cgtgccctct   1800

agattttccg gcggaggctt cggcacagat ttcacactga ccatctcatc cctgcagcct   1860

gaagattttg ccacatatta ttgccagcag gccaaccctg cccccctgac atttggacag   1920

ggaacaaagg tcgagatcaa gcgcgagcct aagtcctgtg acaagacaca cacatgccct   1980

ccctgcccag ccccagaact gctcggtgga ccctctgtgt ttctgtttcc acccaagcct   2040

aaggatacac tcatgatctc cagaacacct gaagtgacat gtgtggtcgt cgacgtgtca   2100

catgaggatc cagaagtcaa gtttaactgg tatgtggatg gggtcgaggt gcacaatgcc   2160

aaaacaaaac ctcgggaaga acagtataat tccacctata gagtcgtgtc tgtgctcacc   2220

gtgctccatc aggattggct caatgggaaa gaatacaaat gtaaagtctc taacaaagcc   2280

ctgcccgctc ctatcgaaaa gacaatctcc aaggccaaag gacagcctcg cgagcctcag   2340

gtctacaccc tgccaccttc ccgcgaggaa atgacaaaaa atcaggtgtc actcacctgt   2400

ctcgtgaagg ggttttaccc ctccgacatt gccgtcgagt gggagtccaa tggacagccc   2460

gagaacaatt ataagacaac acctcccgtc ctggactccg atggatcatt ttttctgtac   2520

tccaagctca ccgtcgataa gtccagatgg cagcagggaa atgtcttttc ctgctccgtg   2580

atgcatgaag ctctccacaa tcattacaca cagaaaagcc tgtccctgtc ccccggcaag   2640

tgactcgag                                                            2649
```

```
<210> SEQ ID NO 68
<211> LENGTH: 2664
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #24

<400> SEQUENCE: 68

gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780
```

```
gaaccccagg tgtacacact gcccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc cccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtggt   1380

ggcggtggta gtggtggtgg cggaagcatg cagatttttg tcaagacact gaccgggaaa   1440

acaatcacac tcgaagtcga gccctccgat acaattgaga atgtgaaagc caaaattcag   1500

gacaaagaag ggattcctcc tgatcagcag cggctgattt ttgccggaaa acagctcgaa   1560

gatggacgga ccctgtccga ttacaatatt cagaaagaaa gcaccctcca tctggtcctg   1620

aggctgcggg gaggcgacat tcagatgaca cagtccccca cctccctgtc tgccagcgtg   1680

ggagatcgcg tgaccattac ctgcagagcc tcccagtgga tcggcaacct gctggattgg   1740

tatcagcaga aacctgggga ggctcctaaa ctgctgatct attacgccag cttcctgcag   1800

tccggcgtgc cctctagatt ttccggcgga ggcttcggca cagatttcac actgaccatc   1860

tcatccctgc agcctgaaga ttttgccaca tattattgcc agcaggccaa ccctgccccc   1920

ctgacatttg gacagggaac aaaggtcgag atcaagcgcg agcctaagtc ctgtgacaag   1980

acacacacat gccctccctg cccagcccca gaactgctcg gtggaccctc tgtgtttctg   2040

tttccaccca agcctaagga tacactcatg atctccagaa cacctgaagt gacatgtgtg   2100

gtcgtcgacg tgtcacatga ggatccagaa gtcaagttta actggtatgt ggatggggtc   2160

gaggtgcaca atgccaaaac aaaacctcgg gaagaacagt ataattccac ctatagagtc   2220

gtgtctgtgc tcaccgtgct ccatcaggat tggctcaatg ggaaagaata caaatgtaaa   2280

gtctctaaca aagccctgcc cgctcctatc gaaaagacaa tctccaaggc caaaggacag   2340

cctcgcgagc ctcaggtcta caccctgcca ccttcccgcg aggaaatgac aaaaaatcag   2400

gtgtcactca cctgtctcgt gaaggggttt taccccctccg acattgccgt cgagtgggag   2460

tccaatggac agcccgagaa caattataag acaacacctc ccgtcctgga ctccgatgga   2520

tcattttttc tgtactccaa gctcaccgtc gataagtcca gatggcagca gggaaatgtc   2580

ttttcctgct ccgtgatgca tgaagctctc cacaatcatt acacacagaa aagcctgtcc   2640

ctgtcccccg gcaagtgact cgag                                           2664
```

<210> SEQ ID NO 69
<211> LENGTH: 2679
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #25

<400> SEQUENCE: 69

-continued

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gatttctgg cagcggcagc ggcaccgact tcaccctgac aatcagcagc     300
ctgcagcccg aggacttcgc cacctactac tgccagcagg tcctgctgta cccctacacc    360
tttggccagg gcaccaaggt ggaaatcaag agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctggtggcgg aggatctggc ggtggtggat ctgggggagg tggaagtggt   1380
ggcggtggta gtggtggtgg cggaagcgga ggcggtggat caatgcagat tttgtcaag    1440
acactgaccg ggaaaacaat cacactcgaa gtcgagccct ccgatacaat tgagaatgtg   1500
aaagccaaaa ttcaggacaa agaagggatt cctcctgatc agcagcggct gatttttgcc   1560
ggaaaacagc tcgaagatgg acggaccctg tccgattaca atattcagaa agaaagcacc   1620
ctccatctgg tcctgaggct gcggggaggc gacattcaga tgacacagtc ccccacctcc   1680
ctgtctgcca gcgtgggaga tcgcgtgacc attacctgca gagcctccca gtggatcggc   1740
aacctgctgg attggtatca gcagaaacct ggggaggctc ctaaactgct gatctattac   1800
gccagcttcc tgcagtccgg cgtgccctct agattttccg gcggaggctt cggcacagat   1860
ttcacactga ccatctcatc cctgcagcct gaagattttg ccacatatta ttgccagcag   1920
gccaaccctg cccccctgac atttggacag ggaacaaagg tcgagatcaa gcgcgagcct   1980
aagtcctgtg acaagacaca cacatgccct ccctgcccag ccccagaact gctcggtgga   2040
ccctctgtgt ttctgtttcc acccaagcct aaggatacac tcatgatctc cagaacacct   2100
gaagtgacat gtgtggtcgt cgacgtgtca catgaggatc cagaagtcaa gtttaactgg   2160
tatgtggatg gggtcgaggt gcacaatgcc aaaacaaaac ctcgggaaga acagtataat   2220
tccacctata gagtcgtgtc tgtgctcacc gtgctccatc aggattggct caatgggaaa   2280
gaatacaaat gtaaagtctc taacaaagcc ctgcccgctc ctatcgaaaa gacaatctcc   2340
aaggccaaag gacagcctcg cgagcctcag gtctacaccc tgccaccttc ccgcgaggaa   2400
```

atgacaaaaa atcaggtgtc actcacctgt ctcgtgaagg ggttttaccc ctccgacatt 2460
gccgtcgagt gggagtccaa tggacagccc gagaacaatt ataagacaac acctcccgtc 2520
ctggactccg atggatcatt ttttctgtac tccaagctca ccgtcgataa gtccagatgg 2580
cagcagggaa atgtcttttc ctgctccgtg atgcatgaag ctctccacaa tcattacaca 2640
cagaaaagcc tgtccctgtc ccccggcaag tgactcgag 2679

<210> SEQ ID NO 70
<211> LENGTH: 2694
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #26

<400> SEQUENCE: 70
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caggcggagg cggatcaatg 1440
cagatttttg tcaagacact gaccgggaaa acaatcacac tcgaagtcga gccctccgat 1500
acaattgaga atgtgaaagc caaaattcag gacaaagaag ggattcctcc tgatcagcag 1560
cggctgattt ttgccggaaa acagctcgaa gatggacgga ccctgtccga ttacaatatt 1620
cagaaagaaa gcaccctcca tctggtcctg aggctgcggg gaggcgacat tcagatgaca 1680
cagtccccca cctccctgtc tgccagcgtg ggagatcgcg tgaccattac ctgcagagcc 1740
tcccagtgga tcggcaacct gctggattgg tatcagcaga aacctgggga ggctcctaaa 1800
ctgctgatct attacgccag cttcctgcag tccggcgtgc cctctagatt ttccggcgga 1860
ggcttcggca cagatttcac actgaccatc tcatccctgc agcctgaaga ttttgccaca 1920
tattattgcc agcaggccaa ccctgccccc ctgacatttg gacagggaac aaaggtcgag 1980
atcaagcgcg agcctaagtc ctgtgacaag acacacacat gccctccctg cccagcccca 2040
gaactgctcg gtggaccctc tgtgtttctg tttccaccca agcctaagga tacactcatg 2100
atctccagaa cacctgaagt gacatgtgtg gtcgtcgacg tgtcacatga ggatccagaa 2160
gtcaagttta actggtatgt ggatggggtc gaggtgcaca atgccaaaac aaaacctcgg 2220
gaagaacagt ataattccac ctatagagtc gtgtctgtgc tcaccgtgct ccatcaggat 2280
tggctcaatg ggaaagaata caaatgtaaa gtctctaaca aagccctgcc cgctcctatc 2340
gaaaagacaa tctccaaggc caaaggacag cctcgcgagc ctcaggtcta caccctgcca 2400
ccttcccgcg aggaaatgac aaaaaatcag gtgtcactca cctgtctcgt gaaggggttt 2460 taccccctccg acattgccgt cgagtgggag tccaatggac agcccgagaa caattataag 2520
acaacacctc ccgtcctgga ctccgatgga tcattttttc tgtactccaa gctcaccgtc 2580
gataagtcca gatggcagca gggaaatgtc ttttcctgct ccgtgatgca tgaagctctc 2640
cacaatcatt acacacagaa aagcctgtcc ctgtcccccg gcaagtgact cgag 2694

<210> SEQ ID NO 71
<211> LENGTH: 2709
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #27

<400> SEQUENCE: 71
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caggcggagg cggatcaggt 1440
ggcgggggtt caatgcagat ttttgtcaag acactgaccg ggaaaacaat cacactcgaa 1500
gtcgagccct ccgatacaat tgagaatgtg aaagccaaaa ttcaggacaa agaagggatt 1560
cctcctgatc agcagcggct gatttttgcc ggaaaacagc tcgaagatgg acggaccctg 1620
tccgattaca atattcagaa agaaagcacc ctccatctgg tcctgaggct gcggggaggc 1680
gacattcaga tgacacagtc ccccacctcc ctgtctgcca gcgtgggaga tcgcgtgacc 1740
attacctgca gagcctccca gtggatcggc aacctgctgg attggtatca gcagaaacct 1800
ggggaggctc ctaaactgct gatctattac gccagcttcc tgcagtccgg cgtgccctct 1860 agatttccg gcggaggctt cggcacagat ttcacactga ccatctcatc cctgcagcct 1920
gaagattttg ccacatatta ttgccagcag gccaaccctg cccccctgac atttggacag 1980
ggaacaaagg tcgagatcaa gcgcgagcct aagtcctgtg acaagacaca cacatgccct 2040
ccctgcccag ccccagaact gctcggtgga ccctctgtgt ttctgtttcc acccaagcct 2100
aaggatacac tcatgatctc cagaacacct gaagtgacat gtgtggtcgt cgacgtgtca 2160
catgaggatc cagaagtcaa gtttaactgg tatgtggatg gggtcgaggt gcacaatgcc 2220
aaaacaaaac ctcgggaaga acagtataat tccacctata gagtcgtgtc tgtgctcacc 2280
gtgctccatc aggattggct caatgggaaa gaatacaaat gtaaagtctc taacaaagcc 2340
ctgcccgctc ctatcgaaaa gacaatctcc aaggccaaag gacagcctcg cgagcctcag 2400
gtctacaccc tgccaccttc ccgcgaggaa atgacaaaaa atcaggtgtc actcacctgt 2460
ctcgtgaagg ggttttaccc ctccgacatt gccgtcgagt gggagtccaa tggacagccc 2520
gagaacaatt ataagacaac acctcccgtc ctggactccg atggatcatt ttttctgtac 2580
tccaagctca ccgtcgataa gtccagatgg cagcagggaa atgtcttttc ctgctccgtg 2640
atgcatgaag ctctccacaa tcattacaca cagaaaagcc tgtccctgtc ccccggcaag 2700
tgactcgag 2709

<210> SEQ ID NO 72
<211> LENGTH: 2724
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #28

<400> SEQUENCE: 72
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagccccaga 780
gaaccccagg tgtacacact gccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcgga ggcggtggat caggcggagg cggatcaggt 1440
ggcgggggtt caggggggtgg cggaagtatg cagatttttg tcaagacact gaccgggaaa 1500
acaatcacac tcgaagtcga gccctccgat acaattgaga atgtgaaagc caaaattcag 1560
gacaaagaag ggattcctcc tgatcagcag cggctgattt ttgccggaaa acagctcgaa 1620
gatggacgga ccctgtccga ttacaatatt cagaaagaaa gcaccctcca tctggtcctg 1680
aggctgcggg gaggcgacat tcagatgaca cagtccccca cctccctgtc tgccagcgtg 1740
ggagatcgcg tgaccattac ctgcagagcc tcccagtgga tcggcaacct gctggattgg 1800
tatcagcaga aacctgggga ggctcctaaa ctgctgatct attacgccag cttcctgcag 1860
tccggcgtgc cctctagatt ttccggcgga ggcttcggca cagatttcac actgaccatc 1920
tcatccctgc agcctgaaga ttttgccaca tattattgcc agcaggccaa ccctgccccc 1980
ctgacatttg gacagggaac aaaggtcgag atcaagcgcg agcctaagtc ctgtgacaag 2040
acacacacat gccctccctg cccagcccca gaactgctcg gtggaccctc tgtgtttctg 2100
tttccaccca agcctaagga tacactcatg atctccagaa cacctgaagt gacatgtgtg 2160
gtcgtcgacg tgtcacatga ggatccagaa gtcaagttta actggtatgt ggatggggtc 2220
gaggtgcaca atgccaaaac aaaacctcgg gaagaacagt ataattccac ctatagagtc 2280
gtgtctgtgc tcaccgtgct ccatcaggat tggctcaatg ggaaagaata caaatgtaaa 2340
gtctctaaca aagccctgcc cgctcctatc gaaaagacaa tctccaaggc caaaggacag 2400
cctcgcgagc ctcaggtcta caccctgcca ccttcccgcg aggaaatgac aaaaaatcag 2460
gtgtcactca cctgtctcgt gaaggggttt taccccctccg acattgccgt cgagtgggag 2520
tccaatggac agcccgagaa caattataag acaacacctc ccgtcctgga ctccgatgga 2580
tcattttttc tgtactccaa gctcaccgtc gataagtcca gatggcagca gggaaatgtc 2640
ttttcctgct ccgtgatgca tgaagctctc cacaatcatt acacacagaa aagcctgtcc 2700
ctgtcccccg gcaagtgact cgag 2724

<210> SEQ ID NO 73
<211> LENGTH: 2664
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #29

<400> SEQUENCE: 73
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcatg cagatttttg tcaagacact gaccgggaaa 1440
acaatcacac tcgaagtcga gccctccgat acaattgaga atgtgaaagc caaaattcag 1500
gacaaagaag ggattcctcc tgatcagcag cggctgattt ttgccggaaa acagctcgaa 1560
gatggacgga ccctgtccga ttacaatatt cagaaagaaa gcaccctcca tctggtcctg 1620
aggctgcggg gaggcgacat tcagatgaca cagtccccca cctccctgtc tgccagcgtg 1680
ggagatcgcg tgaccattac ctgcagagcc tcccagtgga tcggcaacct gctggattgg 1740
tatcagcaga aacctgggga ggctcctaaa ctgctgatct attacgccag cttcctgcag 1800
tccggcgtgc cctctagatt ttccggcgga ggcttcggca cagatttcac actgaccatc 1860
tcatccctgc agcctgaaga ttttgccaca tattattgcc agcaggccaa ccctgccccc 1920
ctgacatttg gacagggaac aaaggtcgag atcaagcgcg agcctaagtc ctgtgacaag 1980
acacacacat gccctccctg cccagcccca gaactgctcg gtggaccctc tgtgtttctg 2040
tttccaccca agcctaagga tacactcatg atctccagaa cacctgaagt gacatgtgtg 2100
gtcgtcgacg tgtcacatga ggatccagaa gtcaagttta actggtatgt ggatggggtc 2160
gaggtgcaca atgccaaaac aaaacctcgg gaagaacagt ataattccac ctatagagtc 2220
gtgtctgtgc tcaccgtgct ccatcaggat tggctcaatg ggaaagaata caaatgtaaa 2280
gtctctaaca aagccctgcc cgctcctatc gaaaagacaa tctccaaggc caaaggacag 2340
cctcgcgagc ctcaggtcta caccctgcca ccttcccgcg aggaaatgac aaaaaatcag 2400
gtgtcactca cctgtctcgt gaaggggttt tacccctccg acattgccgt cgagtgggag 2460
tccaatggac agcccgagaa caattataag acaacacctc ccgtcctgga ctccgatgga 2520 tcatttttc tgtactccaa gctcaccgtc gataagtcca gatggcagca gggaaatgtc 2580
ttttcctgct ccgtgatgca tgaagctctc cacaatcatt acacacagaa aagcctgtcc 2640
ctgtcccccg gcaagtgact cgag 2664

<210> SEQ ID NO 74
<211> LENGTH: 2352
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #30

<400> SEQUENCE: 74
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780

-continued gaaccccagg tgtacacact gccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtgacattc agatgacaca gtcccccacc tccctgtctg ccagcgtggg agatcgcgtg 1380
accattacct gcagagcctc ccagtggatc ggcaacctgc tggattggta tcagcagaaa 1440
cctggggagg ctcctaaact gctgatctat tacgccagct tcctgcagtc cggcgtgccc 1500
tctagatttt ccggcggagg cttcggcaca gatttcacac tgaccatctc atccctgcag 1560
cctgaagatt ttgccacata ttattgccag caggccaacc ctgcccccct gacatttgga 1620
cagggaacaa aggtcgagat caagcgcgag cctaagtcct gtgacaagac acacacatgc 1680
cctccctgcc cagccccaga actgctcggt ggaccctctg tgtttctgtt tccacccaag 1740
cctaaggata cactcatgat ctccagaaca cctgaagtga catgtgtggt cgtcgacgtg 1800
tcacatgagg atccagaagt caagtttaac tggtatgtgg atggggtcga ggtgcacaat 1860
gccaaaacaa aacctcggga agaacagtat aattccacct atagagtcgt gtctgtgctc 1920
accgtgctcc atcaggattg gctcaatggg aaagaataca aatgtaaagt ctctaacaaa 1980
gccctgcccg ctcctatcga aaagacaatc tccaaggcca aaggacagcc tcgcgagcct 2040
caggtctaca ccctgccacc ttcccgcgag gaaatgacaa aaaatcaggt gtcactcacc 2100
tgtctcgtga aggggtttta cccctccgac attgccgtcg agtgggagtc caatggacag 2160
cccgagaaca attataagac aacacctccc gtcctggact ccgatggatc atttttttctg 2220 tactccaagc tcaccgtcga taagtccaga tggcagcagg gaaatgtctt ttcctgctcc 2280
gtgatgcatg aagctctcca caatcattac acacagaaaa gcctgtccct gtcccccggc 2340
aagtgactcg ag 2352

<210> SEQ ID NO 75
<211> LENGTH: 2679
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #31

<400> SEQUENCE: 75
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcatg cagatttttg tcaagacact gaccgggaaa 1440
acaatcacac tcgaagtcga gccctccgat acaattgaga atgtgaaagc caaaattcag 1500
gacaaagaag ggattcctcc tgatcagcag cggctgattt ttgccggaaa acagctcgaa 1560
gatggacgga ccctgtccga ttacaatatt cagaaagaaa gcaccctcca tctggtcctg 1620
aggctgcggg gaggcggcgg cggcggcagc gacattcaga tgacacagtc cccacctcc 1680
ctgtctgcca gcgtgggaga tcgcgtgacc attacctgca gagcctccca gtggatcggc 1740
aacctgctgg attggtatca gcagaaacct ggggaggctc ctaaactgct gatctattac 1800
gccagcttcc tgcagtccgg cgtgccctct agattttccg gcggaggctt cggcacagat 1860
ttcacactga ccatctcatc cctgcagcct gaagattttg ccacatatta ttgccagcag 1920
gccaaccctg ccccctgac atttggacag ggaacaaagg tcgagatcaa gcgcgagcct 1980
aagtcctgtg acaagacaca cacatgccct ccctgcccag ccccagaact gctcggtgga 2040
ccctctgtgt ttctgtttcc acccaagcct aaggatacac tcatgatctc cagaacacct 2100
gaagtgacat gtgtggtcgt cgacgtgtca catgaggatc cagaagtcaa gtttaactgg 2160
tatgtggatg gggtcgaggt gcacaatgcc aaaacaaaac ctcgggaaga acagtataat 2220
tccacctata gagtcgtgtc tgtgctcacc gtgctccatc aggattggct caatgggaaa 2280
gaatacaaat gtaaagtctc taacaaagcc ctgcccgctc ctatcgaaaa gacaatctcc 2340
aaggccaaag gacagcctcg cgagcctcag gtctacaccc tgccaccttc ccgcgaggaa 2400

```
atgacaaaaa atcaggtgtc actcacctgt ctcgtgaagg ggttttaccc ctccgacatt   2460

gccgtcgagt gggagtccaa tggacagccc gagaacaatt ataagacaac acctcccgtc   2520

ctggactccg atggatcatt ttttctgtac tccaagctca ccgtcgataa gtccagatgg   2580

cagcagggaa atgtcttttc ctgctccgtg atgcatgaag ctctccacaa tcattacaca   2640

cagaaaagcc tgtccctgtc ccccggcaag tgactcgag                          2679


<210> SEQ ID NO 76
<211> LENGTH: 2670
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #32

<400> SEQUENCE: 76

gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gcccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020

tgcagcgtga tgcacgaggc cctgcacaac cactacaccc agaagtccct gagcctgagc   1080

cccggcaaga tgcagatctt cgtgaaaacc ctgaccggca agaccatcac cctggaagtg   1140

gaacccagcg acaccatcga gaacgtgaag gccaagatcc aggacaaaga gggcatcccc   1200

cccgaccagc agagactgat cttcgccggc aagcagctgg aagatggcag aaccctgagc   1260

gactacaaca tccagaaaga gtccaccctg cacctggtgc tgcggctgag aggcggaggt   1320

ggtggtggtt ctggtggcgg aggatctggc ggtggtggat ctgggggagg tggaagtggt   1380

ggcggtggta gtggtggtgg cggaagcatg cagatttttg tcaagacact gaccgggaaa   1440

acaatcacac tcgaagtcga gccctccgat acaattgaga atgtgaaagc caaaattcag   1500

gacaaagaag ggattcctcc tgatcagcag cggctgattt ttgccggaaa acagctcgaa   1560

gatggacgga ccctgtccga ttacaatatt cagaaagaaa gcaccctcca tctggtcctg   1620
```

```
aggctgcggg gaggcggcgg cgacattcag atgacacagt cccccacctc cctgtctgcc   1680

agcgtgggag atcgcgtgac cattacctgc agagcctccc agtggatcgg caacctgctg   1740

gattggtatc agcagaaacc tggggaggct cctaaactgc tgatctatta cgccagcttc   1800

ctgcagtccg gcgtgccctc tagattttcc ggcggaggct tcggcacaga tttcacactg   1860

accatctcat ccctgcagcc tgaagatttt gccacatatt attgccagca ggccaaccct   1920

gcccccctga catttggaca gggaacaaag gtcgagatca agcgcgagcc taagtcctgt   1980

gacaagacac acacatgccc tccctgccca gccccagaac tgctcggtgg accctctgtg   2040

tttctgtttc cacccaagcc taaggataca ctcatgatct ccagaacacc tgaagtgaca   2100

tgtgtggtcg tcgacgtgtc acatgaggat ccagaagtca agtttaactg gtatgtggat   2160

ggggtcgagg tgcacaatgc caaaacaaaa cctcgggaag aacagtataa ttccacctat   2220

agagtcgtgt ctgtgctcac cgtgctccat caggattggc tcaatgggaa agaatacaaa   2280

tgtaaagtct ctaacaaagc cctgcccgct cctatcgaaa agacaatctc caaggccaaa   2340

ggacagcctc gcgagcctca ggtctacacc ctgccacctt cccgcgagga aatgacaaaa   2400

aatcaggtgt cactcacctg tctcgtgaag ggttttacc cctccgacat tgccgtcgag   2460

tgggagtcca atggacagcc cgagaacaat tataagacaa cacctcccgt cctggactcc   2520

gatggatcat tttttctgta ctccaagctc accgtcgata agtccagatg gcagcaggga   2580

aatgtctttt cctgctccgt gatgcatgaa gctctccaca atcattacac acagaaaagc   2640

ctgtccctgt cccccggcaa gtgactcgag                                     2670
```

<210> SEQ ID NO 77
<211> LENGTH: 2679
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #33

<400> SEQUENCE: 77

```
gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagcccaga    780

gaaccccagg tgtacacact gccccccagc agagaagaga tgaccaagaa ccaggtgtcc    840

ctgacctgcc tggtcaaggg cttctacccc agcgatatcg ccgtggaatg ggagagcaac    900
```

-continued ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaaga tgcagatctt cgtgaaaacc ctgaccggca agaccatcac cctggaagtg 1140
gaacccagcg acaccatcga gaacgtgaag gccaagatcc aggacaaaga gggcatcccc 1200
cccgaccagc agagactgat cttcgccggc aagcagctgg aagatggcag aaccctgagc 1260
gactacaaca tccagaaaga gtccaccctg cacctggtgc tgcggctgag aggcggaggt 1320
ggtggtggtt ctggtggcgg aggatctggc ggtggtggat ctgggggagg tggaagtggt 1380
ggcggtggta gtggtggtgg cggaagcatg cagatttttg tcaagacact gaccgggaaa 1440
acaatcacac tcgaagtcga gccctccgat acaattgaga atgtgaaagc caaaattcag 1500
gacaaagaag ggattcctcc tgatcagcag cggctgattt ttgccggaaa acagctcgaa 1560
gatggacgga ccctgtccga ttacaatatt cagaaagaaa gcaccctcca tctggtcctg 1620
aggctgcggg gaggcggcgg cggcggcagc gacattcaga tgacacagtc cccacctcc 1680 ctgtctgcca gcgtgggaga tcgcgtgacc attacctgca gagcctccca gtggatcggc 1740
aacctgctgg attggtatca gcagaaacct ggggaggctc ctaaactgct gatctattac 1800
gccagcttcc tgcagtccgg cgtgccctct agattttccg gcggaggctt cggcacagat 1860
ttcacactga ccatctcatc cctgcagcct gaagattttg ccacatatta ttgccagcag 1920
gccaaccctg ccccctgac atttggacag ggaacaaagg tcgagatcaa gcgcgagcct 1980
aagtcctgtg acaagacaca cacatgccct ccctgcccag ccccagaact gctcggtgga 2040
ccctctgtgt ttctgtttcc acccaagcct aaggatacac tcatgatctc cagaacacct 2100
gaagtgacat gtgtggtcgt cgacgtgtca catgaggatc cagaagtcaa gtttaactgg 2160
tatgtggatg gggtcgaggt gcacaatgcc aaaacaaaac ctcgggaaga acagtataat 2220
tccacctata gagtcgtgtc tgtgctcacc gtgctccatc aggattggct caatgggaaa 2280
gaatacaaat gtaaagtctc taacaaagcc ctgcccgctc ctatcgaaaa gacaatctcc 2340
aaggccaaag gacagcctcg cgagcctcag gtctacaccc tgccaccttc ccgcgaggaa 2400
atgacaaaaa atcaggtgtc actcacctgt ctcgtgaagg ggttttaccc ctccgacatt 2460
gccgtcgagt gggagtccaa tggacagccc gagaacaatt ataagacaac acctcccgtc 2520
ctggactccg atggatcatt ttttctgtac tccaagctca ccgtcgataa gtccagatgg 2580
cagcagggaa atgtcttttc ctgctccgtg atgcatgaag ctctccacaa tcattacaca 2640
cagaaaagcc tgtccctgtc ccccggcaag tgactcgag 2679

<210> SEQ ID NO 78
<211> LENGTH: 2352
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #34

<400> SEQUENCE: 78
gaattcgcca ccatgggctg gtcctgcatc atcctgtttc tggtggccac cgccaccggc 60
gtgcactctg atatccagat gacccagagc cccagcagcc tgtctgcctc tgtgggcgac 120

-continued

```
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gattttctgg cagcggcagc ggcaccgact tcaccctgac aatcagcagc    300
ctgcagcccg aggacttcgc cacctactac tgccagcagg tcctgctgta cccctacacc    360
tttggccagg gcaccaaggt ggaaatcaag agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gcccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtgacattc agatgacaca gtcccccacc tccctgtctg ccagcgtggg agatcgcgtg   1380
accattacct gcagagcctc ccagtggatc ggcaacctgc tggattggta tcagcagaaa   1440
cctggggagg ctcctaaact gctgatctat tacgccagct tcctgcagtc cggcgtgccc   1500
tctagatttt ccggcggagg cttcggcaca gatttcacac tgaccatctc atccctgcag   1560
cctgaagatt ttgccacata ttattgccag caggccaacc ctgccccccct gacatttgga   1620
cagggaacaa aggtcgagat caagcgcgag cctaagtcct gtgacaagac acacacatgc   1680
cctccctgcc cagccccaga actgctcggt ggaccctctg tgtttctgtt tccacccaag   1740
cctaaggata cactcatgat ctccagaaca cctgaagtga catgtgtggt cgtcgacgtg   1800
tcacatgagg atccagaagt caagtttaac tggtatgtgg atggggtcga ggtgcacaat   1860
gccaaaacaa aacctcggga agaacagtat aattccacct atagagtcgt gtctgtgctc   1920
accgtgctcc atcaggattg gctcaatggg aaagaataca aatgtaaagt ctctaacaaa   1980
gccctgcccg ctcctatcga aaagacaatc tccaaggcca aaggacagcc tcgcgagcct   2040
caggtctaca ccctgccacc ttcccgcgag gaaatgacaa aaaatcaggt gtcactcacc   2100
tgtctcgtga aggggtttta cccctccgac attgccgtcg agtgggagtc caatggacag   2160
cccgagaaca attataagac aacacctccc gtcctggact ccgatggatc atttttttctg   2220
tactccaagc tcaccgtcga taagtccaga tggcagcagg gaaatgtctt ttcctgctcc   2280
gtgatgcatg aagctctcca caatcattac acacagaaaa gcctgtccct gtcccccggc   2340
aagtgactcg ag                                                      2352
```

<210> SEQ ID NO 79
<211> LENGTH: 2361

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
complex comprising VEGF and EGFR specific binding peptides #33

<400> SEQUENCE: 79

```
gaattcgcca ccatgggctg gtcctgcatc atcctgtttc tggtggccac cgccaccggc     60
gtgcactctg atatccagat gacccagagc cccagcagcc tgtctgcctc tgtgggcgac    120
agagtgacca tcacctgtcg ggccagccag aagatcttca acggcctgag ctggtatcag    180
cagaagcccg gcaaggcccc caagctgctg atctaccaca gcagcaccct gcagagcggc    240
gtgccaagca gatttctgg cagcggcagc ggcaccgact tcaccctgac aatcagcagc    300
ctgcagcccg aggacttcgc cacctactac tgccagcagg tcctgctgta cccctacacc    360
tttggccagg gcaccaaggt ggaaatcaag agagagccca agagctgcga caagacccac    420
acctgtcccc cttgtcctgc ccctgaactg ctgggaggcc ctagcgtgtt cctgttcccc    480
ccaaagccca aggacaccct gatgatcagc cggacccccg aagtgacctg cgtggtggtg    540
gatgtgtccc acgaggaccc tgaagtgaag ttcaattggt acgtggacgg cgtggaagtg    600
cacaacgcca agaccaagcc cagagaggaa cagtacaaca gcacctaccg ggtggtgtcc    660
gtgctgacag tgctgcacca ggactggctg aacggcaaag agtacaagtg caaggtgtcc    720
aacaaggccc tgcctgcccc catcgagaaa accatcagca aggccaaggg ccagcccaga    780
gaaccccagg tgtacacact gccccccagc agagaagaga tgaccaagaa ccaggtgtcc    840
ctgacctgcc tggtcaaggg cttctacccc agcgatatcg ccgtggaatg ggagagcaac    900
ggccagcctg agaacaacta caagaccacc ccccctgtgc tggacagcga cggctcattc    960
ttcctgtaca gcaagctgac cgtggacaag agccggtggc agcagggcaa cgtgttcagc   1020
tgcagcgtga tgcacgaggc cctgcacaac cactacaccc agaagtccct gagcctgagc   1080
cccggcaaga tgcagatctt cgtgaaaacc ctgaccggca agaccatcac cctggaagtg   1140
gaacccagcg acaccatcga gaacgtgaag gccaagatcc aggacaaaga gggcatcccc   1200
cccgaccagc agagactgat cttcgccggc aagcagctgg aagatggcag aaccctgagc   1260
gactacaaca tccagaaaga gtccaccctg cacctggtgc tgcggctgag aggcggaggt   1320
ggtggtggtt ctgacattca gatgacacag tcccccacct ccctgtctgc cagcgtggga   1380
gatcgcgtga ccattacctg cagagcctcc cagtggatcg gcaacctgct ggattggtat   1440
cagcagaaac ctggggaggc tcctaaactg ctgatctatt acgccagctt cctgcagtcc   1500
ggcgtgccct ctagattttc cggcggaggc ttcggcacag atttcacact gaccatctca   1560
tccctgcagc ctgaagattt tgccacatat tattgccagc aggccaaccc tgccccccctg   1620
acatttggac agggaacaaa ggtcgagatc aagcgcgagc ctaagtcctg tgacaagaca   1680
cacacatgcc ctccctgccc agccccagaa ctgctcggtg gaccctctgt gtttctgttt   1740
ccacccaagc ctaaggatac actcatgatc tccagaacac ctgaagtgac atgtgtggtc   1800
gtcgacgtgt cacatgagga tccagaagtc aagtttaact ggtatgtgga tggggtcgag   1860
gtgcacaatg ccaaaacaaa acctcgggaa gaacagtata attccaccta tagagtcgtg   1920
tctgtgctca ccgtgctcca tcaggattgg ctcaatggga aagaatacaa atgtaaagtc   1980
tctaacaaag ccctgcccgc tcctatcgaa aagacaatct ccaaggccaa aggacagcct   2040
```

cgcgagcctc aggtctacac cctgccacct tcccgcgagg aaatgacaaa aaatcaggtg 2100
tcactcacct gtctcgtgaa ggggttttac ccctccgaca ttgccgtcga gtgggagtcc 2160
aatggacagc ccgagaacaa ttataagaca acacctcccg tcctggactc cgatggatca 2220
ttttttctgt actccaagct caccgtcgat aagtccagat ggcagcaggg aaatgtcttt 2280
tcctgctccg tgatgcatga agctctccac aatcattaca cacagaaaag cctgtccctg 2340
tcccccggca agtgactcga g 2361

<210> SEQ ID NO 80
<211> LENGTH: 2496
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein complex comprising VEGF and EGFR specific binding peptides #36

<400> SEQUENCE: 80
gaattcgcca ccatgggctg gtcctgcatc atcctgtttc tggtggccac cgccaccggc 60
gtgcactctg atatccagat gacccagagc cccagcagcc tgtctgcctc tgtgggcgac 120
agagtgacca tcacctgtcg ggccagccag aagatcttca acggcctgag ctggtatcag 180
cagaagcccg gcaaggcccc caagctgctg atctaccaca gcagcaccct gcagagcggc 240
gtgccaagca gattttctgg cagcggcagc ggcaccgact tcaccctgac aatcagcagc 300
ctgcagcccg aggacttcgc cacctactac tgccagcagg tcctgctgta cccctacacc 360
tttggccagg gcaccaaggt ggaaatcaag agagagccca agagctgcga caagacccac 420
acctgtcccc cttgtcctgc ccctgaactg ctgggaggcc ctagcgtgtt cctgttcccc 480
ccaaagccca aggacaccct gatgatcagc cggacccccg aagtgacctg cgtggtggtg 540
gatgtgtccc acgaggaccc tgaagtgaag ttcaattggt acgtggacgg cgtggaagtg 600
cacaacgcca agaccaagcc cagagaggaa cagtacaaca gcacctaccg ggtggtgtcc 660
gtgctgacag tgctgcacca ggactggctg aacggcaaag agtacaagtg caaggtgtcc 720
aacaaggccc tgcctgcccc catcgagaaa accatcagca aggccaaggg ccagcccaga 780
gaaccccagg tgtacacact gcccccccagc agagaagaga tgaccaagaa ccaggtgtcc 840
ctgacctgcc tggtcaaggg cttctacccc agcgatatcg ccgtggaatg ggagagcaac 900
ggccagcctg agaacaacta caagaccacc ccccctgtgc tggacagcga cggctcattc 960
ttcctgtaca gcaagctgac cgtggacaag agccggtggc agcagggcaa cgtgttcagc 1020
tgcagcgtga tgcacgaggc cctgcacaac cactacaccc agaagtccct gagcctgagc 1080
cccggcaagg gcggcatgaa gcgccagggc aaggagatgg acagcctgcg cttcctgtac 1140
gacggcatcc gcatccaggc cgaccaggcc cccgaggacc tggacatgga ggacaacgac 1200
atcatcgagg cccaccgcga gcagatcggc ggcggtggtg gtggttctgg tggcggagga 1260
tctggcggtg gtggatctgg gggaggtgga agtggtggcg gtggtagtgg tggtggcgga 1320
agcatgaagc gccagggcaa ggagatggac agcctgcgct tcctgtacga cggcatccgc 1380
atccaggccg accaggcccc cgaggacctg gacatggagg acaacgacat catcgaggcc 1440
caccgcgagc agatcggcgg cggcggcgac attcagatga cacagtcccc cacctccctg 1500
tctgccagcg tgggagatcg cgtgaccatt acctgcagag cctcccagtg gatcggcaac 1560
ctgctggatt ggtatcagca gaaacctggg gaggctccta aactgctgat ctattacgcc 1620

```
agcttcctgc agtccggcgt gccctctaga ttttccggcg gaggcttcgg cacagatttc   1680

acactgacca tctcatccct gcagcctgaa gattttgcca catattattg ccagcaggcc   1740

aaccctgccc ccctgacatt tggacaggga acaaaggtcg agatcaagcg cgagcctaag   1800

tcctgtgaca agacacacac atgccctccc tgcccagccc cagaactgct cggtggaccc   1860

tctgtgtttc tgtttccacc caagcctaag gatacactca tgatctccag aacacctgaa   1920

gtgacatgtg tggtcgtcga cgtgtcacat gaggatccag aagtcaagtt taactggtat   1980

gtggatgggg tcgaggtgca caatgccaaa acaaaacctc gggaagaaca gtataattcc   2040

acctatagag tcgtgtctgt gctcaccgtg ctccatcagg attggctcaa tgggaaagaa   2100

tacaaatgta aagtctctaa caaagccctg cccgctccta tcgaaaagac aatctccaag   2160

gccaaaggac agcctcgcga gcctcaggtc tacaccctgc caccttcccg cgaggaaatg   2220

acaaaaaatc aggtgtcact cacctgtctc gtgaaggggt tttacccctc cgacattgcc   2280

gtcgagtggg agtccaatgg acagcccgag aacaattata agacaacacc tcccgtcctg   2340

gactccgatg gatcattttt tctgtactcc aagctcaccg tcgataagtc cagatggcag   2400

cagggaaatg tcttttcctg ctccgtgatg catgaagctc tccacaatca ttacacacag   2460

aaaagcctgt ccctgtcccc cggcaagtga ctcgag                             2496


<210> SEQ ID NO 81
<211> LENGTH: 2280
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nucleotide sequence encoding the protein
      complex comprising VEGF and EGFR specific binding peptides #37

<400> SEQUENCE: 81

gaattcgcca ccatgggctg gtcctgcatc atcctgtttc tggtggccac cgccaccggc     60

gtgcactctg atatccagat gacccagagc cccagcagcc tgtctgcctc tgtgggcgac    120

agagtgacca tcacctgtcg ggccagccag aagatcttca acggcctgag ctggtatcag    180

cagaagcccg gcaaggcccc caagctgctg atctaccaca gcagcaccct gcagagcggc    240

gtgccaagca gattttctgg cagcggcagc ggcaccgact tcaccctgac aatcagcagc    300

ctgcagcccg aggacttcgc cacctactac tgccagcagg tcctgctgta cccctacacc    360

tttggccagg gcaccaaggt ggaaatcaag agagagccca agagctgcga caagacccac    420

acctgtcccc cttgtcctgc ccctgaactg ctgggaggcc ctagcgtgtt cctgttcccc    480

ccaaagccca aggacaccct gatgatcagc cggacccccg aagtgacctg cgtggtggtg    540

gatgtgtccc acgaggaccc tgaagtgaag ttcaattggt acgtggacgg cgtggaagtg    600

cacaacgcca agaccaagcc cagagaggaa cagtacaaca gcacctaccg ggtggtgtcc    660

gtgctgacag tgctgcacca ggactggctg aacggcaaag agtacaagtg caaggtgtcc    720

aacaaggccc tgcctgcccc catcgagaaa accatcagca aggccaaggg ccagccccaga    780

gaaccccagg tgtacacact gccccccagc agagaagaga tgaccaagaa ccaggtgtcc    840

ctgacctgcc tggtcaaggg cttctacccc agcgatatcg ccgtggaatg ggagagcaac    900

ggccagcctg agaacaacta caagaccacc ccccctgtgc tggacagcga cggctcattc    960

ttcctgtaca gcaagctgac cgtggacaag agccggtggc agcagggcaa cgtgttcagc   1020
```

```
tgcagcgtga tgcacgaggc cctgcacaac cactacaccc agaagtccct gagcctgagc   1080

cccggcaagg actacgacat ccccaccacc gagaacctgt acttccaggg cggtggtggt   1140

ggttctggtg gcggaggatc tggcggtggt ggatctgggg gaggtggaag tggtggcggt   1200

ggtagtggtg gtggcggaag cgagaacctg tacttccagg gctctggcgg cgacattcag   1260

atgacacagt cccccacctc cctgtctgcc agcgtgggag atcgcgtgac cattacctgc   1320

agagcctccc agtggatcgg caacctgctg gattggtatc agcagaaacc tggggaggct   1380

cctaaactgc tgatctatta cgccagcttc ctgcagtccg gcgtgccctc tagattttcc   1440

ggcggaggct tcggcacaga tttcacactg accatctcat ccctgcagcc tgaagatttt   1500

gccacatatt attgccagca ggccaaccct gcccccctga catttggaca gggaacaaag   1560

gtcgagatca agcgcgagcc taagtcctgt gacaagacac acacatgccc tccctgccca   1620

gccccagaac tgctcggtgg accctctgtg tttctgtttc cacccaagcc taaggataca   1680

ctcatgatct ccagaacacc tgaagtgaca tgtgtggtcg tcgacgtgtc acatgaggat   1740

ccagaagtca agtttaactg gtatgtggat ggggtcgagg tgcacaatgc caaaacaaaa   1800

cctcgggaag aacagtataa ttccacctat agagtcgtgt ctgtgctcac cgtgctccat   1860

caggattggc tcaatgggaa agaatacaaa tgtaaagtct ctaacaaagc cctgcccgct   1920

cctatcgaaa agacaatctc caaggccaaa ggacagcctc gcgagcctca ggtctacacc   1980

ctgccacctt cccgcgagga aatgacaaaa aatcaggtgt cactcacctg tctcgtgaag   2040

gggttttacc cctccgacat tgccgtcgag tgggagtcca atggacagcc cgagaacaat   2100

tataagacaa cacctcccgt cctggactcc gatggatcat tttttctgta ctccaagctc   2160

accgtcgata agtccagatg gcagcaggga aatgtctttt cctgctccgt gatgcatgaa   2220

gctctccaca atcattacac acagaaaagc ctgtccctgt cccccggcaa gtgactcgag   2280
```

<210> SEQ ID NO 82
<211> LENGTH: 2
<212> TYPE: PRT
<213> ORGANISM: Artificial Sequence
<220> FEATURE:
<223> OTHER INFORMATION: Synthetic linker peptide
<220> FEATURE:
<221> NAME/KEY: MISC_FEATURE
<222> LOCATION: (1)..(2)
<223> OTHER INFORMATION: sequence can be repeated up to 10 times

<400> SEQUENCE: 82

Gly Gly
1

<210> SEQ ID NO 83
<211> LENGTH: 2
<212> TYPE: PRT
<213> ORGANISM: Artificial Sequence
<220> FEATURE:
<223> OTHER INFORMATION: Synthetic linker peptide
<220> FEATURE:
<221> NAME/KEY: MISC_FEATURE
<222> LOCATION: (1)..(2)
<223> OTHER INFORMATION: sequence can be repeated up to 10 times

<400> SEQUENCE: 83

Gly Ser
1

<210> SEQ ID NO 84
<211> LENGTH: 5
<212> TYPE: PRT
<213> ORGANISM: Artificial Sequence
<220> FEATURE:
<223> OTHER INFORMATION: Synthetic linker peptide
<220> FEATURE:
<221> NAME/KEY: MISC_FEATURE
<222> LOCATION: (1)..(5)
<223> OTHER INFORMATION: sequence can be repeated up to 10 times

<400> SEQUENCE: 84

Gly Gly Gly Gly Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic TEV Protease cleavage site

<400> SEQUENCE: 85

Glu Asn Leu Tyr Phe Gln Gly
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic TEV Protease cleavage site

<400> SEQUENCE: 86

Glu Asn Leu Tyr Phe Gln Ser
1               5

<210> SEQ ID NO 87
<211> LENGTH: 4
<212> TYPE: PRT
<213> ORGANISM: Artificial Sequence
<220> FEATURE:
<223> OTHER INFORMATION: Synthetic furin cleavage peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 87

Arg Xaa Arg Arg
1

<210> SEQ ID NO 88
<211> LENGTH: 4
<212> TYPE: PRT
<213> ORGANISM: Artificial Sequence
<220> FEATURE:
<223> OTHER INFORMATION: Synthetic furin cleavage peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 88

Arg Xaa Lys Arg
1